US008835608B2

(12) United States Patent
Kuan et al.

(10) Patent No.: US 8,835,608 B2
(45) Date of Patent: Sep. 16, 2014

(54) ANTI-MRP3 ANTIBODIES AND METHODS OF USE

(75) Inventors: Chien-Tsun Kuan, Cary, NC (US); Darell D Bigner, Mebane, NC (US)

(73) Assignee: Duke University, Durham, NC (US)

( * ) Notice: Subject to any disclaimer, the term of this patent is extended or adjusted under 35 U.S.C. 154(b) by 1188 days.

(21) Appl. No.: 12/516,942

(22) PCT Filed: Nov. 30, 2007

(86) PCT No.: PCT/US2007/086128
§ 371 (c)(1),
(2), (4) Date: Dec. 29, 2009

(87) PCT Pub. No.: WO2008/143702
PCT Pub. Date: Nov. 27, 2008

(65) Prior Publication Data
US 2010/0290984 A1 Nov. 18, 2010

Related U.S. Application Data

(60) Provisional application No. 60/868,133, filed on Dec. 1, 2006, provisional application No. 60/896,128, filed on Mar. 21, 2007.

(51) Int. Cl.
*C07K 16/00* (2006.01)
*C07K 16/28* (2006.01)
*C07K 16/30* (2006.01)
*C12P 21/08* (2006.01)
*A61K 39/395* (2006.01)
*A61K 39/00* (2006.01)
*A61K 38/00* (2006.01)

(52) U.S. Cl.
CPC ........... *C07K 16/28* (2013.01); *A61K 2039/505* (2013.01); *C07K 2317/34* (2013.01); *C07K 2317/622* (2013.01); *C07K 2317/56* (2013.01); *C07K 2317/92* (2013.01); *C07K 2317/77* (2013.01)
USPC .................. 530/387.7; 530/387.9; 424/130.1; 424/138.1; 424/139.1; 514/1.1

(58) Field of Classification Search
None
See application file for complete search history.

(56) References Cited

U.S. PATENT DOCUMENTS

| 6,713,610 | B1* | 3/2004 | Kucherlapati et al. ... 530/388.23 |
| 2002/0086014 | A1* | 7/2002 | Korman et al. ............ 424/144.1 |
| 2004/0197334 | A1 | 10/2004 | Reiter et al. |
| 2005/0009119 | A1* | 1/2005 | Georges et al. .............. 435/7.23 |
| 2007/0015913 | A1 | 1/2007 | Chen et al. |

FOREIGN PATENT DOCUMENTS

WO WO 97-31111 8/1997
WO WO 2004-075842 9/2004

OTHER PUBLICATIONS

Ahern, H. Biochemical, reagent kits offer scientists good return on investment. The Scientist, 1995, vol. 9, No. 15, p. 20-25.*
Partanen, L. et al. Amplification and overexpression of the ABCC3 (MRP3) gene in primary breast cancer. Genes, Chromosomes & Cancer, 2012, vol. 51, p. 832-840.*
Steinbach, D. et al. The multidrug resistance-associated protein 3 (MRP3) is associated with a poor outcome in childhood ALL and may account for the worse prognosis in male patients and T-cell immunophenotype. Blood, 2003, vol. 102, p. 4493-4498.*
Ortiz, D.F. et al. MRP3, a new ATP-biding cassette protien localized to the canalicular of the hepatocyte. Am. Physiological Society, 1999, vol. 276, G1493-G1500.*
Konig, J., et al., "Expression and Localization of Human Multidrug Resistance Protein (ABCC) Family Members in Pancreatic Carcinoma," *Int. J. Cancer*, 115: 359-367 (2005).
Kool, M., et al., "MRP3, an Organic Anion Transporter Able to Transport Anti-Cancer Drugs," *PNAS*, 96: 6914-6919 (1999).
Ortiz, D.F., et al., "MRP3, a New ATP-Binding Cassette Protein Localized to the Canalicular of the Hepatocyte," *Amer. Physiological Society*, G1493-G1500.
Rost, D., et al., "Expression and Localization of the Multidrug Resistance-Associated Protein 3 in Rat Small and Large Intestines," *Am. J. Physiol. Gastrointest. Liver Physiol.*, 282: G720-G726 (2002).
Scheffer, G.L., et al., "Specific Detection of Multidrug Resistance Proteins MRP1, MRP2, MRP3, MRP5, and MDR3 P-Glycoprotein with a Panel of Monoclonal Antibodies," *Cancer Research*, 60: 5269-5277 (2000).
Stockel, B, et al., "Characterization of the 5'-Flanking Region of the Human Multidrug Resistance Protein 2 (MRP2) Gene and its regulation in Comparison with the Multidrug Resistance Protein 3 (MRP3) Gene," *Eur. J. Biochem.*, 267: 1347-1358 (2000).
Young, L.C., et al., "Multidrug Resistance Proteins MRP3, MRP1 and MRP2 in Lung Cancer: Correlation of Protein Levels with Drug Response and Messenger RNA Levels," *Clinical Cancer Research*, 7: 1798-1804 (2001).
Konig, J., et al., "Characterization of the Human Multidrug Resistance Protein Isoform MRP3 Localized to the Basolateral Hepatocyte Membrane," *Hepatology*, 29(4): 1156-1163 (1999).
Kool, M., Genbank Accession No. AAD01430.1; according to NCBI online revision history, first seen at NCBI on Jan. 5, 1999, pp. 1-2.

(Continued)

*Primary Examiner* — Robert Landsman
*Assistant Examiner* — Bruce D Hissong
(74) *Attorney, Agent, or Firm* — Womble Carlyle Sandridge & Rice, LLP; Carl B. Massey, Jr.; Alireza Behrooz

(57) ABSTRACT

An antibody having an antigen binding region capable of binding an epitope located in an extracellular portion of MRP3 and methods of utilizing same are provided. In particular, the invention provides antibodies targeted at a MRP3 antigen present on cells expressing MRP3 and methods useful in detecting or targeting cells expression the MRP3 antigen, as well as kits, nucleic acids, polypeptides, and cells for providing the antibodies.

14 Claims, 10 Drawing Sheets

(56) References Cited

OTHER PUBLICATIONS

Wilkstrand, C.J., et al., "Expression of Multidrug Resistance Protein 3 (MRP3) by Human Gliomas: Detection and Determination of Incidence with Polyclonal and Monoclonal Antibodies (Mabs)," *Proceedings of the American Association for Cancer Research Annual Meeting*, 44: 363-364 (2003).

Kuan, C-T., et al., "Glioma-Associated MRP3: Correlation of RNA Transcript Levels and Protein Expression," *Proceedings of the American Association for Cancer Research Annual Meeting*, 43: 968 (2002).

Binyamin, L., et al., "Targeting an Extracellular Epitope of the Human Multidrug Resistance Protein 1 (MRP1) in Malignant Cells with a Novel Recombinant Single Chain Fv Antibody," *Int'l. Journal of Cancer*, 110: 882-890 (2004).

Srivastava, N., et al., "Development of a Recombinant Single-Chain Variable Fragment (scVf) Antibody Against MRP3 (Multidrug Resistance Protein) for Immunotargeting of GBM (Glioblastoma Multiforme)," *Molecular Cancer Therapeutics*, 6(12): 3450S (2007).

Srivastava, N., et al., "Selection of a Recombinant scFv Against MRP3 for GBM Therapy," *Proceedings of the American Association for Cancer Research Annual Meeting*, 49: 566 (2008).

\* cited by examiner

HEAVY CHAIN ("V_H")

```
                    ---FR1---                     ---CDR1---   ---FR2---         -CDR2-
SEQ ID NO: 9 PepII-89   QVQLVQSGGGVVQPGRSLRLSCAASGFTFS    SYGMH  WVRQDPGKGLMWVS   SISTDG
SEQ ID NO: 5 PepI-58    EVQLVQSGGGLVQPGGSLRLSCSASGFTF     SNYAMH WVRRAPGKGLEYVS   AISSNG
SEQ ID NO:13 PepIV-17   QVQLQQSGPGLVKPSQTLSLTCAISGDSVST   NSAAWN WIRQSPSRGLEWLG   RTYYRS
SEQ ID NO: 7 PepI-25    EVQLVESGGGLVQPGGSLRLSCAASGFTFS    NYAMT  WVRQAPGKGLEWVS   AISGSG
SEQ ID NO:11 PepII-23   EVQLVQSGGGLVKPGGSLRLSCAASGFSFN    NYAGS  WVRQAPGKGLEWIS   ALSSGG

SEQ ID NO: 9 PepII-89   SATKYADSVKG  RFTISRDNAKNTVSLQMNSLRAEDTAVYYCVG  GFLGW            WGQGTLVTVSS
SEQ ID NO: 5 PepI-58    GSTYYADSVKG  RFTISRDNPKNTLYLQMNSLRAEDTAVYYCVR  GRPYPLDV         WGKGTLVTVSS
SEQ ID NO:13 PepIV-17   KWYNDYAVSVKS RITISRDNSKNHFSLQLNSVTPEDTAVYYCAR  EGNDAFDI         WGQGTMVTVSS
SEQ ID NO: 7 PepI-25    GSTYYADSVKG  RFTISRDNSKNTLYLQMNSLRAEDTAVYYCAT  GDLDY            WGQGTMVTVSS
SEQ ID NO:11 PepII-23   DTTYYADSVAG  RFAISRDNSKNTLYLQMHSLRAEDTAIYYCAQ  DPVVGAPGYFGL     WGRGTLVTVSS
                        --CDR2---                             --CDR3--              ---FR4---

SEQ ID NO:15 PepII-89 LINKER: GGGGSGGGGSGGGGS
SEQ ID NO:15 PepI-58  LINKER: GGGGSGGGGSGGGGS
SEQ ID NO:15 PepIV-17 LINKER: GGGGSGGGGSGGGGS
SEQ ID NO:15 PepI-25  LINKER: GGGGSGGGGSGGGGS
SEQ ID NO:15 PepII-23 LINKER: GGGGSGGGGSGGGGS
```

LIGHT CHAIN ("V_L")

```
                    ---FR1---                     ---CDR1---        ---FR2---
SEQ ID NO:10 PepII-89  EIVLTQSPATLSLSPGERATLSC    RASQSVGGSYLA    WYQQKPGQAPRLLIY
SEQ ID NO: 6 PepI-58   QSVLTQPPSASGTPGQRVTISCS    GSSSNIESHAVN    WYQHLPGSAPKLLIY
SEQ ID NO:14 PepIV-17  QSALTQPPSASGTPGQRVTISCS    GSSSNIGSNTVN    WYQQLPGTAPKLLIY
SEQ ID NO: 8 PepI-25   QTVVTQEPSLTVSPGGTVTLTCA    SSTGAVTSGYYPN   WFQQKPGQAPRALIY
SEQ ID NO:12 PepII-23  QSVLTQPPSASGSSGQSVTISCT    GTSSDIGGYNYVS   WYQHPGKAPKLMIY

--CDR2---                                                                --CDR3--
SEQ ID NO:10 PepII-89  GASRRAT  GIPARFSGSGSGTDFTLTISSLQPEDFASYFC  QQTNTFPLT     FGGGTKVEIKRTVAAP
SEQ ID NO: 6 PepI-58   FNNHRPS  GVPERFSASKSGTSASLAISGLQSEDEADYC   AAWDDSL       NGPVFGGGTKLTVLGQPK
SEQ ID NO:14 PepIV-17  SNNQRPS  GVPDRFSGSKSGTSASLAISGLQSEDEADYYC  EAWDDSLNGPV                                           FGGGTKLTVLGQPKATPS
SEQ ID NO: 8 PepI-25   STSNKHS  WTPARFSGSLLGGKAALTLSGVQPEDEAEYYC  LLYYGGAQPYVV  FGGGTKVTVLGQPKAAPS
SEQ ID NO:12 PepII-23  EVSKRPS  GVSDRFSGSKSGTASLHISGLQAEDEADYYC   SSYSSNNAPYV   FGSGTKVAVLGQPKAAPS
                                                  ---FR3---
```

ANTI-MRP3 ANTIBODIES AND METHODS OF USE

CROSS REFERENCE TO RELATED APPLICATIONS

The present application is a National Phase Application under §371 of International Application Serial Number PCT/US07/86128 filed on Nov. 30, 2007, the contents of which is herein incorporated by reference in its entirety, which claims benefit of priority to Provisional Application Ser. No. 60/868,133, filed on Dec. 1, 2006, the contents of which is herein incorporated by reference in its entirety, and Provisional Application Ser. No. 60/896,128, filed on Mar. 21, 2007, the contents of which is herein incorporated by reference in its entirety.

FIELD OF THE INVENTION

The present invention relates to anti-MRP3 antibodies and methods of use, in particular for detecting or targeting cells expressing MRP3.

BACKGROUND OF THE INVENTION

The human multidrug resistance protein 3 (MRP3) is an organic anion and multidrug extruding transporter. It confers multidrug resistance in human cancer cells by decreasing the intracellular concentration of drugs, which results in cancer treatment failure. With several other bacterial and eukaryotic transporters, MRP3 is a member of the C-branch of the ATP binding cassette transporter (ABC Transporter). The human MRP gene family has multiple members, including MRP1, MRP2, and several other homologous genes MRP3, MRP4, MRP5, MRP6, and MRP8. MRP3 has a molecular weight of about 190-200 kDa and is closest to MRP1, with 58% amino acid identity.

In normal human tissues, MRP3 is expressed mainly in the liver, adrenal gland, placenta, testis, intestine, pancreas, colon, gallbladder, and at a relatively lower level in kidney. Under normal physiological conditions MRP3 is highly expressed on the basolateral membrane of enterocytes and cholangiocytes. Hepatic expression of MRP3 was found to be induced in MRP2-deficient rats and, in Dubin Johnson Patients, variable levels of human MRP3 protein expression were observed in hepatocytes. Hepatic expression of MRP3 has also been linked to an elevated concentration of serum bilirubin or its glucuronides which suggests that these endogenous compounds may be involved in the induction of MRP3. Additional in vivo studies have indicated that MRP3 is an inducible transporter under cholestatic conditions. Further, phenobarbitol was reported to also induce the expression of MRP3 without affecting the levels of serum bilirubin. Functional analysis has revealed that MRP3 is involved in the cellular extrusion of organic anions it can also transport bile acid.

Expression of MRP3 was also reported in some human cell lines, including Caco-2 and HepG2, and over expression of MRP3 has been observed in some tumor cell lines that have acquired the multidrug resistance phenotype. MRP3 has also been reported to play a role in progression of adult acute myeloid leukemia. MRP3 has been identified as a novel tumor marker for glioblastoma multiforme (GBM) by serial analysis of gene expression (SAGE). MRP3 RNA transcripts have been shown to be highly expressed in GBM tissues as compared with normal brain tissues.

Antibody-based therapy has proved very effective in the detection or treatment of various cancers. For example, HERCEPTIN™ and RITUXAN™ have been used successfully to treat breast cancer and non-Hodgkin's lymphoma, respectively. HERCEPTIN™ is a recombinant DNA-derived humanized monoclonal antibody that selectively binds to the extracellular domain of the human epidermal growth factor receptor 2 (HER2) proto-oncogene. RITUXAN™ is a genetically engineered chimeric murine/human monoclonal antibody directed against the CD20 antigen found on the surface of normal and malignant B lymphocytes. Both these antibodies are produced in CHO cells.

The antigen-binding fragments (i.e., Fv fragments) are the smallest entities that consistently maintain the binding specificity of the whole antibody. Advances in antibody technology have greatly facilitated the genetic manipulation of antibody fragments. To improve stability, recombinant single-chain Fv (scFvs) have been engineered with two variable domains covalently joined by a flexible peptide linker. ScFv antibodies can have advantages over conventional antibodies, as they can be produced in large quantities and they are relatively small in size which allows them to penetrate into cells such as tumor cells more efficiently and homogenously. Their smaller size also facilitates more rapid systemic and normal tissue clearance. Recent advances in phage display technology have also permitted the production of scFvs with a higher affinity, bypassing the immune system and immunization.

Monoclonal antibodies (MAbs) detecting an internal MRP3 epitope have been developed, but nothing has been reported that can detect an external MRP3 epitope.

The present invention provides alternative methods of detecting or targeting cells expressing MRP3 that overcome the limitations of conventional methods as well as offer additional advantages that will be apparent from the detailed description below.

SUMMARY OF THE INVENTION

In one aspect, the present invention provides an isolated antibody that selectively binds an epitope located in an extracellular portion of MRP3. In one embodiment, the epitope comprises all or an antigenic fragment of an amino acid sequence as set forth in MDALCGSGELGSKFWDSNLS (SEQ ID NO:1), VHTENPDLTPCF (SEQ ID NO:2), DAMADSRQNNTSLRL (SEQ ID NO:3), or KIRSPQSFFDTTPSGRI (SEQ ID NO:4). In another embodiment, the isolated antibody comprises a domain having an amino acid sequence selected from the group consisting of a PepI-58 variable heavy domain (SEQ ID NO:5), a PepI-58 variable light domain (SEQ ID NO:6), a PepI-25 variable heavy domain (SEQ ID NO:7), a PepI-25 variable light domain (SEQ ID NO:8), a PepII-89 variable heavy domain (SEQ ID NO:9), a PepII-89 variable light domain (SEQ ID NO:10), a PepIII-23 variable heavy domain (SEQ ID NO:11), a PepIII-23 variable light domain (SEQ ID NO:12), a PepIV-17 variable heavy domain (SEQ ID NO:13), and a PepIV-17 variable light domain (SEQ ID NO:14). In other embodiments, the antibody is a single chain Fv. In one embodiment, the variable heavy chain and the variable light chain are connected by a linker, wherein the linker is a peptide having the amino acid sequence GGGGSGGGGSGGGGS (SEQ ID NO:15).

In some aspects, the present invention provides an isolated polynucleotide comprising a nucleic acid sequence selected from the group consisting of SEQ ID NO:16, SEQ ID NO:17, SEQ ID NO:18, SEQ ID NO:19, SEQ ID NO:20.

In other aspects, the present invention provides an isolated polypeptide comprising an amino acid sequence selected from the group consisting of SEQ ID NO:21, SEQ ID NO:22, SEQ ID NO:23, SEQ ID NO:24, SEQ ID NO:25.

In another aspect, the present invention provides an isolated polynucleotide comprising a nucleic acid sequence encoding an amino acid sequence selected from the group consisting of SEQ ID NO:21, SEQ ID NO:22, SEQ ID NO:23, SEQ ID NO:24, SEQ ID NO:25.

In one aspect, a nucleic acid construct is provided that comprises an isolated polynucleotide comprising a nucleic acid sequence encoding an amino acid sequence selected from the group consisting of SEQ ID NO:21, SEQ ID NO:22, SEQ ID NO:23, SEQ ID NO:24, SEQ ID NO:25. In one embodiment, the nucleic acid construct further comprises a promoter for regulating expression of the polynucleotide.

In another aspect, the present invention provides a cell comprising the nucleic acid construct.

In another aspect, the present invention provides an isolated antibody comprising:
a) a variable heavy chain comprising:
  i) a CDR1 region comprising an amino acid sequence selected from the group consisting of SEQ ID NOS: 26, 32, 38, 44, and 50,
  ii) a CDR2 region comprising an amino acid sequence selected from the group consisting of SEQ ID NOS: 27, 33, 39, 45, and 51, and
  iii) a CDR3 region comprising an amino acid sequence selected from the group consisting of SEQ ID NOS: 28, 34, 40, 46, and 52; and
b) a variable light chain comprising:
  i) a CDR1 region comprising an amino acid sequence selected from the group consisting of SEQ ID NOS: 29, 35, 41, 47, and 53,
  ii) a CDR2 region comprising an amino acid sequence selected from the group consisting of SEQ ID NOS: 30, 36, 42, 48, and 54, and
  iii) a CDR3 region comprising an amino acid sequence selected from the group consisting of SEQ ID NOS: 31, 37, 43, 49, and 55. In one embodiment, the antibody is a single chain Fv, wherein the variable heavy chain and the variable light chain are connected by a linker. In another embodiment, the single chain Fv comprises an amino acid sequence selected from the group consisting of SEQ ID NO:21, SEQ ID NO:22, SEQ ID NO:23, SEQ ID NO:24, and SEQ ID NO:25.

In one aspect, the present invention provides a method for treating cancer in a mammal. The method comprises administering to the mammal a therapeutically effective amount of a pharmaceutical composition comprising the isolated antibody.

In another aspect, the present invention provides a method for determining an MRP3-expressing cell. The method comprises contacting the cell with the isolated antibody.

In other aspects, the present invention provides a composition comprising a diagnostically effective amount of the isolated antibody; and, optionally, a carrier, wherein the composition is suitable for in vitro or in vivo assaying for MRP3.

In one aspect, a method is provided for imaging cancer in a mammal, the method comprising administering to the mammal a diagnostically effective amount of the isolated antibody that is detectably-labeled.

In another aspect, the present invention provides a pharmaceutical composition comprising the isolated antibody as an active ingredient and a pharmaceutically acceptable carrier.

In one aspect, the present invention provides a hybrid molecule comprising the isolated antibody attached to at least one effector. In one embodiment, the at least one effector is selected from the group consisting of an epitope tag, a second antibody, a label, a cytotoxin, a liposome, a radionuclide, a drug, a prodrug, a liposome, and a chelate.

In another aspect, the present invention provides a pharmaceutical composition comprising the hybrid molecule and a pharmaceutically acceptable carrier.

In other aspects, the present invention provides a method for targeted delivery of at least one effector to a cell expressing MRP3, the method comprising contacting the cell with a hybrid molecule comprising an antibody attached to the at least one effector, wherein the antibody selectively binds an epitope located in an extracellular portion of MRP3. In one embodiment, the method comprises:
a) contacting the cell with a hybrid molecule comprising an antibody attached to an epitope tag, wherein the antibody selectively binds an epitope located in an extracellular portion of MRP3;
b) contacting the hybrid molecule with a second molecule comprising at least one effector, wherein the second molecule binds to the epitope tag thereby associating the at least one effector with the hybrid molecule.

In some aspects, the present invention provides a method of detecting a cell expressing MRP3, the method comprising contacting the cell with a hybrid molecule comprising an antibody attached to a detectable label, wherein the antibody selectively binds an epitope located in an extracellular portion of MRP3; and detecting the detectable label.

In one aspect, the present invention provides a method of detecting a cell expressing MRP3, the method comprising:
a) contacting the cell with a hybrid molecule comprising an antibody attached to an epitope tag, wherein the antibody selectively binds an epitope located in an extracellular portion of MRP3;
b) contacting the hybrid molecule with a chelate comprising a detectable label, whereby the chelate binds to the epitope tag thereby associating the detectable label with the chelate; and
c) detecting the detectable label.

In other aspects, the present invention provides a method of treating cancer in an individual, the method comprising providing to the individual a therapeutically effective amount of a hybrid molecule comprising an antibody attached to an at least one effector, wherein the antibody selectively binds an epitope located in an extracellular portion of MRP3, wherein the at least one effector is selected from the group consisting of a cytotoxin, a radionuclide, a liposome comprising an anti-cancer agent, a drug, a prodrug, and an anti-cancer agent.

In another aspect, the present invention provides a method of treating cancer in an individual, the method comprising:
a) providing to the individual a therapeutically effective amount of a hybrid molecule comprising an antibody attached to an epitope tag, wherein the antibody selectively binds an epitope located in an extracellular portion of MRP3; and
b) contacting the hybrid molecule with a chelate comprising at least one effector, whereby the chelate binds to the epitope tag thereby associating the at least one effector with the chelate, wherein the at least one effector is selected from the group consisting of a cytotoxin, a radionuclide, a liposome comprising an anti-cancer agent, a drug, a prodrug, and an anti-cancer agent.

In other aspects, the present invention provides a method for killing a MRP3-expressing cell, the method comprising contacting the cell with a hybrid molecule comprising an antibody attached to an at least one effector, wherein the antibody selectively binds an epitope located in an extracellular portion of MRP3, wherein the at least one effector is selected from the group consisting of a cytotoxin, a radionuclide, a liposome comprising an anti-cancer agent, a drug, a prodrug, and an anti-cancer agent, wherein the hybrid molecule internalizes upon binding to MRP3 on the cell thereby killing the cell.

In one aspect, the present invention provides a method for killing a MRP3-expressing cell, the method comprising:
a) contacting the cell with a hybrid molecule comprising an antibody attached to an epitope tag, wherein the antibody selectively binds an epitope located in an extracellular portion of MRP3; and
b) contacting the hybrid molecule with a chelate comprising at least one effector, whereby the chelate binds to the epitope tag thereby associating the at least one effector with the chelate, wherein the at least one effector is selected from the group consisting of a cytotoxin, a radionuclide, a liposome comprising an anti-cancer agent, a drug, a prodrug, and an anti-cancer agent, wherein the at least one effector internalizes upon binding to MRP3 on the cell thereby killing the cell.

In still further aspects, a kit for determining cells expressing MRP3 is provided, the kit comprising the isolated antibody, and reagents for detecting the antibody.

In another aspect, a kit for determining cells expressing MRP3 is provided, the kit comprising a hybrid molecule comprising the isolated antibody attached to a detectable label.

In one aspect, a kit for determining cells expressing MRP3 is provided, the kit comprising:
a) a hybrid molecule comprising the isolated antibody attached to an epitope tag;
b) a chelate comprising a detectable label, whereby the chelate is capable of binding to the epitope tag thereby associating the detectable label with the chelate; and
c) reagents for detecting the detectable label.

BRIEF DESCRIPTION OF THE DRAWINGS

FIG. 3 shows the amino acid sequence alignment for anti-MRP3 antibody variable light and heavy chains (FR1-4: Framewrok Regions; CDR1-3: Complementary Determining Regions).

DETAILED DESCRIPTION

Definitions

Figure 1:
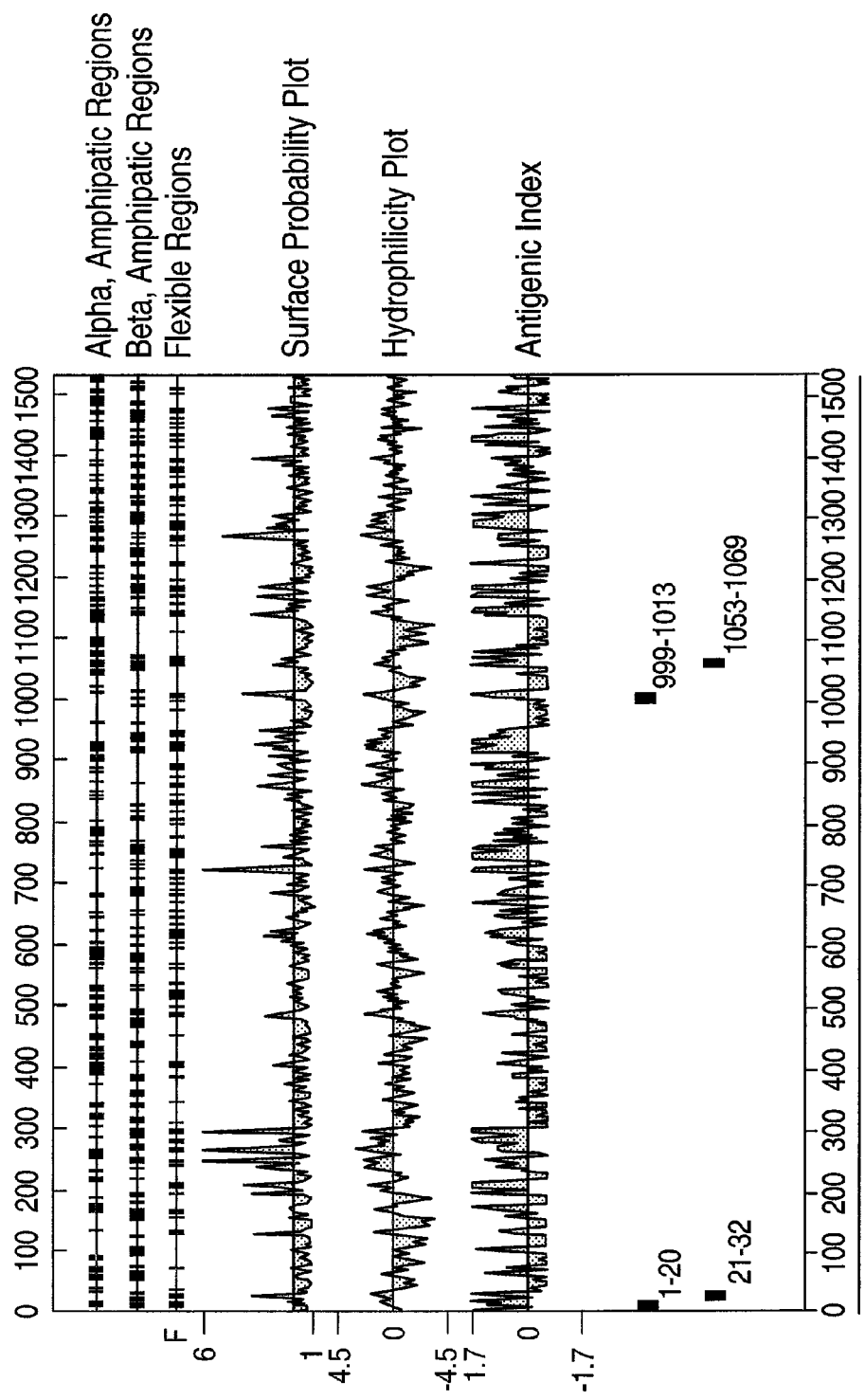
FIG. 1 shows antigenic index, hydropathy, and surface probability plot of MRP3 protein.

The term "antibody" is used in the broadest sense, and includes monoclonal antibodies (including full length monoclonal antibodies), polyclonal antibodies, multispecific antibodies (e.g., bispecific antibodies), and antibody fragments (e.g., Fab, $F(ab')_2$ and scFv) so long as they exhibit the desired biological activity. Antibodies (Abs) and immunoglobulins (Igs) are glycoproteins having the same structural characteristics. While antibodies exhibit binding specificity to a specific antigen, immunoglobulins include both antibodies and other antibody-like molecules which lack antigen specificity. Polypeptides of the latter kind are, for example, produced at low levels by the lymph system and at increased levels by myelomas.

The term "antibody fragment" refers to a portion of a full-length antibody, generally the antigen binding or variable region. Examples of antibody fragments include Fab, Fab', $F(ab')_2$ and Fv fragments. Papain digestion of antibodies produces two identical antigen binding fragments, called the Fab fragment, each with a single antigen binding site, and a residual "Fc" fragment, so-called for its ability to crystallize readily. Pepsin treatment yields an $F(ab')_2$ fragment that has two antigen binding fragments which are capable of cross-linking antigen, and a residual other fragment (which is termed pFc'). Additional fragments can include diabodies, linear antibodies, single-chain antibody molecules, and multispecific antibodies formed from antibody fragments.

An "isolated" antibody or antibody fragment is one which has been identified and separated and/or recovered from a component of the environment in which is was produced. Contaminant components of its production environment are materials which would interfere with diagnostic or therapeutic uses for the antibody, and may include enzymes, hormones, and other proteinaceous or nonproteinaceous solutes. In some embodiments, the antibody will be purified as measurable by at least three different methods: 1) to greater than 95% by weight of antibody as determined by the Lowry method, and most preferably more than 99% by weight; 2) to a degree sufficient to obtain at least 15 residues of N-terminal or internal amino acid sequence by use of a spinning cup sequenator; or 3) to homogeneity by SDS-PAGE under reducing or non-reducing conditions using Coomasie blue or, preferably, silver stain. Isolated antibody includes the antibody in situ within recombinant cells since at least one component of the antibody's natural environment will not be present. Ordinarily, however, isolated antibody will be prepared by at least one purification step.

"Single-chain Fv" or "scFv" antibody fragments comprise the $V_H$ and $V_L$ domains of an antibody, wherein these domains are present in a single polypeptide chain. Generally, the Fv polypeptide further comprises a polypeptide linker between the $V_H$ and $V_L$ domains which enables the scFv to form the desired structure for antigen binding. An Fv fragment is the minimum antibody fragment which contains a complete antigen recognition and binding site. This region consists of a dimer of one heavy and one light chain variable domain in a tight, non-covalent association ($V_H$-$V_L$ dimer). It is in this configuration that the three CDRs of each variable domain interact to define an antigen binding site on the surface of the $V_H$-$V_L$ dimer. Collectively, the six CDRs confer antigen binding specificity to the antibody. However, even a single variable domain (or half of an Fv comprising only three CDRs specific for an antigen) has the ability to recognize and bind antigen, although at a lower affinity than the entire binding site.

For a review of scFv see Pluckthun in The Pharmacology of Monoclonal Antibodies, vol. 113, Rosenburg and Moore eds. Springer-Verlag, New York, pp. 269-315 (1994).

The Fab fragment (also designated as F(ab)) also contains the constant domain of the light chain and the first constant domain (CH1) of the heavy chain. Fab' fragments differ from Fab fragments by the addition of a few residues at the carboxyl terminus of the heavy chain CH1 domain including one or more cysteines from the antibody hinge region. Fab'-SH is the designation herein for Fab' in which the cysteine residue(s) of the constant domains have a free thiol group. F(ab') fragments are produced by cleavage of the disulfide bond at the hinge cysteines of the F(ab')$_2$ pepsin digestion product. Additional chemical couplings of antibody fragments are known to those of ordinary skill in the art.

The light chains of antibodies (immunoglobulin) from any vertebrate species can be assigned to one of two clearly distinct types, called kappa (θ) and lambda (λ), based on the amino sequences of their constant domain.

Native antibodies and immunoglobulins are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (VI H) followed by a number of constant domains. Each light chain has a variable domain at one end (VL) and a constant domain at its other end. The constant domain of the light chain is aligned with the first constant domain of the heavy chain, and the light chain variable domain is aligned with the variable domain of the heavy chain. Particular amino acid residues are believed to form an interface between the light and heavy chain variable domains (Clothia et al., J. Mol. Biol. 186, 651-66, 1985); Novotny et al., Haber, Proc. Natl. Acad. Sci. USA 82, 4592-4596 (1985).

Depending on the amino acid sequences of the constant domain of their heavy chains, "immunoglobulins" can be assigned to different classes. There are at least five (5) major classes of immunoglobulins: IgA, IgD, IgE, IgG and IgM, and several of these may be further divided into subclasses (isotypes), e.g., IgG-1, IgG-2, IgG-3 and IgG4; IgA-1 and IgA-2. The heavy chains constant domains that correspond to the different classes of immunoglobulins are called α, Δ, ε, γ, and M, respectively. The subunit structures and three-dimensional configurations of different classes of immunoglobulins are well known.

The term "variant," as used herein when referring to antibodies and fragments thereof, refers to an amino acid sequence variant of an antibody wherein one or more of the amino acid residues have been modified. Such variants necessarily have less than 100% sequence identity or similarity with the amino acid sequence having at least 75% amino acid sequence identity or similarity with the amino acid sequence of either the heavy or light chain variable domain of the antibody, more preferably at least 80%, more preferably at least 85%, more preferably at least 90%, and most preferably at least 95%.

"Substitutional" variants are those that have at least one amino acid residue in a native sequence removed and a different amino acid inserted in its place at the same position. The substitutions may be single, where only one amino acid in the molecule as been substituted, or they may be multiple, where two or more amino acids have been substituted in the same molecule. "Insertional" variants are those with one or more amino acids inserted immediately adjacent to an amino acid at a particular position in a native sequence. Immediately adjacent to an amino acid means connected to either the α-carboxyl or α-amino functional group of the amino acid. "Deletional" variants are those with one or more amino acids in the native amino acid sequence removed. Ordinarily, deletional variants will have one or two amino acids deleted in a particular region of the molecule.

The term "variable" in the context of variable domain of antibodies, refers to the fact that certain portions of the variable domains differ extensively in sequence among antibodies and are used in the binding and specificity of each particular antibody for its particular antigen. However, the variability is not evenly distributed through the variable domains of antibodies. It is concentrated in three segments called complementarity determining regions (CDRs) also known as hypervariable regions both in the light chain and the heavy chain variable domains. There are at least two techniques for determining CDRs: (1) an approach based on cross-species sequence variability (i.e., Kabat et al., Sequences of Proteins of Immunological Interest (National Institute of Health, Bethesda, Md. 1987); and (2) an approach based on crystallographic studies of antigen-antibody complexes (Chothia, C. et al. (1989), Nature 342: 877). The more highly conserved portions of variable domains are called the framework (FR). The variable domains of native heavy and light chains each comprise four FR regions, largely a adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen binding site of antibodies (see Kabat et al.) The constant domains are not involved directly in binding an antibody to an antigen, but exhibit various effector function, such as participation of the antibody in antibody-dependent cellular toxicity.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In additional to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, Nature 256, 495 (1975), or may be made by recombinant methods, e.g., as described in U.S. Pat. No. 4,816,567. The monoclonal antibodies for use with the present invention may also be isolated from phage antibody libraries using the techniques described in Clackson et al. Nature 352: 624-628 (1991), as well as in Marks et al., J. Mol. Biol. 222: 581-597 (1991).

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567); Morrison et al. Proc. Natl. Acad. Sci. 81, 6851-6855 (1984).

"Humanized" forms of non-human (e.g. murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat or rabbit having the desired specificity, affinity and corresponding non-human residues. Furthermore, humanized antibody may comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin. (See, e.g., Jones et al., Nature 321, 522-525 (1986); Reichmann et al., Nature 332, 323-329 (1988); Presta, Curr. Op. Struct. Biol. 2, 593-596 (1992)).

The term "selectively binds" as used herein when referring to a biomolecule (e.g., protein, nucleic acid, antibody, etc.), refers to a binding reaction that is determinative of the presence of a particular target molecule (e.g., an epitope) in heterogeneous population of molecules (e.g., proteins and other biologics). Thus, under designated conditions (e.g., immunoassay conditions in the case of an antibody or stringent hybridization conditions in the case of a nucleic acid), the specified ligand or antibody binds to its particular "target" molecule and does not bind in a significant amount to other molecules present in the sample.

The term "hybrid molecule" used herein refers to a molecule or composition wherein two or more molecules that exist separately in their native state are joined together to form a single molecule having the desired functionality of its constituent molecules. Typically, one of the constituent molecules of a hybrid molecule is a targeting component. The targeting component is a molecule such as a ligand or an antibody (e.g., anti-MRP3 antibody) that specifically binds to its corresponding target (e.g., MRP3).

An "effector" refers to any molecule or combination of molecules whose activity it is desired to deliver to a cell.

A "reporter" is an effector that provides a detectable signal (e.g., is a detectable label). In certain embodiments, the reporter need not provide the detectable signal itself, but can simply provide a moiety that subsequently can bind to a detectable label.

The term "conservative substitution" is used in reference to proteins or peptides to reflect amino acid substitutions that do not substantially alter the activity (specificity or binding affinity) of the molecule. Typically, conservative amino acid substitutions involve substitution of one amino acid for another amino acid with similar chemical properties (e.g., charge or hydrophobicity). The following six groups each contain amino acids that are typical conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W).

The terms "epitope tag" or "affinity tag" are used interchangeably herein and refer to a molecule or domain of a molecule that is specifically recognized by an antibody or other binding partner. The term also refers to the binding partner complex as well. Thus, for example, biotin or a biotin/avidin complex are both regarded as an affinity tag. In addition to epitopes recognized in epitope/antibody interactions, affinity tags also comprise "epitopes" recognized by other binding molecules (e.g., ligands bound by receptors), ligands bound by other ligands to form heterodimers or homodimers, $His_6$ bound by Ni-NTA, biotin bound by avidin, streptavidin, or anti-biotin antibodies, and the like.

Epitope tags are well known to those of skill in the art. Moreover, antibodies specific to a wide variety of epitope tags are commercially available. These include but are not limited to antibodies against the DYKDDDDK epitope tag sequence, c-myc antibodies (available from Sigma, St. Louis), the HNK-1 carbohydrate epitope, the HA epitope, the HSV epitope, the $His_4$, $His_5$, and $His_6$ epitopes that are recognized by the His epitope specific antibodies (see, e.g., Qiagen), and the like. In addition, vectors for epitope tagging proteins are commercially available. Thus, for example, the pCMV-Tag1 vector is an epitope tagging vector designed for gene expression in mammalian cells. A target gene inserted into the pCMV-Tag1 vector can be tagged with the FLAG™ epitope (N-terminal, C-terminal or internal tagging), the c-myc epitope (C-terminal) or both the FLAG (N-terminal) and c-myc (C-terminal) epitopes.

The term "biotin" refers to biotin and modified biotins or biotin analogues that are capable of binding avidin or various avidin analogues. "Biotin", can be, inter alia, modified by the addition of one or more addends, usually through its free carboxyl residue. Useful biotin derivatives include, but are not limited to, active esters, amines, hydrazides and thiol groups that are coupled with a complimentary reactive group such as an amine, an acyl or alkyl group, a carbonyl group, an alkyl halide or a Michael-type acceptor on the appended compound or polymer.

Avidin, typically found in egg whites, has a very high binding affinity for biotin, which is a B-complex vitamin (Wilcheck et al., Anal. Biochem, 171: 1 (1988)). Streptavidin, derived from *Streptomyces avidinii*, is similar to avidin, but has lower non-specific tissue binding, and therefore often is used in place of avidin. As used herein "avidin" includes all of its biological forms either in their natural states or in their modified forms. Modified forms of avidin which have been treated to remove the protein's carbohydrate residues ("deglycosylated avidin"), and/or its highly basic charge ("neutral avidin"), for example, also are useful in the invention. Both avidin and streptavidin have a tetravalency for biotin, thus permitting amplification when the former bind to biotin. In certain embodiments, four detection or therapeutic agents, such as nuclides, can be attached to each targeting protein.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The term also includes variants on the traditional peptide linkage joining the amino acids making up the polypeptide.

The terms "nucleic acid" or "oligonucleotide" or grammatical equivalents herein refer to at least two nucleotides covalently linked together. A nucleic acid of the present invention is preferably single-stranded or double stranded and will generally contain phosphodiester bonds, although in some cases, as outlined below, nucleic acid analogs are included that may have alternate backbones, comprising, for example, phosphoramide (Beaucage et al. (1993) Tetrahedron 49(10): 1925) and references therein; Letsinger (1970) J. Org. Chem. 35:3800; Sprinzl et al. (1977) Eur. J. Biochem. 81: 579; Letsinger et al. (1986) Nucl. Acids Res. 14: 3487; Sawai et al. (1984) Chem. Lett. 805, Letsinger et al. (1988) J. Am. Chem. Soc. 110: 4470; and Pauwels et al. (1986) Chemica Scripta 26: 1419), phosphorothioate (Mag et al. (1991) Nucleic Acids Res. 19:1437; and U.S. Pat. No. 5,644, 048), phosphorodithioate (Briu et al. (1989) J. Am. Chem. Soc. 111:2321, O-methylphosphoroamidite linkages (see Eckstein, Oligonucleotides and Analogues: A Practical Approach, Oxford University Press), and peptide nucleic acid backbones and linkages (see Egholm (1992) J. Am. Chem. Soc. 114:1895; Meier et al. (1992) Chem. Int. Ed. Engl. 31: 1008; Nielsen (1993) Nature, 365: 566; Carlsson et al. (1996) Nature 380: 207). Other analog nucleic acids include those with positive backbones (Denpcy et al. (1995) Proc. Natl. Acad. Sci. USA 92: 6097; non-ionic backbones (U.S. Pat. Nos. 5,386,023, 5,637,684, 5,602,240, 5,216,141 and 4,469, 863; Angew. (1991) Chem. Intl. Ed. English 30: 423; Letsinger et al. (1988) J. Am. Chem. Soc. 110:4470; Letsinger et al. (1994) Nucleoside & Nucleotide 13:1597; Chapters 2 and 3, ASC Symposium Series 580, "Carbohydrate Modifications in Antisense Research", Ed. Y. S. Sanghui and P. Dan Cook; Mesmaeker et al. (1994), Bioorganic & Medicinal Chem. Lett. 4: 395; Jeffs et al. (1994) J. Biomolecular NMR 34:17; Tetrahedron Lett. 37:743 (1996)) and non-ribose backbones, including those described in U.S. Pat. Nos. 5,235,033 and 5,034,506, and Chapters 6 and 7, ASC Symposium Series 580, Carbohydrate Modifications in Antisense Research, Ed. Y. S. Sanghui and P. Dan Cook. Nucleic acids containing one or more carbocyclic sugars are also included within the definition of nucleic acids (see Jenkins et al. (1995), Chem. Soc. Rev. pp 169 176). Several nucleic acid analogs are described in Rawls, C & E News Jun. 2, 1997 page 35. These modifications of the ribose-phosphate backbone may be done to facilitate the addition of additional moieties such as labels, or to increase the stability and half-life of such molecules in physiological environments.

The term "residue" as used herein refers to natural, synthetic, or modified amino acids.

A "therapeutically effective amount," as used herein, refers to an amount effective to specifically kill at least a portion of the cancer cells; to specifically induce necrosis in at least a portion of the cancer; and/or to induce cancer regression or remission upon administration to the animal. Such effects are achieved while exhibiting little or no binding to, or little or no killing of, cells in normal, healthy tissues.

The term "pharmaceutically acceptable" or "pharmacologically acceptable" refers to molecular entities and compositions that do not produce an adverse, allergic or other untoward reaction when administered to an animal, or a human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. For human administration, preparations should meet sterility, pyrogenicity, general safety and purity standards as required by FDA Office of Biologics standards. Supplementary active ingredients can also be incorporated into the compositions.

I. Anti-MRP3 Antibodies

In one embodiment, the present invention provides an isolated anti-MRP3 antibody that selectively binds an epitope located in an extracellular portion of MRP3. The anti-MRP3 antibodies of this invention are particularly useful for targeting cancer cells and it will be appreciated that such targeting need not be totally specific, but is of use if it provides even differential or preferential targeted delivery to cells overexpressing MRP3 (e.g., a cancer cell). In some embodiments, the epitope is located in an amino-terminus tail or a sixth loop of the extracellular portion of human MRP3. In other embodiments, the epitope comprises all or an antigenic fragment of an amino acid sequence as set forth in Table 1.

TABLE 1

Amino acid sequences and positions for human MRP3-derived peptides.

| Name | Sequence | Residue Position[†] | MRP3 Domain | SEQ ID NO |
|---|---|---|---|---|
| PepI | MDALCGSGELGSKFWDSNLS | 1-20 | N-Terminus | 1 |
| PepII | VHTENPDLTPCF | 21-32 | N-Terminus | 2 |

TABLE 1-continued

Amino acid sequences and positions for human MRP3-derived peptides.

| Name | Sequence | Residue Position[†] | MRP3 Domain | SEQ ID NO |
|---|---|---|---|---|
| PepIII | DAMADSRQNNTSLRL | 999-1013 | Extracellular Loop 6 | 3 |
| PepIV | KIRSPQSFFDTTPSGRI | 1053-1069 | Extracellular Loop 6 | 4 |

[†]Numbering according to NCBI Accession No: AAD01430 (See also Kool et al., Proc. Natl. Acad. Sci. U.S.A. 96: 6914-6919 (1999), which is incorporated herein by reference in its entirety).

In other embodiments, the present invention provides an isolated anti-MRP3 antibody that selectively binds an epitope located in an extracellular portion of MRP3 from a mammal other than human. The mammal can be any mammal having a genome comprising a gene encoding MRP3. Examples of a mammal other than human include, but are not limited to, monkey, chimpanzee, mouse, rat, dog, cat, cow, horse, goat, sheep, etc. In one embodiment, the epitope is located in an amino-terminus tail or a sixth loop of the extracellular portion of MRP3 from a mammal selected from the group consisting of human, monkey, chimpanzee, mouse, rat, and dog.

a) Antibody Fragments

In certain circumstances there are advantages of using antibody fragments, rather than whole antibodies. The smaller size of the fragments allows for rapid clearance, and may lead to improved access to cells, in particular solid tumors. In one embodiment, the antibody is an antibody fragment.

Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992); and Brennan et al., Science, 229:81 (1985)). However, these fragments can now be produced directly by recombinant host cells. Fab, Fv and ScFv antibody fragments can all be expressed in and secreted from E. coli, thus allowing the facile production of large amounts of these fragments. Antibody fragments can be isolated from the antibody phage libraries discussed above. Alternatively, Fab'-SH fragments can be directly recovered from E. coli and chemically coupled to form F(ab').sub.2 fragments (Carter et al., Bio/Technology 10:163-167 (1992)). According to another approach, F(ab').sub.2 fragments can be isolated directly from recombinant host cell culture. Fab and F(ab').sub.2 fragment with increased in vivo half-life comprising a salvage receptor binding epitope residues are described in U.S. Pat. No. 5,869,046. Other techniques for the production of antibody fragments will be apparent to the skilled practitioner. In other embodiments, the antibody of choice is a single chain Fv fragment (scFv). See WO 93/16185; U.S. Pat. Nos. 5,571,894; and 5,587,458. Fv and sFv are the only species with intact combining sites that are devoid of constant regions; thus, they are suitable for reduced nonspecific binding during in vivo use. sFv fusion proteins may be constructed to yield fusion of an effector protein at either the amino or the carboxy terminus of an sFv. See Antibody Engineering, ed. Borrebaeck, supra. The antibody fragment may also be a "linear antibody", e.g., as described in U.S. Pat. No. 5,641,870 for example. Such linear antibody fragments may be monospecific or bispecific. In some embodiments, the antibody fragment is an Fv fragment. In other embodiments, the antibody fragment is a Fab or a F(ab')$_2$ In various embodiments, the antibodies of the present invention comprise a variable heavy and/or a variable light chain derived from (or having the sequence of) a variable heavy and/or a variable light chain of one or more of the single chain antibodies designated herein as PepI-58 scFv, PepI-25 scFv, PepII-89 scFv, PepIII-23 scFv, and PepIV-17 scFv (See, e.g., Table 2).

TABLE 2

Variable heavy and light domains of anti-MRP3 single-chain antibodies

| Domain | Amino Acid Sequence | SEQ ID NO. |
|---|---|---|
| PepI-58 scFV V$_H$ | EVQLVQSGGGLVQPGGSLRLSCSASGFTFSNYAMHWVRRAPGKGLEYV SAISSNGGSTYYADSVKGRFTISRDNPKNTLYLQMNSLRAEDTAVYYCVR GRPYPLDVWGKGTLVTVSS | 5 |
| PepI-58 scFV V$_L$ | QSVLTQPPSASGTPGQRVTISCSGSSSNIESHAVNWYQHLPGSAPKLLIY FNNHRPSGVPERFSASKSGTSASLAISGLQSEDEADYYCAAWDDSLNGPV FGGGTKLTVLGQPKAAPS | 6 |
| PepI-25 scFV V$_H$ | EVQLVESGGGLVQPGGSLRLSCAASGFTFSNYAMTWVRQAPGKGLEWVSAISGSG GSTYYADSVKGRFTISRDNSKNTLYLQMNSLRAEDTAVYYCATGDLDYWGQGTTV TVSS | 7 |
| PepI-25 scFV V$_L$ | QTVVTQEPSLTVSPGGTVTLTCASSTGAVTSGYYPNWFQQKPGQAPRALIYSTSN KHSWTPARFSGSLLGGKAALTLSGVQPEDEAEYYCLLYYGGAQPYVVFGGGTKVT VLGQPKAAPS | 8 |
| PepII-89 scFV V$_H$ | QVQLVQSGGGVVQPGRSLRLSCAASGFTFSSYGMHWVRQDPGKGLMWV SSISTDGSATKYADSVKGRFTISRDNAKNTVSLQMNSLRAEDTAVYYCVG GFLGWWGQGTLVTVSS | 9 |

TABLE 2-continued

Variable heavy and light domains of anti-MRP3 single-chain antibodies

| Domain | Amino Acid Sequence | SEQ ID NO. |
|---|---|---|
| PepII-89 scFV $V_L$ | EIVLTQSPATLSLSPGERATLSCRASQSVGGSYLAWIQQKPGQAPRLLIY GASRRATGIPARFSGSGSGTDFTLTISSLQPEDFASYFCQQTNTFPLTFG GGTKVEIKRTVAAPTAAA | 10 |
| PepIII-23 scFV $V_H$ | EVQLVQSGGGLVKPGGSLRLSCAASGFSFNNYAGSWVRQAPGKGLEWISALSSGG DTTYYADSVAGRFAISRDNSKNTLYLQMHSLRAEDTAIYYCAQDPVVGAPGYFGL WGRGTLVTVSS | 11 |
| PepIII-23 scFV $V_L$ | QSVLTQPPSASGSSGQSVTISCTGTSSDIGGYNYVSWYQQHPGKAPKLMIYEVSK RPSGVSDRFSGSKSGSTASLHISGLQAEDEADYYCSSYSSNNAPYVFGSGTKVAV LGQPKAAPS | 12 |
| PepIV-17 scFV $V_H$ | QVQLQQSGPGLVKPSQTLSLTCAISGDSVSTNSAAWNWIRQSPSRGLE WLGRTYYRSKWYNDYAVSVKSRITISPDTSKNHFSLQLNSVTPEDTAVYY CAREGNDAFDIWGQGTMVTVSS | 13 |
| PepIV-17 scFV $V_L$ | QSALTQPPSASGTPGQRVTISCSGSSSNIGSNTVNWYQQLPGTAPKLLIY SNNQRPSGVPDRFSGSKSGTSASLAISGLQSEDEADYYCEAWDDSLNGPV FGGSTKLTVLGQPKATPS | 14 |

In one embodiment, the antibody comprises a domain having an amino acid sequence selected from the group consisting of a PepI-58 variable heavy domain (SEQ ID NO:5), a PepI-58 variable light domain (SEQ ID NO:6), a PepI-25 variable heavy domain (SEQ ID NO:7), a PepI-25 variable light domain (SEQ ID NO:8), a PepII-89 variable heavy domain (SEQ ID NO:9), a PepII-89 variable light domain (SEQ ID NO:10), a PepIII-23 variable heavy domain (SEQ ID NO:11), a PepIII-23 variable light domain (SEQ ID NO:12), a PepIV-17 variable heavy domain (SEQ ID NO:13), and a PepIV-17 variable light domain (SEQ ID NO:14).

In some embodiments the variable light and variable heavy chain domains of the anti-MRP3 antibodies of the present invention are joined by a peptide linker (e.g., $Gly_4(Ser)_3$ (SEQ ID NO:15: GGGGSGGGGSGGGGS) to form a single-chain antibodies. Illustrative nucleic acid and amino acid sequences of such single-chain antibodies are shown in Tables 3 and 4, respectively.

TABLE 3

Nucleic acid sequences for Anti-MRP3 single-chain antibodies

| Name | Nucleic Acid Sequence (5' to 3') | SEQ ID NO. |
|---|---|---|
| PepI-58 scFV | GAGGTGCAGCTGGTGCAGTCTGGGGGAGGCTTGGTCCAGCCTGG GGGGTCCCTGAGACTCTCCTGTTCAGCCTCTGGATTCACCTTCAGTAACT ATGCTATGCACTGGGTCCGCCGGGCTCCAGGGAAGGGACTGGAATATGTT TCAGCTATTAGTAGTAATGGGGGTAGCACATACTACGCAGACTCCGTGAA GGGCAGATTCACCATCTCCAGAGACAATCCCAAGAACACGCTGTATCTGC AAATGAACAGTCTGAGAGCCGAGGACACGGCTGTGTATTACTGTGTAAGA GGGCGTCCCTACCCGCTGGACGTCTGGGGCAAAGGCACCCTGGTCACCGT CTCCTCAGGTGGCGGCGGTTCCGGAGGTGTGGTTCTGGCGGTGGTGGCA GCCAGTCTGTGCTGACTCAGCCACCCTCAGCGTCTGGGACCCCCGGGCAG AGGGTCACCATCTCTTGTTCTGGCAGCAGCTCCAACATCGAAAGTCATGC TGTTAATTGGTATCAGCACCTCCCAGGATCGGCCCCCAAACTCCTCATCT ATTTCAATAATCACCGGCCCTCGGGGGTCCCTGAGCGATTCTCTGCCTCC AAGTCTGGCACCTCAGCCTCCCTGGCCATCAGTGGGCTCCAGTCTGAGGA TGAGGCTGATTATTACTGTGCAGCATGGGATGACAGCCTGAATGGTCCGG TATTCGGCGGAGGGACCAAGCTGACCGTCCTAGGTCAGCCCAAGGCTGCC CCCTCG | 16 |
| PepI-25 scFV | GAGGTGCAGCTGGTGGAGTCTGGGGGAGGCTTGGTACAGCCTGGGGGGTCCCTGAGACTC TCCTGTGCAGCCTCTGGATTCACCTTTAGTAACTATGCCATGACCTGGGTCCGCCAGGCT CCAGGGAAGGGGCTGGAGTGGGTCTCAGCTATTAGTGGTAGTGGTGGTAGCACATACTAC GCAGACTCCGTGAAGGGCCGGTTCACCATCTCCAGAGACAATTCCAAGAACACGCTGTAT CTGCAAATGAACAGCCTGAGAGCCGAGGACACGGCCGTATATTACTGTGCGACGGGCGAC CTTGACTACTGGGGCCAGGGGACCACGGTCACCGTCTCCTCAGGTGGCGGCGGTTCCGGA GGTGGTGGTTCTGGCGGTGGTGGCAGCAGACTGTGGTGACTCAGGAGCCCTCACTGACT GTGTCCCCAGGAGGGACAGTCACTCTCACCTGTGCTTCCAGCACTGGAGCAGTCACCAGT GGTTACTATCCAAACTGGTTCCAGCAGAAACCTGGACAAGCACCCAGGGCACTGATTTAT AGTACAAGCAACAAACACTCCTGGACCCCTGCCCGGTTCTCAGGCTCCCTCCTTGGGGGC AAAGCTGCCCTGACACTGTCAGGTGTGCAGCCTGAGGACGAGGCTGAGTATTACTGCCTG CTCTACTATGGTGGTGCTCAGCCTTATGTGGTATTCGGCGGAGGGACCAAGGTGACCGTC CTCGGTCAGCCCAAGGCTGCCCCCTCG | 17 |

TABLE 3-continued

Nucleic acid sequences for Anti-MRP3 single-chain antibodies

| Name | Nucleic Acid Sequence (5' to 3') | SEQ ID NO. |
|---|---|---|
| PepII-89 scFV | CAGGTGCAGCTGGTGCAGTCTGGGGGAGGCGTGGTCCAGCCTGG GAGGTCCCTGAGACTCTCCTGTGCAGCGTCTGGATTCACCTTCAGTAGCT ATGGCATGCACTGGGTCCGCCAGGATCCAGGGAAGGGGCTGATGTGGGTC TCATCTATTAGTACTGATGGGAGTGCCACAAAATACGCGGACTCCGTGAA GGGCCGATTCACCATCTCCAGAGACAACGCCAAGAACACGGTGTCTCTAC AAATGAACAGTCTGAGAGCCGAAGCACGGCTGTCTATTATTGTGTAGGA GGATTTTTAGGCTGGTGGGGCCAGGGCACCCTGGTCACCGTCTCTTCAGG TGGCGGCGGTTCCGGAGGTGGTGGTTCTGGCGGTGGTGGCAGCGAAATTG TGTTGACGCAGTCTCCAGCCACCCTGTCTTTGTCTCCAGGGGAAAGAGCC ACCCTCTCCTGCAGGGCCAGCCAGAGTGTTGGCGGCAGCTACTTAGCCTG GTACCAACAGAAACCTGGCCAGGCTCCCAGGCTCCTCATCTATGGTGCAT CCAGGAGGGCCACTGGCATCCCAGCCAGGTTCAGTGGCAGTGGGTCTGGG ACAGATTTCACGCTCACCATCAGCAGTCTGCAACCTGAAGATTTTGCAAG TTACTTTTGTCAACAGACTAACACTTTTCCTCTCACCTTCGGCGGGGGA CCAAGGTGGAGATCAAACGAACTGTGGCTGCACCAACGGCGGCCGCA | 18 |
| PepIII-23 scFV | GAGGTGCAGCTGGTGCAGTCTGGGGGAGGCTTGGTCAAGCCTGGAGGGTCCCTGAGACTC TCCTGTGCAGCCTCTGGATTCAGCTTCAACAACTATGCCGGAGCTGGGTCCGCCAGGCT CCAGGGAAGGGGCTGGAATGGATCTCAGCATTGAGTAGTGGTGGTGATACCACATACTAC GCAGACTCCGTGCGGGCCGCTTCGCCATCTCCAGAGACAATTCCAAGAATACTCTGTAT CTCCAAATGCACAGTCTGAGAGCCGAGGACACGGCCATATATTATTGTGCGCAGGATCCC GTCGTGGGAGCACCTGGGTACTTCGGTCTCTGGGGCCGTGGAACCCTGGTCACCGTCTCC TCAGGTGGCGGCGGTTCCGGAGGTGGTGGTTCTGGCGGTGGTGGCAGCCAGTCTGTGCTG ACTCAGCCACCCTCCGCGTCCGGGTCTTCTGGACAGTCAGTCACCATCTCCTGCACTGGA ACCAGCAGTGACATTGGTGGTTATAACTATGTCTCCTGGTACCAACAGCACCCAGGCAAA GCCCCCAAACTCATGATTTATGAGGTCAGTAAGCGGCCCTCAGGGGTTTCTGATCGCTTC TCTGGCTCCAAGTCTGGCAGCACGGCCTCCCTGCACATCTCTGGCCTCCAGGCTGAGGAC GAGGCAGATTATTACTGCAGCTCATACTCAAGCAACAACGCTCCTTATGTCTTCGGAAGT GGGACCAAGGTCGCCGTCCTAGGTCAGCCCAAGGCCGCCCCCTCG | 19 |
| PepIV-17 scFV | CAGGTACAGCTGCAGCAGTCAGGTCCAGGACTGGTGAAGCCCTC GCAGACCCTCTCACTCACCTGTGCCATCTCCGGGACAGTGTCTCTACCA ACAGTGCTGCTTGGAACTGGATCAGGCAGTCCCATCGAGAGGCCTTGAG TGGCTGGGAAGGACATACTACAGGTCCAAGTGGTATAATGATTATGCAGT ATCTGTGAAAAGTCGAATAACCATCAGCCCAGACACATCCAAGAATCACT TCTCCCTGCAGCTGAACTCTGTGACTCCCGAGGACACGGCTGTGTATTAC TGTGCAAGAGAGGGAAATGATGCTTTTGATATCTGGGGCCAAGGGACAAT GGTCACCGTCTCCTCAGGTGGCGGCGGTTCCGGAGGTGGTGGTTCTGGCG GTGGTGGCAGCCAGTCTGCCCTGACTCAGCCACCCTCAGCGTCTGGGACC CCCGGGCAGAGGGTCACCATCTCTTGTTCTGGAAGCAGCTCCAACATCGG AAGTAATACTGTAAACTGGTACCAGCAGCTCCCAGGAACGGCCCCCAAAC TCCTCATCTATAGTAATAATCAGCGGCCCTCAGGGGTCCCTGACCGATTC TCTGGCTCCAAGTCTGGCACCTCAGCCTCCTGGCCATCAGTGGGCTCCA GTCTGAGGATGAAGCTGATTATTACTGTGAAGCATGGGATGACAGCCTGA ATGGTCCGGTGTTCGGCGGAGGGACCAAGCTGACCGTCCTAGGTCAGCCC AAGGCTACCCCCTCG | 20 |

TABLE 4

Amino acid sequences for Anti-MRP3 single-chain antibodies

| Name | Amino Acid Sequence[†] | SEQ ID NO. |
|---|---|---|
| PepI-58 scFV | EVQLVQSGGGLVQPGGSLRLSCSASGFTFSNYAMHWVRRAPGKGLEYV SAISSNGGSTYYADSVKGRFTISRDNPKNTLYLQMNSLRAEDTAVYYCVR GRPYPLDVWGKGTLVTVSS<u>GGGGSGGGGSGGGGS</u>QSVLTQPPSASGTPGQ RVTISCSGSSSNIESHAVNWYQHLPGSAPKLLIYFNNHRPSGVPERFSAS KSGTSASLAISGLQSEDEADYYCAAWDDSLNGPVFGGGTKLTVLGQPKAA PS | 21 |
| PepI-25 scFV | EVQLVESGGGLVQPGGSLRLSCAASGETFSNYAMTWVRQAPGKGLEWVSAISGSGGSTYY ADSVKGRFTISRDNSKNTLYLQMNSLRAEDTAVYYCATGDLDYWGQGTTVTVSS<u>GGGGSG GGGSGGGGS</u>QTVVTQEPSLTVSPGGTVTLTCASSTGAVTSGYYPNWFQQKPGQ<u>APRALIY</u> STSNKHSWTPARFSGSLLGGKAALTLSGVQPEDEAEYYCLLYYGGAQPYVVFGGGTKVTV LGQPKAAPS | 22 |

TABLE 4-continued

Amino acid sequences for Anti-MRP3 single-chain antibodies

| Name | Amino Acid Sequence† | SEQ ID NO. |
|---|---|---|
| PepII-89 scFV | QVQLVQSGGGVVQPGRSLRLSCAASGFTFSSYGMHWVRQDPGKGLMWV SSISTDGSATKYADSVKGRFTISRDNAKNTVSLQMNSLRAEDTAVYYCVG GFLGWWGQGTLVTVSSGGGGSGGGGSGGGGSEIVLTQSPATLSLSPGERA TLSCRASQSVGGSYLAWYQQKPGQAPRLLIYGASRRATGIPARFSGSGSG TDFTLTISSLQPEDFASYFCQQTNTFPLTFGGGTKVEIKRTVAAPTAAA | 23 |
| PepIII-23 scFV | EVQLVQSGGGLVKPGGSLRLSCAASGFSFNNYAGSWVRQAPGKGLEWISALSSGGDTTYY ADSVAGRFAISRDNSKNTLYLQMHSLRAEDTAIYYCAQDPVVGAPGYFGLWGRGTLVTVS SGGGGSGGGGSGGGGSQSVLTQPPSASGSSGQSVTISCTGTSSDIGGYNYVSWYQQHPGK APKLMIYEVSKRPSGVSDRFSGSKSGSTASLHISGLQAEDEADYYCSSYSSNNAPYVFGS GTKVAVLGQPKAAPS | 24 |
| PepIV-17 scFV | QVQLQQSGPGLVKPSQTLSLTCAISGDSVSTNSAAWNWIRQSPSRGLE WLGRTYYRSKWYNDYAVSVKSRITISPDTSKNHFSLQLNSVTPEDTAVYY CAREGNDAFDIWGQGTMVTVSSGGGGSGGGGSGGGGSQSALTQPPSASGT PGQRVTISCSGSSSNIGSNTVNWYQQLPGTAPKLLIYSNNQRPSGVPDRF SGSKSGTSASLAISGLQSEDEADYYCEAWDDSLNGPVFGGGTKLTVLGQP KATPS | 25 |

†The underlined sequence corresponds to the peptide linker.

Amino acid sequences of the complementary determining regions (CDRs) for anti-MRP3 single-chain antibodies are shown in Table 5 (See also FIG. 3).

TABLE 5

Amino acid sequences of the complementary determining regions (CDRs)

| Domain | CDR1 | CDR2 | CDR3 |
|---|---|---|---|
| | Amino Acid Sequence (SEQ ID NO) | | |
| PepI-58 scFV V$_H$ | SNYAMH (SEQ ID NO: 26) | AISSNGGSTYYADSVKG (SEQ ID NO: 27) | GRPYPLDV (SEQ ID NO: 28) |
| PepI-58 scFV V$_L$ | GSSSNIESHAVN (SEQ ID NO: 29) | FNNHRPS (SEQ ID NO: 30) | AAWDDSL (SEQ ID NO: 31) |
| PepI-25 scFV V$_H$ | NYAMT (SEQ ID NO: 32) | AISGSGGSTYYADSVKG (SEQ ID NO: 33) | GDLDY (SEQ ID NO: 34) |
| PepI-25 scFV V$_L$ | SSTGAVTSGYYPN (SEQ ID NO: 35) | STSNKHS (SEQ ID NO: 36) | LLYYGGAQPYVV (SEQ ID NO: 37) |
| PepII-89 scFV V$_H$ | SYGMH (SEQ ID NO: 38) | SISTDGGSTYYADSVKG (SEQ ID NO: 39) | GFLGW (SEQ ID NO: 40) |
| PepII-89 scFV V$_L$ | RASQSVGGSYLA (SEQ ID NO: 41) | GASRRAT (SEQ ID NO: 42) | QQTNTFPLT (SEQ ID NO: 43) |
| PepIII-23 scFV V$_H$ | NYAG (SEQ ID NO: 44) | ALSSGGDTTYYADSVAG (SEQ ID NO: 45) | DPVVGAPGYFGL (SEQ ID NO: 46) |
| PepIII-23 scFV V$_L$ | GTSSDIGGYNYVS (SEQ ID NO: 47) | EVSKRPS (SEQ ID NO: 48) | SSYSSNNAPYV (SEQ ID NO: 49) |
| PepIV-17 scFV V$_H$ | NSAAWN (SEQ ID NO: 50) | RTYYRSKWYNDYAVSVKS (SEQ ID NO: 51) | EGNDAFDI (SEQ ID NO: 52) |
| PepIV-17 scFV V$_L$ | GSSSNIGSNTVN (SEQ ID NO: 53) | SNNQRPS (SEQ ID NO: 54) | EAWDDSLNGPV (SEQ ID NO: 55) |

In one embodiment, the antibody is a single chain Fv.
In another embodiment, the antibody comprises:
a) a variable heavy chain comprising:
 i) a CDR1 region comprising an amino acid sequence selected from the group consisting of SEQ ID NOS: 26, 32, 38, 44, and 50,
 ii) a CDR2 region comprising an amino acid sequence selected from the group consisting of SEQ ID NOS: 27, 33, 39, 45, and 51, and
 iii) a CDR3 region comprising an amino acid sequence selected from the group consisting of SEQ ID NOS: 28, 34, 40, 46, and 52; and b) a variable light chain comprising:
   i) a CDR1 region comprising an amino acid sequence selected from the group consisting of SEQ ID NOS: 29, 35, 41, 47, and 53,
   ii) a CDR2 region comprising an amino acid sequence selected from the group consisting of SEQ ID NOS: 30, 36, 42, 48, and 54, and
   iii) a CDR3 region comprising an amino acid sequence selected from the group consisting of SEQ ID NOS:31, 37, 43, 49, and 55.

In one embodiment, the antibody is a single chain Fv, wherein the variable heavy chain and the variable light chain are connected by a linker. In another embodiment, the linker is a peptide having the amino acid sequence GGGGSGGGGSGGGGS (SEQ ID NO:15).

In other embodiments, the single chain Fv comprises an amino acid sequence selected from the group consisting of SEQ ID NO:21, SEQ ID NO:22, SEQ ID NO:23, SEQ ID NO:24, and SEQ ID NO:25.

b) Polyclonal Antibodies

Polyclonal antibodies can be raised in animals by multiple subcutaneous or intraperitoneal injections of the relevant antigen and an adjuvant. It may be useful to conjugate the relevant antigen (especially when synthetic peptides are used) to a protein that is immunogenic in the species to be immunized. For example, the antigen can be conjugated to keyhole limpet hemocyanin (KLH), serum albumin, bovine thyroglobulin, or soybean trypsin inhibitor, using a bifunctional or derivatizing agent, e.g., maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals can be immunized against the antigen, immunogenic conjugates, or derivatives by combining, e.g., 100 μg or 5 μg of the protein or conjugate (e.g., for rabbits or mice, respectively) with 3 volumes of Freund's complete adjuvant and injecting the solution intradermally at multiple sites. One month later, the animals can be boosted with ⅕ to ⅒ the original amount of peptide or conjugate in Freund's complete adjuvant by subcutaneous injection at multiple sites. Seven to 14 days later, the animals can be bled and the serum can be assayed for antibody titer. Animals can be boosted until the titer plateaus. Conjugates also can be made in recombinant cell culture as protein fusions. Also, aggregating agents such as alum are suitably used to enhance the immune response.

c) Monoclonal Antibodies

Monoclonal antibodies may be made using the hybridoma method described by Kohler et al., Nature, 256:495 (1975), or may be made by recombinant DNA methods (e.g., U.S. Pat. No. 4,816,567).

In the hybridoma method, a mouse or other appropriate host animal, such as a hamster, is immunized as described above to elicit lymphocytes that produce or are capable of producing antibodies that will specifically bind to the protein used for immunization. Alternatively, lymphocytes may be immunized in vitro. After immunization, lymphocytes can be isolated and then fused with a myeloma cell line using a suitable fusing agent, such as polyethylene glycol, to form a hybridoma cell (Goding, Monoclonal Antibodies: Principles and Practice, pp. 59-103 (Academic Press, 1986)).

The hybridoma cells thus prepared can be seeded and grown in a suitable culture medium which medium preferably contains one or more substances that inhibit the growth or survival of the unfused, parental myeloma cells (also referred to as fusion partner). For example, if the parental myeloma cells lack the enzyme hypoxanthine guanine phosphoribosyl transferase (HGPRT or HPRT), the selective culture medium for the hybridomas typically will include hypoxanthine, aminopterin, and thymidine (HAT medium), which substances prevent the growth of HGPRT-deficient cells.

Preferred fusion partner myeloma cells are those that fuse efficiently, support stable high-level production of antibody by the selected antibody-producing cells, and are sensitive to a selective medium that selects against the unfused parental cells. Preferred myeloma cell lines are murine myeloma lines, such as those derived from MOPC-21 and MPC-11 mouse tumors available from the Salk Institute Cell Distribution Center, San Diego, Calif. USA, and SP-2 and derivatives e.g., X63-Ag8-653 cells available from the American Type Culture Collection, Rockville, Md. USA. Human myeloma and mouse-human heteromyeloma cell lines also have been described for the production of human monoclonal antibodies (Kozbor, J. Immunol., 133:3001 (1984); and Brodeur et al., Monoclonal Antibody Production Techniques and Applications, pp. 51-63 (Marcel Dekker, Inc., New York, 1987)).

Culture medium in which hybridoma cells are growing can be assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA).

The binding affinity of the monoclonal antibody can, for example, be determined by the Scatchard analysis described in Munson et al., Anal Biochem., 107:220 (1980).

Once hybridoma cells that produce antibodies of the desired specificity, affinity, and/or activity are identified, the clones may be subcloned by limiting dilution procedures and grown by standard methods (Goding, Monoclonal Antibodies: Principles and Practice, pp. 59-103 (Academic Press, 1986)). Suitable culture media for this purpose include, for example, D-MEM or RPMI-1640 medium. In addition, the hybridoma cells may be grown in vivo as ascites tumors in an animal e.g., by intraperitoneal injection of the cells into mice.

The monoclonal antibodies secreted by the subclones are suitably separated from the culture medium, ascites fluid, or serum by conventional antibody purification procedures such as, for example, affinity chromatography (e.g., using protein A or protein G-Sepharose) or ion-exchange chromatography, hydroxylapatite chromatography, gel electrophoresis, dialysis, etc.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as E. coli cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody include Skerra et al., Curr. Opinion in Immunol., 5:256-262 (1993) and Pluckthun, Immunol. Revs., 130: 151-188 (1992).

In a further embodiment, monoclonal antibodies or antibody fragments can be isolated from antibody phage libraries generated using the techniques described in McCafferty et al., Nature, 348:552-554 (1990). Clackson et al., Nature, 352: 624-628 (1991) and Marks et al., J. Mol. Biol., 222:581-597 (1991) describe the isolation of murine and human antibodies, respectively, using phage libraries. Subsequent publications describe the production of high affinity (nM range) human antibodies by chain shuffling (Marks et al., Bio/Technology, 10:779-783 (1992)), as well as combinatorial infection and in vivo recombination as a strategy for constructing very large phage libraries (Waterhouse et al., Nuc. Acids. Res., 21:2265-2266 (1993)). Thus, these techniques are viable alternatives to traditional monoclonal antibody hybridoma techniques for isolation of monoclonal antibodies.

The DNA that encodes the antibody may be modified to produce chimeric or fusion antibody polypeptides, for example, by substituting human heavy chain and light chain constant domain ($C_H$ and $C_L$) sequences for the homologous murine sequences (U.S. Pat. No. 4,816,567; and Morrison, et al., Proc. Natl. Acad. Sci. USA, 81:6851 (1984)), or by fusing the immunoglobulin coding sequence with all or part of the coding sequence for a non-immunoglobulin polypeptide (heterologous polypeptide). The non-immunoglobulin polypeptide sequences can substitute for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

d) Bispecific Antibodies

Bispecific antibodies are antibodies that have binding specificities for at least two different epitopes. Exemplary bispecific antibodies may bind to two different epitopes of the MRP3 protein. Other such antibodies may combine an MRP3 binding site with a binding site for another protein. Alternatively, an anti-MRP3 arm may be combined with an arm which binds to a triggering molecule on a leukocyte such as a T-cell receptor molecule (e.g., CD3), or Fc receptors for IgG (FcγR), such as FcγRI (CD64), FcγRII (CD32) and FcγRIII (CD16), so as to focus and localize cellular defense mechanisms to the MRP3-expressing cell. Bispecific antibodies may also be used to localize cytotoxic agents to cells which express MRP3. These antibodies possess a MRP3-binding arm and an an arm which binds the cytotoxic agent (e.g., saporin, anti-interferon-.alpha., vinca alkaloid, ricin A chain, methotrexate or radioactive isotope hapten). Bispecific antibodies can be prepared as full length antibodies or antibody fragments (e.g., F(ab')$_2$ bispecific antibodies).

WO 96/16673 describes a bispecific anti-ErbB2/anti-FcγRIII antibody and U.S. Pat. No. 5,837,234 discloses a bispecific anti-ErbB2/anti-FcγRI antibody. A bispecific anti-ErbB2/Fcα antibody is shown in WO98/02463. U.S. Pat. No. 5,821,337 teaches a bispecific anti-ErbB2/anti-CD3 antibody.

Methods for making bispecific antibodies are known in the art. Traditional production of full length bispecific antibodies is based on the co-expression of two immunoglobulin heavy chain-light chain pairs, where the two chains have different specificities (Millstein et al., Nature, 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., EMBO J., 10:3655-3659 (1991).

According to a different approach, antibody variable domains with the desired binding specificities (antibody-antigen combining sites) are fused to immunoglobulin constant domain sequences. Preferably, the fusion is with an Ig heavy chain constant domain, comprising at least part of the hinge, $C_H2$, and $C_H3$ regions. It is preferred to have the first heavy-chain constant region ($C_H1$) containing the site necessary for light chain bonding, present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the three polypeptide fragments in embodiments when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant affect on the yield of the desired chain combination.

In another approach, the bispecific antibodies can be composed of a hybrid immunoglobulin heavy chain with a first binding specificity in one arm, and a hybrid immunoglobulin heavy chain-light chain pair (providing a second binding specificity) in the other arm. It has been shown that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., Methods in Enzymology, 121:210 (1986).

According to yet another approach described in U.S. Pat. No. 5,731,168, the interface between a pair of antibody molecules can be engineered to maximize the percentage of heterodimers which are recovered from recombinant cell culture. The preferred interface comprises at least a part of the $C_H3$ domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676, 980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., Science, 229: 81 (1985) describe a procedure wherein intact antibodies are proteolytically cleaved to generate F(ab')$_2$ fragments. These fragments are reduced in the presence of the dithiol complexing agent, sodium arsenite, to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from E. coli, which can be chemically coupled to form bispecific antibodies. Shalaby et al., J. Exp. Med., 175: 217-225 (1992) describe the production of a fully humanized bispecific antibody F(ab')$_2$ molecule. Each Fab' fragment was separately secreted from E. coli and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers (Kostelny et al., J. Immunol., 148(5):1547-1553 (1992)). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA, 90:6444-6448 (1993) has provided an alternative mechanism for making bispecific antibody fragments. The fragments comprise a $V_H$ connected to a $V_L$ by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (scFv) dimers has also been reported. See Gruber et al., J. Immunol., 152:5368 (1994).

Antibodies with more than two valencies are contemplated. For example, trispecific antibodies can be prepared. Tutt et al., J. Immunol. 147: 60 (1991).

e) Multivalent Antibodies

The antibodies of the present invention can be multivalent antibodies (which are other than of the IgM class) with three or more antigen binding sites (e.g., tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody can comprise an Fc region and three or more antigen binding sites aminoterminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable domains. For instance, the polypeptide chain(s) may comprise VD1-(X1)$_n$-VD2-(X2)$_n$-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a $C_L$ domain.

f) Nanobodies

Nanobodies, which are derived from the $V_HH$ domains of heavy-chain antibodies, are the smallest antigen-binding domains.

In one aspect, the present invention provides an antibody or (functionalized) fragment thereof derived from a heavy chain immunoglobulin of Camelidae, wherein the antibody comprises a CDR different from the CDR belonging to the natural antibody of Camelidae which is grafted on the framework of the variable domain of the heavy chain immunoglobulin of a Camelidae species, for example camel, dromedary, alpaca, and guanaco. Other species besides Camelidae produce heavy chain antibodies naturally devoid of light chain; such $V_HH$s also are within the scope of the invention. In one embodiment, the CDR is as described above.

$V_HH$s are described in U.S. Pat. Nos. 5,800,988, 5,840, 526, 5,874,541, 6,005,079, 6,015,695, and 6,838,254, which are incorporated herein by reference for their teaching of $V_HH$s.

g) scFV-Fc Fusions scFvs selected from the scFv-phage libraries are redesigned to incorporate the Fc region to form scFv-Fc fusion proteins. The fusion of scFvs with Fc not only prolongs the serum half-life and stability of the scFvs but also improves their therapeutic efficacy owing to the ADCC and CDC mediated by the Fc portion. In one embodiment, the anti-MRP3 scFvs of the present invention are fused with Fc.

h) De-Immunization

De-immunization is another approach to reduce the immunogenicity of chimeric or mouse antibodies. It involves the identification of linear T-cell epitopes in the antibody of interest, using bioinformatics, and their subsequent replacement by site-directed mutagenesis to human or non-immunogenic sequences. In one embodiment, the antibodies of the present invention are de-immunized.

II. Preparation and Modification of Antibodies

Using the information provided herein, anti-MRP3 antibodies of this invention can be prepared using either chemical synthetic means or by the use of recombinant expression systems. In addition, other "related" anti-MRP3 antibodies can be identified by screening for antibodies that bind to the same epitope and/or by modification of the anti-MRP3 antibodies (e.g., PepI-58 scFv, PepI-25 scFv, PepII-89 scFv, PepIII-23 scFV, PepIV-17 scFv) to produce libraries of modified antibody and then rescreening antibodies in the library for improved MRP3 avidity.

a) Antibody Synthesis.

1) Chemical Synthesis.

Using the sequence information provided herein, the anti-MRP3 antibodies of this invention (e.g., PepI-58 scFv, PepI-25 scFv, PepII-89 scFv, PepIII-23 scFV, PepIV-17 scFv), or variants thereof, can be chemically synthesized using well known methods of peptide synthesis. Solid phase synthesis in which the C-terminal amino acid of the sequence is attached to an insoluble support followed by sequential addition of the remaining amino acids in the sequence is one preferred method for the chemical synthesis of single chain antibodies. Techniques for solid phase synthesis are described by Barany and Merrifield, Solid Phase Peptide Synthesis; pp. 3 284 in The Peptides: Analysis, Synthesis, Biology. Vol. 2: Special Methods in Peptide Synthesis, Part A., Merrifield et al. (1963) J. Am. Chem. Soc., 85: 2149 2156, and Stewart et al. (1984) Solid Phase Peptide Synthesis, 2nd ed. Pierce Chem. Co., Rockford, Ill.

2) Recombinant Expression of Anti-MRP3 Antibodies

In some embodiments, the anti-MRP3 antibodies of this invention (e.g., PepI-58 scFv, PepI-25 scFv, PepII-89 scFv, PepIII-23 scFV, and PepIV-17 scFv), or variants thereof, are prepared using standard techniques well known to those of skill in the art. Using the sequence information provided herein, nucleic acids encoding the desired antibody can be chemically synthesized according to a number of standard methods known to those of skill in the art. Oligonucleotide synthesis, is preferably carried out on commercially available solid phase oligonucleotide synthesis machines (Needham-VanDevanter et al. (1984) Nucleic Acids Res. 12: 6159 6168) or manually synthesized using the solid phase phosphoramidite triester method described by Beaucage et. al. (Beaucage et. al. (1981) Tetrahedron Letts. 22(20): 1859 1862). Alternatively, nucleic acids encoding the antibody can be amplified and/or cloned according to standard methods.

Molecular cloning techniques to achieve these ends are known in the art. A wide variety of cloning and in vitro amplification methods are suitable for the construction of recombinant nucleic acids. Examples of these techniques and instructions sufficient to direct persons of skill through many cloning exercises are found in Berger and Kimmel, Guide to Molecular Cloning Techniques, Methods in Enzymology volume 152 Academic Press, Inc., San Diego, Calif. (Berger); Sambrook et al. (1989) Molecular Cloning A Laboratory Manual (2nd ed.) Vol. 1 3, Cold Spring Harbor Laboratory, Cold Spring Harbor Press, N.Y., (Sambrook); and Current Protocols in Molecular Biology, F. M. Ausubel et al., eds., Current Protocols, a joint venture between Greene Publishing Associates, Inc. and John Wiley & Sons, Inc., (1994 Supplement) (Ausubel). Methods of producing recombinant immunoglobulins are also known in the art. See, Cabilly, U.S. Pat. No. 4,816,567; and Queen et al. (1989) Proc. Natl. Acad. Sci. USA 86: 10029 10033. In addition, detailed protocols for the expression of the antibodies of this invention are provided herein in the Examples.

b) Identification of Other Antibodies Binding the Same Epitope as PepI-58 scFv, PepI-25 scFv, PepII-89 scFv, PepIII-23 scFV, and PepIV-17 scFv Having identified useful anti-MRP3 antibodies (e.g., PepI-58 scFv, PepI-25 scFv, PepII-89 scFv, PepIII-23 scFV, and PepIV-17 scFv), other "related" anti-MRP3 antibodies can be identified by screening for antibodies that cross-react with the identified antibodies, either at the epitope bound by the antibodies or with an idiotypic antibody raised against the anti-MRP3 antibodies of this invention.

1) Cross-Reactivity with Anti-Idiotypic Antibodies

The idiotype represents the highly variable antigen-binding site of an antibody and is itself immunogenic. During the generation of an antibody-mediated immune response, an individual will develop antibodies to the antigen as well as anti-idiotype antibodies, whose immunogenic binding site (idiotype) mimics the antigen.

Anti-idiotypic antibodies can be raised against the variable regions of the antibodies identified herein using standard methods well known to those of skill in the art. Briefly, anti-idiotype antibodies can be made by injecting the antibodies of this invention, or fragments thereof (e.g., CDRs) into an animal thereby eliciting antisera against various antigenic determinants on the antibody, including determinants in the idiotypic region.

Methods for the production of anti-idiotype antibodies are well known in the art. Large molecular weight antigens (greater than approx. 5000 Daltons) can be injected directly into animals, whereas small molecular weight compounds (less than approx. 5000 Daltons) are preferably coupled to a high molecular weight immunogenic carrier, usually a protein, to render them immunogenic. The antibodies produced in response to immunization can be utilized as serum, ascites fluid, an immunoglobulin (Ig) fraction, an IgG fraction, or as affinity-purified monospecific material.

Polyclonal anti-idiotype antibodies can be prepared by immunizing an animal with the antibodies of this invention prepared as described above. In general, it is desirable to immunize an animal which is species and allotype-matched with the animal from which the antibody (e.g., phage-display library) was derived. This minimizes the production of antibodies directed against non-idiotypic determinants. The antiserum so obtained is then usually absorbed extensively against normal serum from the same species from which the phage-display library was derived, thereby eliminating antibodies directed against non-idiotypic determinants. Absorption can be accomplished by passing antiserum over a gel formed by crosslinking normal (nonimmune) serum proteins with glutaraldehyde. Antibodies with anti-idiotypic specificity will pass directly through the gel, while those having specificity for non-idiotypic determinants will bind to the gel. Immobilizing nonimmune serum proteins on an insoluble polysaccharide support (e.g., sepharose) also provides a suitable matrix for absorption.

Monoclonal anti-idiotype antibodies can be produced using the method of Kohler et al. (1975) Nature 256: 495. In particular, monoclonal anti-idiotype antibodies can be prepared using hybridoma technology which comprises fusing (1) spleen cells from a mouse immunized with the antigen or hapten-carrier conjugate of interest (i.e., the antibodies or this invention or subsequences thereof) to (2) a mouse myeloma cell line which has been selected for resistance to a drug (e.g., 8-azaguanine). In general, it is desirable to use a myeloma cell line which does not secrete an immunoglobulin. Several such lines are known in the art. A preferred cell line is P3X63Ag8.653. This cell line is on deposit at the American Type Culture Collection as CRL-1580.

Fusion can be carried out in the presence of polyethylene glycol according to established methods (see, e.g., Monoclonal Antibodies, R. Kennett, J. McKearn & K. Bechtol, eds. N.Y., Plenum Press, 1980, and Current Topics in Microbiology & Immunology, Vol. 81, F. Melchers, M. Potter & N. L. Warner, eds., N.Y., Springer-Verlag, 1978). The resultant mixture of fused and unfused cells is plated out in hypoxanthine-aminopterin-thymidine (HAT) selective medium. Under these conditions, only hybrid cells will grow.

When sufficient cell growth has occurred, (typically 10-14 days post-fusion), the culture medium is harvested and screened for the presence of monoclonal idiotypic, anti-analyte antibody by any one of a number of methods which include solid phase RIA and enzyme-linked immunosorbent assay. Cells from culture wells containing antibody of the desired specificity are then expanded and recloned. Cells from those cultures that remain positive for the antibody of interest are then usually passed as ascites tumors in susceptible, histocompatible, pristane-primed mice.

Ascites fluid is harvested by tapping the peritoneal cavity, retested for antibody, and purified as described above. If a nonsecreting myeloma line is used in the fusion, affinity purification of the monoclonal antibody is not usually necessary since the antibody is already homogeneous with respect to its antigen-binding characteristics. All that is necessary is to isolate it from contaminating proteins in ascites, i.e., to produce an immunoglobulin fraction.

Alternatively, the hybrid cell lines of interest can be grown in serum-free tissue culture and the antibody harvested from the culture medium. In general, this is a less desirable method of obtaining large quantities of antibody because the yield is low. It is also possible to pass the cells intravenously in mice and to harvest the antibody from serum. This method is generally not preferred because of the small quantity of serum which can be obtained per bleed and because of the need for extensive purification from other serum components. However, some hybridomas will not grow as ascites tumors and therefore one of these alternative methods of obtaining antibody must be used.

2) Cross-Reactivity with the Anti-MRP3 Antibodies of this Invention

Instead of the anti-idiotypic antibody, other anti-MRP3 antibodies of this invention can be identified by the fact that they bind the same epitope as the "prototypic" antibodies of this invention (e.g., PepI-58 scFv, PepI-25 scFv, PepII-89 scFv, PepIII-23 scFV, PepIV-17 scFv, etc.). Methods of determining antibody cross-reactivity are well known to those of skill in the art. Generally the epitope bound by the prototypic antibodies of this invention is determined e.g., by epitope mapping techniques. Methods of epitope mapping are well known to those of skill in the art (see, e.g., Reyes et al. (1992) Hepatitis E Virus (HEV): Epitope Mapping and Detection of Strain Variation, Elsevier Science Publisher Shikata et al. eds., Chapter 43:237 245; Li et al. (1993) Nature 363: 85 88). Epitope mapping can be performed using Novatope system, a kit for which is commercially available from Novagen, Inc.

Once the epitope bound by the prototypic antibodies of this invention is elucidated, the ability of newly generated anti-MRP3 antibodies to bind the same epitope is determined, e.g., using standard immune assays such as a sandwich assay, a BioCore assay, etc. Examples of a cross-reactivity assay are provided in U.S. Pat. No. 6,197,938. Preferred cross-reactive anti-MRP3 antibodies show at least 60%, preferably 80%, more preferably 90%, and most preferably at least 95% or at least 99% cross-reactivity with one or more of the prototypic antibodies of this invention.

c) Amino Acid Sequence Modifications

Amino acid sequence modification(s) of the anti-MRP3 antibodies described herein are contemplated. For example, it may be desirable to improve the binding affinity and/or other biological properties of the antibody. Amino acid sequence variants of the anti-MRP3 antibody are prepared by introducing appropriate nucleotide changes into the anti-MRP3 antibody nucleic acid, or by peptide synthesis. Such modifications include, for example, deletions from, and/or insertions into and/or substitutions of, residues within the amino acid sequences of the anti-MRP3 antibody. Any combination of deletion, insertion, and substitution is made to arrive at the final construct, provided that the final construct possesses the desired characteristics. The amino acid changes also may alter post-translational processes of the anti-MRP3 antibody, such as changing the number or position of glycosylation sites.

A useful method for identification of certain residues or regions of the anti-MRP3 antibody that are preferred locations for mutagenesis is called "alanine scanning mutagenesis" as described in Cunningham et al., Science, 244:1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with MRP3 antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, alanine scanning or random mutagenesis is conducted at the target codon or region and the expressed anti-MRP3 antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an anti-MRP3 antibody with an N-terminal methionyl residue or the antibody fused to a cytotoxic polypeptide. Other insertional variants of the anti-MRP3 antibody molecule include the fusion to the N- or C-terminus of the anti-MRP3 antibody to an enzyme (e.g., for ADEPT) or a polypeptide which increases the serum half-life of the antibody.

Another type of variant is an amino acid substitution variant. These variants have at least one amino acid residue in the anti-MRP3 antibody molecule replaced by a different residue. The sites of greatest interest for substitutional mutagenesis include the hypervariable regions, but FR alterations are also contemplated. Conservative substitutions are shown in Table 6 under the heading of "preferred substitutions". If such substitutions result in a change in biological activity, then more substantial changes, denominated "exemplary substitutions" in Table 4, or as further described below in reference to amino acid classes, may be introduced and the products screened.

TABLE 6

Amino acid substitutions

| Original | Exempleray Substitution | Preferred Substitution |
|---|---|---|
| Ala (A) | val; leu; ile | Val |
| Arg (R) | lys; gln; asn | Lys |
| Asn (N) | gln; his; asp, lys; arg | Gln |
| Asp (D) | glu; asn | Glu |
| Cys (C) | ser; ala | Ser |
| Gln (Q) | asn; glu | Asn |

TABLE 6-continued

Amino acid substitutions

| Original | Exempleray Substitution | Preferred Substitution |
|---|---|---|
| Glu (E) | asp; gln | Asp |
| Gly (G) | ala | Ala |
| His (H) | asn; gln; lys; arg | Arg |
| Ile (I) | leu; val; met; ala; phe; norleucine | Leu |
| Leu (L) | norleucine; ile; val; met; ala; phe | Ile |
| Lys (K) | arg; gln; asn | Arg |
| Met (M) | leu; phe; ile | Leu |
| Phe (F) | leu; val; ile; ala; tyr | Tyr |
| Pro (P) | ala | Ala |
| Ser (S) | thr | Thr |
| Thr (T) | ser | Ser |
| Trp (W) | tyr; phe | Tyr |
| Tyr (Y) | trp; phe; thr; ser | Phe |
| Val (V) | ile; leu; met; phe; ala; norleucine | Leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties: (1) hydrophobic: norleucine, met, ala, val, leu, ile; (2) neutral hydrophilic: cys, ser, thr; (3) acidic: asp, glu; (4) basic: asn, gln, his, lys, arg; (5) residues that influence chain orientation: gly, pro; and (6) aromatic: trp, tyr, phe. Non-conservative substitutions will entail exchanging a member of one of these classes for another class.

Any cysteine residue not involved in maintaining the proper conformation of the anti-MRP3 antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

A particularly preferred type of substitutional variant involves substituting one or more hypervariable region residues of a parent antibody (e.g., a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and MRP3. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antibody alters the original glycosylation pattern of the antibody. By altering is meant deleting one or more carbohydrate moieties found in the antibody, and/or adding one or more glycosylation sites that are not present in the antibody.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Nucleic acid molecules encoding amino acid sequence variants of the anti-MRP3 antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the anti-MRP3 antibody.

It may be desirable to modify the antibody of the invention with respect to effector function, e.g., so as to enhance antigen-dependent cell-mediated cyotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., J. Exp Med. 176:1191-1195 (1992) and Shopes, B. J. Immunol. 148:2918-2922 (1992). Homodimeric antibodies with enhanced antitumor activity may also be prepared using heterobifunctional cross-linkers as described in Wolff et al. Cancer Research 53:2560-2565 (1993). Alternatively, an antibody can be engineered which has dual Fc regions and may thereby have enhanced complement lysis and ADCC capabilities. See Stevenson et al. Anti-Cancer Drug Design 3:219-230 (1989).

To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

d) Phase Display Methods to Select Other "Related" Anti-MRP3 Antibodies

1) Chain Shuffling Methods

To create higher affinity antibodies, mutant scFv gene repertories, based on the sequence of a binding of an identified anti-MRP3 antibody (e.g., PepI-58 scFv, PepI-25 scFv, PepII-89 scFv, PepIII-23 scFV, PepIV-17 scFv, etc.) are created and expressed on the surface of phage. Higher affinity scFvs are selected on antigen, e.g., as described above.

One approach to creating modified single-chain antibody (scFv) gene repertoires has been to replace the original $V_H$ or $V_L$ gene with a repertoire of V-genes to create new partners (chain shuffling) (Clackson et al. (1991) Nature. 352: 624 628). Using chain shuffling and phage display, the affinity of a human scFv antibody fragment that bound the hapten phenyloxazolone (phOx) was increased from 300 nM to 1 nM (300 fold) (Marks et al. (1992) Bio/Technology 10: 779 783).

Thus, for example, to alter the affinity of an anti-MRP3 antibody, a mutant scFv gene repertoire can be created containing the $V_H$ gene of the anti-MRP3 antibody (e.g., PepI-58 scFv, PepI-25 scFv, PepII-89 scFv, PepIII-23 scFv, PepIV-17 scFv, etc.) and a human $V_L$ gene repertoire (light chain shuffling). The scFv gene repertoire can be cloned into a phage display vector, e.g., pHEN-1 (Hoogenboom et al. (1991) Nucleic Acids Res., 19: 4133 4137) and after transformation a library of transformants is obtained.

Similarly, for heavy chain shuffling, the anti-MRP3 antibody (e.g., PepI-58 scFv, PepI-25 scFv, PepII-89 scFv, PepIII-23 scFV, PepIV-17 scFv, etc.) $V_H$ CDR1 and/or CDR2, and/or CDR3 and light chain are cloned into a vector containing a human $V_H$ gene repertoire to create a phage antibody library transformants. For detailed descriptions of chain shuffling to increase antibody affinity see Schier et al. (1996) J. Mol. Biol., 255: 28 43, 1996.

2) Site-Directed Mutagenesis to Improve Binding Affinity

The majority of antigen contacting amino acid side chains are typically located in the complementarity determining regions (CDRs), three in the $V_H$ (CDR1, CDR2, and CDR3) and three in the $V_L$ (CDR1, CDR2, and CDR3) (Chothia et al. (1987) J. Mol. Biol., 196: 901 917; Chothia et al. (1986) Science, 233: 755 8; Nhan et al. (1991) J. Mol. Biol., 217: 133 151). These residues contribute the majority of binding energetics responsible for antibody affinity for antigen. In other molecules, mutating amino acids which contact ligand has been shown to be an effective means of increasing the affinity of one protein molecule for its binding partner (Lowman et al. (1993) J. Mol. Biol., 234: 564 578; Wells (1990) Biochemistry, 29: 8509 8516). Site-directed mutagenesis of CDRs and screening against MRP3 antibodies having improved binding affinity.

3) CDR Randomization to Produce Higher Affinity Human scFv

In an extension of simple site-directed mutagenesis, mutant antibody libraries can be created where partial or entire CDRs are randomized ($V_L$ CDR1 and CDR2 and $V_H$ CDR1, CDR2 and CDR3). In one embodiment, each CDR is randomized in a separate library, using the known anti-MRP3 antibody (e.g., PepI-58 scFv, PepI-25 scFv, PepII-89 scFv, PepIII-23 scFV, PepIV-17 scFv, etc.) as a template. The CDR sequences of the highest affinity mutants from each CDR library are combined to obtain an additive increase in affinity. A similar approach has been used to increase the affinity of human growth hormone (hGH) for the growth hormone receptor over 1500 fold from $3.4 \times 10^{-10}$ to $9.0 \times 10^{-13}$ M (Lowman et al. (1993) J. Mol. Biol., 234: 564 578).

$V_H$ CDR3 often occupies the center of the binding pocket, and thus mutations in this region are likely to result in an increase in affinity (Clackson et al. (1995) Science, 267: 383 386). In one embodiment, four $V_H$ CDR3 residues are randomized at a time using the nucleotides NNS (see, e.g., Schier et al. (1996) Gene, 169: 147 155; Schier and Marks (1996) Human Antibodies and Hybridomas. 7: 97 105, 1996; and Schier et al. (1996) J. Mol. Biol. 263: 551567, 1996).

4) Creation of Homodimers

To create (scFv')$_2$ antibodies, two anti-MRP3 scFvs are joined, either through a linker (e.g., a carbon linker, a peptide, etc.) or through a disulfide bond between, for example, two cysteines. Thus, for example, to create disulfide linked scFv, a cysteine residue is introduced by site directed mutagenesis at the carboxy-terminus of the antibodies described herein.

An scFv can be expressed from this construct, purified by IMAC, and analyzed by gel filtration. To produce (scFv')$_2$ dimers, the cysteine is reduced by incubation with 1 mM β-mercaptoethanol, and half of the scFv blocked by the addition of DTNB. Blocked and unblocked scFvs are incubated together to form (scFv')$_2$ and the resulting material can be analyzed by gel filtration. The affinity of the resulting dimmer can be determined using standard methods, e.g., by BiaCore.

In a particularly preferred embodiment, the (scFv')$_2$ dimer is created by joining the scFv' fragments through a linker, more preferably through a peptide, linker. This can be accomplished by a wide variety of means well known to those of skill in the art. For example, one preferred approach is described by Holliger et al. (1993) Proc. Natl. Acad. Sci. USA, 90: 6444 6448 (see also WO 94/13804).

5) Measurement of Antibody/Polypeptide Binding Affinity

As explained above, selection for increased avidity involves measuring the affinity of the antibody for the target antigen. Methods of making such measurements are well known to, those of skill in the art. Briefly, for example, the $K_d$ of PepI-58 scFv, PepI-25 scFv, PepII-89 scFv, PepIII-23 scFV, PepIV-17 scFv antibody can be determined from the kinetics of binding to MRP3 in a BIAcore, a biosensor based on surface plasmon resonance. For this technique, antigen is coupled to a derivatized sensor chip capable of detecting changes in mass. When antibody is passed over the sensor chip, antibody binds to the antigen resulting in an increase in mass that is quantifiable. Measurement of the rate of association as a function of antibody concentration can be used to calculate the association rate constant ($k_{on}$). After the association phase, buffer is passed over the chip and the rate of dissociation of antibody ($k_{off}$) determined. $K_{on}$ is typically measured in the range $1.0 \times 10^2$ to $5.0 \times 10^6$ and $k_{off}$ in the range $1.0 \times 10^{-1}$ to $1.0 \times 10^{-6}$. The equilibrium constant $K_d$ is often calculated as $k_{off}/k_{on}$ and thus is typically measured in the range $10^{-5}$ to $10^{-12}$. Affinities measured in this manner correlate well with affinities measured in solution by fluorescence quench titration.

e) Screening for Antibodies with the Desired Properties

Techniques for generating antibodies have been described above. One may further select antibodies with certain biological characteristics, as desired.

The growth inhibitory effects of an anti-MRP3 antibody of the invention may be assessed by methods known in the art, e.g., using cells which express MRP3 either endogenously or following transfection with the MRP3 gene. For example, the tumor cell lines provided in the Examples Section below may treated with an anti-MRP3 monoclonal antibody of the invention at various concentrations for a few days (e.g., 2-7) days and stained with crystal violet or MTT or analyzed by some other colorimetric assay. Another method of measuring proliferation would be by comparing $^3$H-thymidine uptake by the cells treated in the presence or absence an anti-MRP3 antibody of the invention. After antibody treatment, the cells are harvested and the amount of radioactivity incorporated into the DNA quantitated in a scintillation counter. Appropriate positive controls include treatment of a selected cell line with a growth inhibitory antibody known to inhibit growth of that cell line. Growth inhibition of tumor cells in vivo can be determined in various ways known in the art. Preferably, the tumor cell is one that over-expresses MRP3. Preferably, the anti-MRP3 antibody will inhibit cell proliferation of a MRP3-expressing tumor cell in vitro or in vivo by about 25-100% compared to the untreated tumor cell, more preferably, by about 30-100%, and even more preferably by about 50-100% or 70-100%, at a certain antibody concentration, where the growth inhibition is determined 1-10 days after exposure of the tumor cells to the antibody. The antibody is growth inhibitory in vivo if administration of the anti-MRP3 antibody at a therapeutically effective amount/kg body weight results in reduction in tumor size or tumor cell proliferation within about 5 days to 3 months from the first administration of the antibody, preferably within about 5 to 30 days.

To select for antibodies which induce cell death, loss of membrane integrity as indicated by, e.g., propidium iodide (PI), trypan blue or 7AAD uptake may be assessed relative to control. A PI uptake assay can be performed in the absence of complement and immune effector cells. MRP3-expressing tumor cells are incubated with medium alone or medium containing of the appropriate monoclonal antibody. The cells are incubated for a 3 day time period. Following each treatment, cells are washed and aliquoted into 35 mm strainer-capped 12×75 tubes (1 ml per tube, 3 tubes per treatment group) for removal of cell clumps. Tubes then receive PI (10 .mu.g/ml). Samples may be analyzed using a FACSCAN™ flow cytometer and FACSCONVERT™ CellQuest software (Becton Dickinson). Those antibodies which induce cell death as determined by PI uptake may be selected as cell death-inducing antibodies.

To screen for antibodies which bind to an epitope on MRP3 bound by an antibody of interest, a routine cross-blocking assay such as that described in Antibodies, A Laboratory Manual, Cold Spring Harbor Laboratory, Ed Harlow and David Lane (1988), can be performed. This assay can be used to determine if a test antibody binds the same site or epitope as an anti-MRP3 antibody of the invention. Alternatively, or additionally, epitope mapping can be performed by methods known in the art. For example, the antibody sequence can be mutagenized such as by alanine scanning, to identify contact residues. The mutant antibody is initially tested for binding with polyclonal antibody to ensure proper folding. In a different method, peptides corresponding to different regions of MRP3 can be used in competition assays with the test antibodies or with a test antibody and an antibody with a characterized or known epitope.

f) Human Antibodies, Humanized Antibodies, Chimeric Antibodies and Diabodies

The antibodies described herein and/or the $V_H$ and/or $V_L$ domains therein can be used to make a variety of human, or humanized antibodies or diabodies.

1) Humanized (Chimeric) Antibodies

The antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see, e.g., U.S. Pat. No. 4,816,567; Morrison et al. (1984) Proc. Natl. Acad. Sci. 81: 6851 6855, etc.).

Humanized (chimeric) antibodies are immunoglobulin molecules comprising a human and non-human portion. More specifically, the antigen combining region (or variable region) of a humanized chimeric antibody is derived from a non-human source (e.g., murine) and the constant region of the chimeric antibody (which confers biological effector function to the immunoglobulin) is derived from a human source. The humanized chimeric antibody will have the antigen binding specificity of the non-human antibody molecule and the effector function conferred by the human antibody molecule. A large number of methods of generating chimeric antibodies are well known to those of skill in the art (see, e.g., U.S. Pat. Nos. 5,502,167, 5,500,362, 5,491,088, 5,482,856, 5,472,693, 5,354,847, 5,292,867, 5,231,026, 5,204,244, 5,202,238, 5,169,939, 5,081,235, 5,075,431, and 4,975,369, and PCT application WO 91/0996).

In general, the procedures used to produce chimeric antibodies consist of the following steps (the order of some steps may be interchanged): (a) identifying and cloning the correct gene segment encoding the antigen binding portion of the antibody molecule; this gene segment (known as the VDJ, variable, diversity and joining regions for heavy chains or VJ, variable, joining regions for light chains, or simply as the V or variable region or $V_H$ and $V_L$ regions) may be in either the cDNA or genomic form; (b) cloning the gene segments encoding the human constant region or desired part thereof;

(c) ligating the variable region to the constant region so that the complete chimeric antibody is encoded in a transcribable and translatable form; (d) ligating this construct into a vector containing a selectable marker and gene control regions such as promoters, enhancers and poly(A) addition signals; (e) amplifying this construct in a host cell (e.g., bacteria); (f) introducing the DNA into eukaryotic cells (transfection) most often mammalian lymphocytes; and culturing the host cell under conditions suitable for expression of the chimeric antibody.

Antibodies of several distinct antigen binding specificities have been manipulated by these protocols to produce chimeric proteins (e.g., anti-TNP: Boulianne et al. (1984) Nature, 312: 643; and anti-tumor antigens: Sahagan et al. (1986) J. Immunol., 137: 1066). Likewise several different effector functions have been achieved by linking new sequences to those encoding the antigen binding region. Some of these include enzymes (Neuberger et al. (1984) Nature 312: 604), immunoglobulin constant regions from another species and constant regions of another immunoglobulin chain (Sharon et al. (1984) Nature 309: 364; Tan et al., (1985) J. Immunol. 135: 3565 3567).

In one embodiment, a recombinant DNA vector is used to transfect a cell line that produces an anti-MRP3 antibody of this invention. The novel recombinant DNA vector contains a "replacement gene" to replace all or a portion of the gene encoding the immunoglobulin constant region in the cell line (e.g., a replacement gene may encode all or a portion of a constant region of a human immunoglobulin, a specific immunoglobulin class, or an enzyme, a toxin, a biologically active peptide, a growth factor, inhibitor, or a linker peptide to facilitate conjugation to a drug, toxin, or other molecule, etc.), and a "target sequence" that allows for targeted homologous recombination with immunoglobulin sequences within the antibody producing cell.

In another embodiment, a recombinant DNA vector is used to transfect a cell line that produces an antibody having a desired effector function, (e.g., a constant region of a human immunoglobulin) in which case, the replacement gene contained in the recombinant vector may encode all or a portion of a region of an anti MRP3 antibody of this invention and the target sequence contained in the recombinant vector allows for homologous recombination and targeted gene modification within the antibody producing cell. In either embodiment, when only a portion of the variable or constant region is replaced, the resulting chimeric antibody can define the same antigen and/or have the same effector function yet be altered or improved so that the chimeric antibody may demonstrate a greater antigen specificity, greater affinity binding constant, increased effector function, or increased secretion and production by the transfected antibody producing cell line, etc.

Regardless of the embodiment practiced, the processes of selection for integrated DNA (via a selectable marker), screening for chimeric antibody production, and cell cloning, can be used to obtain a clone of cells producing the chimeric antibody.

Thus, a piece of DNA that encodes a modification for a monoclonal antibody can be targeted directly to the site of the expressed immunoglobulin gene within a B-cell or hybridoma cell line. DNA constructs for any particular modification may be can to alter the protein product of any monoclonal cell line or hybridoma. The level of expression of chimeric antibody should be higher when the gene is at its natural chromosomal location rather than at a random position. Detailed methods for preparation of chimeric (humanized) antibodies can be found in U.S. Pat. No. 5,482,856.

2) Human Antibodies

In one embodiment, the antiMRP3 antibody of the present invention is a humanized antibody. In some embodiment, this invention provides for fully human anti-MRP3 antibodies. Human antibodies consist entirely of characteristically human polypeptide sequences. The human anti-MRP3-neutralizing antibodies of this invention can be produced in using a wide variety of methods (see, e.g., Larrick et al., U.S. Pat. No. 5,001,065, for review).

In one embodiment, fully human antibodies are produced using phage display methods. However, instead of utilizing a murine gene library, a human gene library is used. Methods of producing fully human gene libraries are well known to those of skill in the art (see, e.g., Vaughn et al. (1996) Nature Biotechnology, 14(3): 309 314, Marks et al. (1991) J. Mol. Biol., 222: 581 597, and PCT/US96/10287).

The human phage-display library is screened for members that bind the same epitope (e.g., are cross-reactive) with the anti-MRP3 antibodies described herein.

In another approach, the human antibodies are produced using trioma technology. The general approach for producing human antibodies by trioma technology has been described by Ostberg et al. (1983) Hybridoma 2: 361 367, Ostberg, U.S. Pat. No. 4,634,664, and Engelman et al., U.S. Pat. No. 4,634,666. The antibody-producing cell lines obtained by this method are called triomas because they are descended from three cells; two human and one mouse. Triomas have been found to produce antibody more stably than ordinary hybridomas made from human cells.

Preparation of trioma cells requires an initial fusion of a mouse myeloma cell line with unimmunized human peripheral B lymphocytes. This fusion generates a xenogenic hybrid cell containing both human and mouse chromosomes (see, Engelman, supra.). Xenogenic cells that have lost the capacity to secrete antibodies are selected. Preferably, a xenogenic cell is selected that is resistant to 8-azaguanine. Such cells are unable to propagate on hypoxanthine-aminopterin-thymidine (HAT) or azaserine-hypoxanthine (AH) media.

The capacity to secrete antibodies is conferred by a further fusion between the xenogenic cell and B-lymphocytes immunized against a MRP3 antigen. The B-lymphocytes are obtained from the spleen, blood or lymph nodes of human donor. If antibodies against a specific antigen or epitope are desired (e.g., the epitope(s) bound by the antibodies described herein), it is preferable to use that antigen or epitope thereof as the immunogen. Alternatively, B-lymphocytes are obtained from an unimmunized individual and stimulated with the desired antigen in vitro.

The immunized B-lymphocytes prepared by one of the above procedures are fused with a xenogenic hybrid cell by well known methods. For example, the cells are treated with 40 50% polyethylene glycol of MW 1000 4000, at about 37° C. for about 5-10 min. Cells are separated from the fusion mixture and propagated in media selective for the desired hybrids. When the xenogenic hybrid cell is resistant to 8-azaguanine, immortalized trioma cells are conveniently selected by successive passage of cells on HAT or AH medium. Other selective procedures are, of course, possible depending on the nature of the cells used in fusion. Clones secreting antibodies having the required binding specificity are identified by assaying the trioma culture medium for the ability to bind to the epitope(s) bound by the antibodies exemplified herein. Triomas producing human antibodies having the desired specificity are subcloned by the limiting dilution technique and grown in vitro in culture medium, or are injected into selected host animals and grown in vivo.

Although triomas are genetically stable they do not produce antibodies at very high levels. Expression levels can be increased by cloning antibody genes from the trioma into one or more expression vectors, and transforming the vector into a cell line such as the cell lines typically used for expression of recombinant or humanized immunoglobulins. As well as increasing yield of antibody, this strategy offers the additional advantage that immunoglobulins are obtained from a cell line that does not have a human component, and does not therefore need to be subjected to the especially extensive viral screening required for human cell lines.

The genes encoding the heavy and light chains of immunoglobulins secreted by trioma cell lines are cloned according to methods, including but not limited to, the polymerase chain reaction (PCR), known in the art (see, e.g., Sambrook et al., Molecular Cloning: A Laboratory Manual, 2nd ed., Cold Spring Harbor, N.Y., 1989; Berger & Kimmel, Methods in Enzymology, Vol. 152: Guide to Molecular Cloning Techniques, Academic Press, Inc., San Diego, Calif., 1987; Co et al. (1992) J. Immunol., 148: 1149). For example, genes encoding heavy and light chains are cloned from a trioma's genomic DNA or cDNA produced by reverse transcription of the trioma's RNA. Cloning is accomplished by conventional techniques including the use of PCR primers that hybridize to the sequences flanking or overlapping the genes, or segments of genes, to be cloned.

Typically, recombinant constructs comprise DNA segments encoding a complete human immunoglobulin heavy chain and/or a complete human immunoglobulin light chain of an immunoglobulin expressed by a trioma cell line. Alternatively, DNA segments encoding only a portion of the primary antibody genes are produced, which portions possess binding and/or effector activities. Other recombinant constructs contain segments of trioma cell line immunoglobulin genes fused to segments of other immunoglobulin genes, particularly segments of other human constant region sequences (heavy and/or light chain). Human constant region sequences can be selected from various reference sources, including but not limited to those listed in Kabat et al. (1987) Sequences of Proteins of Immunological Interest, U.S. Department of Health and Human Services.

3) Diabodies

In certain embodiments, this invention contemplates diabodies comprising one or more of the $V_H$ and $V_L$ domains described herein. The term "diabodies" refers to antibody fragments typically having two antigen-binding sites. The fragments typically comprise a heavy chain variable domain ($V_H$) connected to a light chain variable domain ($V_L$) in the same polypeptide chain ($V_H V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161, and Holliger et al. (1993) Proc. Natl. Acad. Sci. USA 90: 6444 6448.

III. Libraries and Vectors

In another embodiment, this invention provides libraries and vectors for practice of the methods described herein. The libraries include monovalent or polyvalent libraries, including diabody libraries and more preferably including multivalent single chain antibody libraries (e.g., scFv), (e.g., expressed by phage).

The libraries can take a number of forms. Thus, in one embodiment the library is a collection of cells containing members of the phage display library, while in another embodiment, the library consists of a collection of isolated phage, and in still another embodiment, the library consists of a library of nucleic acids encoding a polyvalent phage display library. In some embodiments, the nucleic acids can be phagemid vectors encoding the antibodies and ready for subcloning into a phage vector or the nucleic acids can be a collection of phagemid already carrying the subcloned antibody-encoding nucleic acids.

IV. Targeting

In some embodiments, the present invention provides anitMRP3 antibodies that can be used in therapeutic and/or diagnostic applications. For example, in the case of therapeutic applications, the antibodies can be used to inhibit a target involved in disease progression or by causing the cytotoxic death of target cells, which can be mediated by modulators of the immune response. Thus, e.g., such therapeutic antibodies can inhibit a signaling pathway or induce antibody-depedent cell-mediated cytotoxicty or complement-depedent cytotoxicty. Because MRP3 is upregulated on cancer cells, MRP3 provides a good cancer-specific marker that can act as a convenient target for specifically delivering various effectors (e.g., cytotoxins, labels, drugs or prodrugs, and the like) to cancer cells and/or to cells adjacent to cancer cells.

The anti-MRP3 antibodies of this invention thus provide effective targeting moieties (i.e. moieties that specifically bind to a target such as MRP3 displayed on a cell) that can, but need not, be transiently or permanently coupled to an effector (thereby forming a hybrid molecule or chimeric moiety) and used to direct that effector to a particular target cell (e.g., a cancer cell) expressing MRP3.

Further, the anti-MRP3 antibodies of the present invention can "internalize" (i.e., be taken up by (i.e., enter) a cell upon binding to MRP3 on the extracellular side of the cell. For therapeutic applications, internalization in vivo is contemplated. The number of antibody molecules internalized will be sufficient or adequate to kill a MRP3-expressing cell, especially a MRP3-expressing cancer cell. Depending on the potency of the antibody or antibody conjugate, in some instances, the uptake of a single antibody molecule into the cell is sufficient to kill the target cell to which the antibody binds. For example, certain toxins are highly potent in killing such that internalization of one molecule of the toxin conjugate to the antibody is sufficient to kill the tumor cell.

Whether an anti-MRP3 antibody internalizes upon binding MRP3 on a mammalian cell can be determined by various in vivo or in vitro assays including tests such as the those described herein. For example, to test internalization in vivo, the test antibody can be labeled and introduced into an animal known to have MRP3 expressed on the surface of certain cells, for example. The antibody can be radiolabeled or labeled with fluorescent or gold particles, for instance. Animals suitable for this assay include a mammal such as a NCR nude mouse that contains a human MRP3-expressing tumor transplant or xenograft, or a mouse into which cells transfected with human MRP3 have been introduced, or a transgenic mouse expressing the human MRP3 transgene. Appropriate controls include animals that did not receive the test antibody or that received an unrelated antibody, and animals that received an antibody to another antigen on the cells of interest, which antibody is known to be internalized upon binding to the antigen (e.g., HERCEPTIN™ which binds to Her2 expressed on the human breast tumor cell line, MCF-7). The antibody can be administered to the animal, e.g., by intravenous injection. At suitable time intervals, tissue sections of the animal can be prepared using known methods, and analyzed by light microscopy or electron microscopy, for internalization as well as the location of the internalized antibody in the cell.

For internalization in vitro, the cells can be incubated in tissue culture dishes in the presence or absence of the relevant antibodies added to the culture media and processed for microscopic analysis at desired time points. The presence of an internalized, labeled antibody in the cells can be directly visualized by microscopy or by autoradiography if radiolabeled antibody is used. Alternatively, in a quantitative biochemical assay, a population of cells comprising MRP3-expressing cells can be contacted in vitro or in vivo with a radiolabeled test antibody and the cells (if contacted in vivo, cells can then be isolated after a suitable amount of time) can be treated with a protease or subjected to an acid wash to remove uninternalized antibody on the cell surface. The cells can be ground up and the amount of protease resistant, radioactive counts per minute (cpm) associated with each batch of cells can be measured by passing the homogenate through a scintillation counter. Based on the known specific activity of the radiolabeled antibody, the number of antibody molecules internalized per cell can be deduced from the scintillation counts of the ground-up cells. Cells can be "contacted" with antibody in vitro preferably in solution form such as by adding the cells to the cell culture media in the culture dish or flask and mixing the antibody well with the media to ensure uniform exposure of the cells to the antibody. Instead of adding to the culture media, the cells can be contacted with the test antibody in an isotonic solution such as PBS in a test tube for the desired time period. In vivo, the cells are contacted with antibody by any suitable method of administering the test antibody such as the methods of administration described below when administered to a patient.

The faster the rate of internalization of the antibody upon binding to the MRP3 expressing cell in vivo, the faster the desired killing or growth inhibitory effect on the target MRP3-expressing cell can be achieved, e.g., by a cytotoxic immunoconjugate. Preferably, the kinetics of internalization of the anti-MRP3 antibodies are such that they favor rapid killing of the MRP3-expressing target cell. Therefore, it is desirable that the anti-MRP3 antibody exhibit a rapid rate of internalization preferably, within about 48 hours from administration of the antibody in vivo, illustratively, within about 24, about 12 hours, about 8 hours, about 6 hours, about 4 hours, about 2 hours, about 1 hour, about 45 minutes, about 30 minutes, about 20 minutes, and about 15 minutes. The antibody will preferably be internalized into the cell within a few hours upon binding to MRP3 on the cell surface, preferably within 1 hour, even more preferably within 15-30 minutes.

a) Therapeutics

The antibodies of the present invention can be used for the treatment and/or prevention of cancer. Therapeutic benefits may be realized by the administration of a therapeutically effective amount of a pharmaceutical composition comprising at least one, two, three or more anti-MRP3 antibodies, or fragments thereof. The pharmaceutical composition can also be combined with other therapies to provide combined therapeutically effective amounts.

Examples of types of cancers contemplated by the present invention include, but are not limited to, glioma, gliosarcoma, anaplastic astrocytoma, medulloblastoma, lung cancer, small cell lung carcinoma, cervical carcinoma, colon cancer, rectal cancer, chordoma, throat cancer, Kaposi's sarcoma, lymphangiosarcoma, lymphangioendotheliosarcoma, colorectal cancer, endometrium cancer, ovarian cancer, breast cancer, pancreatic cancer, prostate cancer, renal cell carcinoma, hepatic carcinoma, bile duct carcinoma, choriocarcinoma, seminoma, testicular tumor, Wilms' tumor, Ewing's tumor, bladder carcinoma, angiosarcoma, endotheliosarcoma, adenocarcinoma, sweat gland carcinoma, sebaceous gland sarcoma, papillary sarcoma, papillary adenosarcoma, cystadenosarcoma, bronchogenic carcinoma, medullar carcinoma, mastocytoma, mesotheliorma, synovioma, melanoma, leiomyosarcoma, rhabdomyosarcoma, neuroblastoma, retinoblastoma, oligodentroglioma, acoustic neuroma, hemangioblastoma, meningioma, pinealoma, ependymoma, craniopharyngioma, epithelial carcinoma, embryonic carcinoma, squamous cell carcinoma, base cell carcinoma, fibrosarcoma, myxoma, myxosarcoma, liposarcoma, chondrosarcoma, osteogenic sarcoma, leukemia, lymphoma, myeloma, and metastatic lesions secondary therefrom.

In one embodiment, the cancer comprises a multidrug-resistant cancer cell.

Although understanding the mechanism of action is not necessary to the practice of the present anti-MRP3 antibody treatment, without being held to a particular theory, the methods may operate to induce cell-mediated cytotoxicity, complement-mediated lysis, and/or apoptosis. The cytotoxic methods may also be based upon antibody-induced cell signaling (direct signaling), or mimicking or altering signal transduction pathways (indirect signaling).

In other embodiments, the present invention provides novel combinations of at least two different antibodies capable of binding to MRP3, wherein the antibodies are separately capable of treating and/or preventing the expression of MRP3 expressing tumor cells. In one embodiment, these antibody combinations will exhibit greater (synergistic) cytotoxic activity than would be expected for the sum of the individual antibodies if administered separately at the same overall antibody concentration. For example, at least two of these antibodies will recognize distinct MRP3 epitopes and will not cross react with the other. However, the present inventors do not want to be restricted thereby, but rather intend to embrace any combination of anti-MRP3 antibodies.

In some embodiments, the antibody combinations will comprise PepI-58 scFv and PepII-89 scFV, PepI-58 scFv and PepIII-23 scFv, PepI-58 scFv and PepIV-17 scFv, PepII-58 scFv and PepIII-23 sc Fv, PepII-58 scFv and PepIV-17 scFv, or PepIII-23 scFv and PepIV-17 scFv. In one embodiment, the antibody combinations will comprise PepI-58 scFV, PepII-89 scFV, and PepIII-23, PepI-58 scFv, PepII-89 scFv, and PepIV-17 scFv, PepI-58 scFv, PepIII-23 scFv, and PepIV-17 scFv, or PepII-58 scFv, PepIII-23 scFv, and PepIV-17 scFv. In another embodiment, the antibody combinations will comprise PepI-58 scFv, PepII-89 scFv, PepIII-23, and PepIV-17 scFv. In other embodiments, the antibody combination comprises PepI-25 scFv.

The MRP3 antibodies which are suitable for use in such combinations may include monoclonal antibodies capable of binding to MRP3, recombinant MRP3 antibodies, chimeric MRP3 antibodies which comprise constant and variable domains derived from different species, such as murine-human chimeric antibodies (wherein the constant domain is human and the variable domain is of murine origin), humanized forms of such antibodies, single chain antibodies capable of binding to the MRP3 protein, and fragments or analogues of MRP3 monoclonal antibodies which are capable of binding to the MRP3 protein, and which antibody combinations exhibit synergistic cytotoxic activity.

In one embodiment, the present invention provides a method for treating cancer in an animal or patient in need of such treatment, wherein the method comprises administering to the animal or patient a therapeutically effective amount of a pharmaceutical composition comprising at least one anti- MRP3 antibody (e.g., PepI-58 scFv, PepI-25 scFv, PepII-89 scFv, PepIII-23 scFV, PepIV-17 scFv), wherein the composition is effective to induce, or specifically induce, cell-mediated cytotoxicity of at least a portion of the cancer cells. As used herein, "cell-mediated cytotoxicity or destruction" includes ADCC (antibody-dependent, cell-mediated cytotoxicity) and NK (natural killer) cell killing.

In some embodiments, the composition is effective to induce, or specifically induce, complement-mediated lysis of at least a portion of cancer cells. As used herein, "complement-mediated or complement-dependent lysis or cytotoxicity" means the process by which the complement-dependent coagulation cascade is activated, multi-component complexes are assembled, ultimately generating a lytic complex that has direct lytic action, causing cell permeabilization. Anti-MRP3 antibodies for use in inducing complement-mediated lysis will generally include the Fc portion of the antibody.

The complement-based mechanisms by which the present invention may operate further include "complement-activated ADCC". In this embodiment, the composition is effective to induce complement-activated ADCC of at least a portion of the cancer cells. "Complement-activated ADCC" is used to refer to the process by which complement, not an antibody Fc portion per se, holds a multi-component complex together and in which cells such as neutrophils lyse the target cell.

In other embodiments, the pharmaceutical composition is effective to induce, or specifically induce, apoptosis in at least a portion of the cancer cells. The pharmaceutical composition induces apoptosis in least a portion of the cancer cells, as opposed to normal cells. As used herein, "induces apoptosis" means induces the process of programmed cell death that, during the initial stages, maintains the integrity of the cell membrane, yet transmits the death-inducing signals into the cell. This is opposed to the mechanisms of cell necrosis, during which the cell membrane loses its integrity and becomes leaky at the onset of the process.

The pharmaceutical composition will generally comprise at least one anti-MRP3 antibody (e.g., PepI-58 scFv, PepI-25 scFv, PepII-89 scFv, PepIII-23 scFV, PepIV-17 scFv) dissolved or dispersed in a pharmaceutically acceptable carrier or aqueous medium. Combined therapeutics are also contemplated, and the same type of underlying pharmaceutical compositions may be employed for both single and combined medicaments. Single or multiple administrations of the compositions may be administered depending on the dosage and frequency as required and tolerated by the patient. In any event, the composition should provide a sufficient quantity of the proteins of this invention to effectively treat the patient.

It will be appreciated by one of skill in the art that there are some regions that are not heavily vascularized or that are protected by cells joined by tight junctions and/or active transport mechanisms which reduce or prevent the entry of macromolecules present in the blood stream. Thus, for example, systemic administration of therapeutics to treat gliomas, or other brain cancers, is constrained by the blood-brain barrier which resists the entry of macromolecules into the subarachnoid space. One of skill in the art will appreciate that in these instances, the therapeutic compositions of this invention can be administered directly to the tumor site. Thus, for example, brain tumors (e.g., gliomas) can be treated by administering the therapeutic composition directly to the tumor site (e.g., through a surgically implanted catheter). Where the fluid delivery through the catheter is pressurized, small molecules (e.g., the therapeutic molecules of this invention) will typically infiltrate as much as two to three centimeters beyond the tumor margin.

Alternatively, the therapeutic composition can be placed at the target site in a slow release formulation. Such formulations can include, for example, a biocompatible sponge or other inert or resorbable matrix material impregnated with the therapeutic composition, slow dissolving time release capsules or microcapsules, and the like.

Typically the catheter or time release formulation will be placed at the tumor site as part of a surgical procedure. Thus, for example, where major tumor mass is surgically removed, the perfusing catheter or time release formulation can be emplaced at the tumor site as an adjunct therapy. Of course, surgical removal of the tumor mass may be undesired, not required, or impossible, in which case, the delivery of the therapeutic compositions of this invention may comprise the primary therapeutic modality.

In some embodiments, the animals or patients to be treated by the present invention are further subjected to surgery or radiotherapy, or are provided with a therapeutically effective amount of at least one other anti-cancer agent. The "at least one other anti-cancer agent" in this context means "at least one anti-cancer agent in addition to the anti-MRP3 antibody" (e.g., anti-MRP1 antibody). The "at least one anti-cancer agent" may thus be considered to be "at least a second anti-cancer agent", where the anti-MRP3 antibody is a first anti-cancer agent. However, this is purely a matter of semantics, and the practical meaning will be clear to those of ordinary skill in the art.

The at least one other anti-cancer agent may be administered to the animal or patient substantially simultaneously with the anti-MRP3 antibody, such as from a single pharmaceutical composition, or from two pharmaceutical compositions administered closely together. Alternatively, the at least a first anti-cancer agent may be administered to the animal or patient at a time sequential to the administration of the at least a first anti-MRP3 antibody, or antigen-binding fragment thereof. "At a time sequential", as used herein, means "staggered", such that the at least a first anti-cancer agent is administered to the animal or patient at a time distinct to the administration of the at least a first anti-MRP3 antibody. Generally, the two agents are administered at times effectively spaced apart to allow the two agents to exert their respective therapeutic effects, i.e., they are administered at "biologically effective time intervals."

b) Diagnostic

The anti-MRP3 antibodies of the present invention can be used in screening or diagnostic applications. The anti-MRP3 antibodies according to the present invention are valuable for in vitro and in vivo diagnostic purposes. For example, the anti-MRP3 can be used in western blots, immunoprecipitation, enzyme-linked immunosorbent assay (ELISA), fluorescence Activated Cell Sorting (FACS), indirect immunofluoresence microscopy, immunohistochemistry (IHC), etc. In one embodiment, the present invention provides an immunological method for determining a cell expressing MRP3, the method comprising contacting the cell with at least one anti-MRP3 antibody, the antibody is as disclosed herein.

In one embodiment, the present invention provides a diagnostic method for in vitro or in vivo assaying for MRP3, wherein the method comprises providing a diagnostically effective amount of an isolated antibody that selectively binds an epitope located in an extracellular portion of MRP3, wherein, optionally, the antibody is in a carrier. In another embodiment, a diagnostic method for in vitro or in vivo assaying for MRP3 is provided, wherein the method comprises providing a diagnostically effective amount of at least one single chain antibody selected from the group consisting of PepI-58 scFv, PepI-25 scFv, PepII-89 scFv, PepIII-23 scFV, and PepIV-17 scFv.

For example, the anti-MRP3 antibodies can be used as diagnostic agents for assaying for the detection of MRP3 expressing cells. The MRP3 binding antibodies of the present invention should be particularly suitable as diagnostic agents given their binding affinity to MRP3. Essentially, a sample suspected of containing MRP3 expressing cells (e.g., cancer cells) will be incubated with the subject antibody or antibodies for a sufficient time to permit immune reactions to occur. Those skilled in the art will recognize that there are many variations in these basic procedures. These variations include, for example, RIA, ELISA, precipitation, agglutination, complement fixation and immunofluorescence. Preferably, the subject antibodies will be labelled to permit the detection of antibody-MRP3 immunocomplexes. Further, the anti-MRP3 antibodies of the present invention are also useful for detection and quantitation of MRP3 in vitro, to kill and eliminate MRP3-expressing cells from a population of mixed cells as a step in the purification of other cells.

For example, a sample suspected of containing MRP3 expressing cancer cells will be incubated with the subject antibody or antibodies disclosed herein for a sufficient time to permit immune reactions to occur. Those skilled in the art will recognize that there are many variations in these basic procedures. These variations include, for example, RIA, ELISA, precipitation, agglutination, complement fixation and immunofluorescence. Preferably, the subject antibodies will be labelled to permit the detection of antibody-MRP3 immunocomplexes.

The labels that are used in making labeled versions of the antibodies include moieties that may be detected directly, such as radiolabels and fluorochromes, as well as moieties, such as enzymes, that must be reacted or derivatized to be detected. Radiolabels include, but are not limited to $^{99}Tc$, $^{203}Pb$, $^{67}Ga$, $^{68}Ga$, $^{72}As$, $^{111}In$, $^{113m}In$, $^{97}Ru$, $^{62}Cu$, $^{641}Cu$, $^{52}Fe$, $^{52m}Mn$, $^{51}Cr$, $^{186}Re$, $^{188}Re$, $^{77}As$, $^{90}Y$, $^{67}Cu$, $^{169}Er$, $^{121}Sn$, $^{127}Te$, $^{142}Pr$, $^{143}Pr$, $^{198}Au$, $^{199}Au$, $^{161}Tb$, $^{109}Pd$, $^{165}Dy$, $^{149}Pm$, $^{151}Pm$, $^{153}Sm$, $^{157}Gd$, $^{159}Gd$, $^{166}Ho$, $^{172}Tm$, $^{169}Yb$, $^{177}Lu$, $^{105}Rh$, and $^{111}Ag$. The radiolabel can be detected by any of the currently available counting procedures.

The enzyme label can be detected by any of the currently utilized calorimetric, spectrophotometric, fluorospectrophotometric or gasometric techniques. The enzyme is combined with the antibody with bridging molecules such as carbodiimides, periodate, diisocyanates, glutaraldehyde and the like. Many enzymes which can be used in these procedures are known and can be utilized. Examples are peroxidase, alkaline phosphatase, .beta.-glucuronidase, β-D-glucosidase, urease, glucose oxidase plus peroxidase, galactose oxidase plus peroxidase and acid phosphatase. Fluorescent materials which may be used include, for example, fluorescein and its derivatives, rhodamine and its derivatives, auramine, dansyl, umbelliferone, luciferia, 2,3-dihydrophthalazinediones, horseradish peroxidase, alkaline phosphatase, lysozyme, and glucose-6-phosphate dehydrogenase. The antibodies may be tagged with such labels by known methods. For instance, coupling agents such as aldehydes, carbodiimides, dimaleimide, imidates, succinimides, bis-diazotized benzadine and the like may be used to tag the antibodies with the above-described fluorescent, chemiluminescent, and enzyme labels. Various labeling techniques are described in Morrison, Methods in Enzymology, (1974), 32B, 103; Syvanen et al., J. Biol. Chem., (1973), 284, 3762; and Bolton and Hunter, Biochem J., (1973), 133, 529.

The antibodies and labeled antibodies may be used in a variety of immunoimaging or immunoassay procedures to detect the presence of cancer in a patient or monitor the status of such cancer in a patient already diagnosed to have it. When used to monitor the status of a cancer, a quantitative immunoassay procedure must be used. If such monitoring assays are carried out periodically and the results compared, a determination may be made regarding whether the patient's tumor burden has increased or decreased. Common assay techniques that may be used include direct and indirect assays. If the sample includes cancer cells, the labeled antibody will bind to those cells. After washing the tissue or cells to remove unbound labeled antibody, the tissue sample is read for the presence of labeled immune complexes. In indirect assays the tissue or cell sample is incubated with unlabeled monoclonal antibody. The sample is then treated with a labeled antibody against the monoclonal antibody (e.g., a labeled antimurine antibody), washed, and read for the presence of ternary complexes.

For diagnostic use the antibodies can be distributed in kit form. These kits can comprise: the antibody in labeled or unlabeled form in suitable containers, reagents for the incubations for an indirect assay, and substrates or derivatizing agents depending on the nature of the label. MRP-3 controls and instructions may also be included.

In one embodiment, the present invention provides a diagnostic composition suitable for in vitro or in vivo assaying for MRP3, wherein the composition comprises a diagnostically effective amount of an isolated antibody that selectively binds an epitope located in an extracellular portion of MRP3. Optionally, the antibody is in a carrier. In other embodiments, the diagnostic composition comprises a diagnostically effective amount of at least one single chain antibody selected from the group consisting of PepI-58 scFv, PepI-25 scFv, PepII-89 scFv, PepIII-23 scFV, and PepIV-17 scFv.

c) Combined Diagnostic/Therapeutic

In some embodiments, the cancer cells or tumor of the animal or patient to be treated may be first imaged. Generally this is achieved by administering to the animal or patient a diagnostically effective amount of a pharmaceutical composition comprising a detectably-labeled anti-MRP3 antibody that selectively binds an epitope located on the extracellular portion of MRP3. The invention thus further provides compositions for use in, and methods of, distinguishing between tumor and normal cells.

Examples of labels that may be used to prepare the detectably-labeled anti-MRP3 antibody include, without limitation, an X-ray detectable compound (e.g., $^{99}Tc$, $^{203}Pb$, $^{67}Ga$, $^{68}Ga$, $^{72}As$, $^{111}In$, $^{113m}In$, $^{97}Ru$, $^{62}Cu$, $^{641}Cu$, $^{52}Fe$, $^{52m}Mn$, $^{51}Cr$, $^{186}Re$, $^{188}Re$, $^{77}As$, $^{90}Y$, $^{67}Cu$, $^{169}Er$, $^{121}Sn$, $^{127}Te$, $^{142}Pr$, $^{143}Pr$, $^{198}Au$, $^{199}Au$, $^{161}Tb$, $^{109}Pd$, $^{165}Dy$, $^{149}Pm$, $^{151}Pm$, $^{153}Sm$, $^{157}Gd$, $^{159}Gd$, $^{166}Ho$, $^{172}Tm$, $^{169}Yb$, $^{177}Lu$, $^{105}Rh$, and $^{111}Ag$), a nuclear magnetic spin-resonance isotope (e.g., cobalt (II), copper (II), chromium (III), dysprosium (III), erbium (III), gadolinium (III), holmium (III), iron (II), iron (III), manganese (II), neodymium (III), nickel (II), samarium (III), terbium (III), vanadium (II) or ytterbium (III)), rhodamine, or fluorescein. The diagnostic label or agent can be operatively attached to the antibody.

Pre-imaging before tumor treatment may be carried out by: (a) administering to the animal or patient a diagnostically effective amount of a pharmaceutical composition comprising a detectably-labeled anti-MRP3 antibody that comprises a diagnostic agent operatively attached to the antibody, wherein the antibody selectively binds to an epitope located in an extracellular portion of MRP3; and (b) detecting the detectably-labeled anti-MRP3 antibody bound to the epitope thereby obtaining an image of the cancer cells or mass.

Cancer treatment may also be carried out by (a) forming an image of the cancer by administering to an animal or patient having cancerous cells a diagnostically effective amount of a detectably-labeled anti-MRP3 antibody that comprises a diagnostic agent operatively attached to the antibody, wherein the antibody selectively binds to an epitope located in an extracellular portion of MRP3 thereby forming a detectable image of the tumor vasculature; and, (b) administering to the animal or patient a therapeutically effective amount of at least one anti-MRP3 antibody that selectively binds to an epitope located in an extracellular portion of MRP3 thereby destroying the cancer cells or mass.

Imaging and treatment formulations or medicaments are thus provided, which generally comprise: (a) a first pharmaceutical composition comprising a diagnostically effective amount of at least one detectably-labeled anti-MRP3 antibody that comprises a diagnostic agent operatively attached to the antibody, wherein the antibody selectively binds to an epitope located in an extracellular portion of MRP3; (b) at least one anti-MRP3 antibody that selectively binds to an epitope located in an extracellular portion of MRP3, or both.

In the diagnostic imaging embodiments of the invention, it is recognized that the diagnostic component (e.g., the detectably-labeled anti-MRP3 antibody) may itself have a therapeutic effect. Whilst this would not be excluded from the invention, the amounts of the detectably-labeled constructs to be administered would generally be chosen as "diagnostically effective amounts", which are typically lower than the amounts required for therapeutic benefit.

The above imaging and treatment formulations or medicaments may also further comprise one or more anti-cancer agents. That is, the present invention encompasses imaging and combination treatment formulations and medicaments that generally comprise (a) diagnostically effective amounts of detectably-labeled anti-MRP3 antibodies, or fragments thereof; (b) therapeutically effective amounts anti-MRP3 antibodies, or fragments thereof; and (c) therapeutically effective amounts of at least one anti-cancer agent(s).

d) Hybrid Molecules

Since MRP3 is upregulated in cancer cells, it can be exploited as target for the efficient and specific delivery of an effector (e.g., an effector molecule such as a cytotoxin, a radiolabel, etc.) to various cancer cells (e.g., isolated cells, metastatic cells, solid tumor cells, etc.). MRP3 need not exist solely on cancer cells to provide an effective target. Differential expression of MRP3 on cancer cells, as compared to healthy cells, is sufficient to provide significant and useful targeting advantage, i.e. resulting in preferential delivery of the effector moiety to the target (e.g., cancer) cell.

1) Effectors

The effector molecule refers to a molecule or group of molecules that is to be specifically transported to the target cell (e.g., a cell expressing MRP3). The effector molecule typically has a characteristic activity that is to be delivered to the target cell. Effector molecules include, but are not limited to cytotoxins, labels, radionuclides, ligands, antibodies, drugs, liposomes, epitope tags, and the like.

In some embodiments, the effector is a detectable label, with preferred detectable labels including radionuclides. Among the radionuclides and labels useful in the radionuclide-chelator-(e.g., biotin) conjugates of the present invention, gamma-emitters, positron-emitters, x-ray emitters and fluorescence-emitters are suitable for localization, diagnosis and/or staging, and/or therapy, while beta and alpha-emitters and electron and neutron-capturing agents, such as boron and uranium, also can be used for therapy.

The detectable labels can be used in conjunction with an external detector and/or an internal detector and provide a means of effectively localizing and/or visualizing cells bearing MRP3 antigen (e.g., cancer cells, solid tumors, etc.). Such detection/visualization can be useful in various contexts including, but not limited to pre-operative and intraoperative settings. Thus, in some embodiments this invention relates to a method of intraoperatively detecting and locating tissues having MRP3 markers in the body of a mammal. These methods typically involve administering to the mammal a composition comprising, in a quantity sufficient for detection by a detector (e.g., a gamma detecting probe), an anti-MRP3 labeled with a detectable label (e.g., anti-MRP3 antibodies of this invention labeled with a radioisotope, e.g., $^{161}$Tb, $^{123}$I, $^{125}$I, and the like), and after allowing the active substance to be taken up by the target tissue, and preferably after blood clearance of the label, subjecting the mammal to a radioimmunodetection technique in the relevant area of the body, e.g., by using a gamma detecting probe.

The label-bound anti-MRP3 antibody can be used in the technique of radioguided surgery, wherein relevant tissues in the body of a subject can be detected and located intraoperatively by means of a detector, e.g., a gamma detecting probe. The medical care provider can, intraoperatively, use this probe to find the tissues in which uptake of the compound labeled with a radioisotope, that is, e.g., a low-energy gamma photon emitter, has taken place.

In addition to detectable labels, preferred effectors include cytotoxins (e.g., *Pseudomonas* exotoxin, gelonin, ricin, abrin, *Diphtheria* toxin, and the like), immunomodulators (e.g., IL2, TNF-α, GM-CSF, B 7.1, H60), or cytotoxic drugs or prodrugs, in which case the hybrid molecule may act as a potent cell-killing agent specifically targeting the cytotoxin to cells bearing the MRP3 target.

Further examples of effectors include, but are not limited to, granzyme, luciferase, vascular endothelial growth factor, b-lactamase, Tr-apo-1, Ang II, TAT, alkylating agents, daunomycin, adriamycin, chlorambucil, anti-metabolites (e.g., methotrexate), modaccin A chain, alpha-sarcin, *Aleurites fordii* proteins, dianthin proteins, *Phytolacca americana* proteins (PAPI, PAPII, and PAP-S), *Momordica charantia* inhibitor, curcin, crotin, *Sapaonaria officinalis* inhibitor, mitogellin, restrictocoin, phenomycin and enomycin.

In still other embodiments, the effector can include a liposome encapsulating a drug (e.g., an anti-cancer drug such as doxirubicin, vinblastine, taxol, etc.), an antigen that stimulates recognition of the bound cell by components of the immune system, and antibody that specifically binds immune system components and directs them to the MRP3 bearing cell, and the like.

i) Imaging Compositions

In certain embodiments, the hybrid molecules of this invention can be used to direct detectable labels to a tumor site. This can facilitate tumor detection and/or localization. In some embodiments, the effector component of the hybrid molecule is a "radioopaque" label, e.g., a label that can be easily visualized using x-rays. Radioopaque materials are well known to those of skill in the art. The most common radiopaque materials include iodide, bromide or barium salts. Other radiopaque materials are also known and include, but are not limited to organic bismuth derivatives (see, e.g., U.S. Pat. No. 5,939,045), radiopaque polyurethanes (see U.S. Pat. No. 5,346,981, organobismuth composites (see, e.g., U.S. Pat. No. 5,256,334), radiopaque barium polymer complexes (see, e.g., U.S. Pat. No. 4,866,132), and the like.

The anti-MRP3 antibody(s) can be coupled directly to the radiopaque moiety or they can be attached to a "package" (e.g., a chelate, a liposome, a polymer microbead, etc.) carrying or containing the radiopaque material as described below.

In addition to radioopaque labels, other labels are also suitable for use in this invention. Detectable labels suitable for use as the effector molecule component of the hybrid molecules of this invention include any composition detectable by spectroscopic, photochemical, biochemical, immunochemical, electrical, optical or chemical means. Useful labels in the present invention include magnetic beads (e.g., DYNABEADS™), fluorescent dyes (e.g., fluorescein isothiocyanate, texas red, rhodamine, green fluorescent protein, and the like), radiolabels (e.g., $^{3}H$, $^{125}I$, $^{35}S$, $^{14}C$, or $^{32}P$), enzymes (e.g., horse radish peroxidase, alkaline phosphatase and others commonly used in an ELISA), and colorimetric labels such as colloidal gold or colored glass or plastic (e.g., polystyrene, polypropylene, latex, etc.) beads.

Various preferred radiolabels include, but are not limited to $^{99}Tc$, $^{203}Pb$, $^{67}Ga$, $^{68}Ga$, $^{72}As$, $^{111}In$, $^{113m}In$, $^{97}Ru$, $^{62}Cu$, $^{64}Cu$, $^{52}Fe$, $^{52m}Mn$, $^{51}Cr$, $^{186}Re$, $^{188}Re$, $^{77}As$, $^{90}Y$, $^{67}Cu$, $^{169}Er$, $^{121}Sn$, $^{127}Te$, $^{142}Pr$, $^{143}Pr$, $^{198}Au$, $^{199}Au$, $^{161}Tb$, $^{109}Pd$, $^{165}Dy$, $^{149}Pm$, $^{151}Pm$, $^{153}Sm$, $^{157}Gd$, $^{159}Gd$, $^{166}Ho$, $^{172}Tm$, $^{169}Yb$, $^{177}Lu$, $^{105}Rh$, and $^{111}Ag$.

Means of detecting such labels are well known to those of skill in the art. Thus, for example, radiolabels may be detected using photographic film, scintillation detectors, and the like. Fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

ii) Radiosensitizers

In another embodiment, the effector can be a radiosensitizer that enhances the cytotoxic effect of ionizing radiation (e.g., such as might be produced by $^{60}Co$ or an x-ray source) on a cell. Numerous radiosensitizing agents are known and include, but are not limited to benzoporphyrin derivative compounds (see, e.g., U.S. Pat. No. 5,945,439), 1,2,4-benzotriazine oxides (see, e.g., U.S. Pat. No. 5,849,738), compounds containing certain diamines (see, e.g., U.S. Pat. No. 5,700,825), BCNT (see, e.g., U.S. Pat. No. 5,872,107), radiosensitizing nitrobenzoic acid amide derivatives (see, e.g., U.S. Pat. No. 4,474,814), various heterocyclic derivatives (see, e.g., U.S. Pat. No. 5,064,849), platinum complexes (see, e.g., U.S. Pat. No. 4,921,963), and the like.

iii) Ligands

The effector molecule may also be a ligand, an epitope tag, or an antibody. Particularly preferred ligand and antibodies are those that bind to surface markers on immune cells. Hybrid molecules utilizing such antibodies as effector molecules act as bifunctional linkers establishing an association between the immune cells bearing binding partner for the ligand or antibody and the tumor cells expressing the MRP3 antigen.

iv) Chelates

Many of the pharmaceuticals and/or radiolabels described herein are preferably provided as a chelate, particularly where a pre-targeting strategy is utilized. The chelating molecule is typically coupled to a molecule (e.g., biotin, avidin, streptavidin, etc.) that specifically binds an epitope tag attached to the anti-MRP3 antibody.

Chelating groups are well known to those of skill in the art. In certain embodiments, chelating groups are derived from ethylene diamine tetra-acetic acid (EDTA), diethylene triamine penta-acetic acid (DTPA), cyclohexyl 1,2-diamine tetra-acetic acid (CDTA), ethyleneglycol-O, O'-bis(2-aminoethyl)-N,N,N',N'-tetra-acetic acid (EGTA), N,N-bis(hydroxybenzyl)-ethylenediamine-N,N'-diacetic acid (HBED), triethylene tetramine hexa-acetic acid (TTHA), 1,4,7,10-tetraazacyclododecane-N,N',N'',N'''-tetra-acetic acid (DOTA), hydroxyethyldiamine triacetic acid (HEDTA), 1,4,8,11-tetraazacyclotetradecane-N,N', N',N'''-tetra-acetic acid (TETA), substituted DTPA, substituted EDTA, and the like.

Examples of certain preferred chelators include unsubstituted or, substituted 2-iminothiolanes and 2-iminothiacyclohexanes, in particular 2-imino-4-mercaptomethylthiolane.

One chelating agent, 1,4,7,10-tetraazacyclododecane-N, N,N',N'''-tetraacetic acid (DOTA), is of particular interest because of its ability to chelate a number of diagnostically and therapeutically important metals, such as radionuclides and radiolabels.

Conjugates of DOTA and proteins such as antibodies have been described. For example, U.S. Pat. No. 5,428,156 teaches a method for conjugating DOTA to antibodies and antibody fragments. To make these conjugates, one carboxylic acid group of DOTA is converted to an active ester which can react with an amine or sulfhydryl group on the antibody or antibody fragment. Lewis et al. (1994) Bioconjugate Chem. 5: 565 576, describes a similar method wherein one carboxyl group of DOTA is converted to an active ester, and the activated DOTA is mixed with an antibody, linking the antibody to DOTA via the epsilon-amino group of a lysine residue of the antibody, thereby converting one carboxyl group of DOTA to an amide moiety.

Alternatively, the chelating agent can be coupled, directly or through a linker, to an epitope tag or to a moiety that binds an epitope tag. Conjugates of DOTA and biotin have been described (see, e.g., Su (1995) J. Nucl. Med., 36 (5 Suppl): 154P, which discloses the linkage of DOTA to biotin via available amino side chain biotin derivatives such as DOTA-LC-biotin or DOTA-benzyl-4-(6-amino-caproamide)-biotin). Yau et al., WO 95/15335, disclose a method of producing nitro-benzyl-DOTA compounds that can be conjugated to biotin. The method comprises a cyclization reaction via transient projection of a hydroxy group; tosylation of an amine; deprotection of the transiently protected hydroxy group; tosylation of the deprotected hydroxy group; and intramolecular tosylate cyclization. Wu et al. (1992) Nucl. Med. Biol., 19(2): 239 244 discloses a synthesis of macrocylic chelating agents for radiolabeling proteins with $^{111}In$ and $^{90}Y$. Wu et al. makes a labeled DOTA-biotin conjugate to study the stability and biodistribution of conjugates with avidin, a model protein for studies. This conjugate was made using a biotin hydrazide which contained a free amino group to react with an in situ generated activated DOTA derivative.

v) Cytotoxins

Particularly preferred cytotoxins include *Pseudomonas* exotoxins, *Diphtheria* toxins, ricin, and abrin. *Pseudomonas* exotoxin and *Dipthteria* toxin are most preferred.

*Pseudomonas* exotoxin A (PE) is an extremely active monomeric protein (molecular weight 66 kD), secreted by *Pseudomonas aeruginosa*, which inhibits protein synthesis in eukaryotic cells through the inactivation of elongation factor 2 (EF-2) by catalyzing its ADP-ribosylation (catalyzing the transfer of the ADP ribosyl moiety of oxidized NAD onto EF-2).

The toxin contains three structural domains that act in concert to cause cytotoxicity. Domain Ia (amino acids 1-252) mediates cell binding. Domain II (amino acids 253-364) is responsible for translocation into the cytosol and domain III (amino acids 400-613) mediates ADP ribosylation of elongation factor 2, which inactivates the protein and causes cell death. The function of domain Ib (amino acids 365-399) remains undefined, although a large part of it, amino acids 365-380, can be deleted without loss of cytotoxicity. See Siegall et al. (1989) J. Biol. Chem. 264: 14256 14261.

Where the targeting molecule (e.g., anti-MRP3) is fused to PE, a preferred PE molecule is one in which domain Ia (amino acids 1 through 252) is deleted and amino acids 365 to 380 have been deleted from domain Ib. However all of domain Ib and a portion of domain II (amino acids 350 to 394) can be deleted, particularly if the deleted sequences are replaced with a linking peptide such as disclosed by SEQ ID NO:7.

In addition, the PE molecules can be further modified using site-directed mutagenesis or other techniques known in the art, to alter the molecule for a particular desired application. Means to alter the PE molecule in a manner that does not substantially affect the functional advantages provided by the PE molecules described here can also be used and such resulting molecules are intended to be covered herein.

For maximum cytotoxic properties of a preferred PE molecule, several modifications to the molecule are recommended. An appropriate carboxyl terminal sequence to the recombinant molecule is preferred to translocate the molecule into the cytosol of target cells. Amino acid sequences which have been found to be effective include, REDLK (as in native PE), REDL, RDEL, or KDEL, repeats of those, or other sequences that function to maintain or recycle proteins into the endoplasmic reticulum, referred to here as "endoplasmic retention sequences". See, for example, Chaudhary et al. (1991) Proc. Natl. Acad. Sci. USA 87:308 312 and Seetharam et al, J. Biol. Chem. 266: 17376 17381. Preferred forms of PE comprise the PE molecule designated PE38QQR. (Debinski et al. Bioconj. Chem., 5: 40 (1994)), and PE4E (see, e.g., Chaudhary et al. (1995) J. Biol. Chem., 265:16306).

Methods of cloning genes encoding PE fused to various ligands are well known to those of skill in the art (see, e.g., Siegall et al. (1989) FASEB J., 3: 2647 2652; and Chaudhary et al. (1987) Proc. Natl. Acad. Sci. USA, 84: 4538 4542).

Like PE, *Diphtheria* toxin (DT) kills cells by ADP-ribosylating elongation factor 2 thereby inhibiting protein synthesis. *Diphtheria* toxin, however, is divided into two chains, A and B, linked by a disulfide bridge. In contrast to PE, chain B of DT, which is on the carboxyl end, is responsible for receptor binding and chain A, which is present on the amino end, contains the enzymatic activity (Uchida et al. (1972) Science, 175: 901 903; Uchida et al. (1973) J. Biol. Chem., 248: 3838 3844).

In a preferred embodiment, the targeting molecule-*Diphtheria* toxin fusion proteins of this invention have the native receptor-binding domain removed by truncation of the *Diphtheria* toxin B chain. Particularly preferred is DT388, a DT in which the carboxyl terminal sequence beginning at residue 389 is removed. Chaudhary et al. (1991) Bioch. Biophys. Res. Comm., 180: 545 551. Like the PE chimeric cytotoxins, the DT molecules may be chemically conjugated to the MRP3 antibody, but, in some embodiments, the targeting molecule will be fused to the *Diphtheria* toxin by recombinant means (see, e.g., Williams et al. (1990) J. Biol. Chem. 265: 11885 11889).

vi) Other Therapeutic Moieties

Other suitable effector molecules include pharmacological agents or encapsulation systems containing various pharmacological agents. Thus, the targeting molecule of the hybrid molecule may be attached directly to a drug that is to be delivered directly to the tumor. Such drugs are well known to those of skill in the art and include, but are not limited to, doxirubicin, vinblastine, genistein, an antisense molecule, and the like.

Alternatively, the effector molecule may be an encapsulation system, such as a viral capsid, a liposome, or micelle that contains a therapeutic composition such as a drug, a nucleic acid (e.g., an antisense nucleic acid), or another therapeutic moiety that is preferably shielded from direct exposure to the circulatory system. Means of preparing liposomes attached to antibodies are well known to those of skill in the art. See, for example, U.S. Pat. No. 4,957,735, Connor et al. (1985) Pham. Ther., 28: 341 365.

2) Targeting and "Pretargeting" Protocols

In some embodiments, the effector (e.g., cytotoxins, labels, epitope tags, therapeutic agents, etc.) can be targeted to target sites, such as neoplastic cells, solid tumors, metastatic cells and the like, using targeting or "pretargeting" protocols.

Targeting protocols utilize a hybrid molecule comprising a primary targeting component (e.g., an anti MRP3 antibody) that specifically binds the desired target (e.g., a cancer cell). The primary targeting component can be attached to an effector that bears the desired activity (e.g., cytotoxicity, radioactivity, etc.) that is to be delivered to the target site. Binding of the hybrid molecule to the target effectively delivers the effector having the desired activity. Thus, as described heren, the anti-MRP3 antibodies of this invention can be utilized in a "pretargeting" strategy (resulting in formation of a chimeric moiety at the target site after administration of the effector moiety) or in a "targeting" strategy where the anti-MRP3 antibody is coupled to an effector molecule prior to use to provide a hybrid molecule.

In pretargeting protocols, a hybrid molecule is utilized comprising a primary targeting component (e.g., an anti MRP3 antibody) that specifically binds the desired target (e.g., a cancer cell). The primary targeting component is attached to an effector that provides a binding site that is available for binding by a subsequently administered second targeting species. Once sufficient accretion of the primary targeting species (the hybrid molecule) is achieved, a second targeting species comprising, e.g., (i) a diagnostic or therapeutic agent and (ii) a second targeting moiety, that recognizes the available binding site of the primary targeting species, is administered.

An illustrative example of a pretargeting protocol is the biotin-avidin system for administering a cytotoxic radionuclide to a tumor. In a typical procedure, an antibody (e.g., a monoclonal anti-MRP3 antibody) or antibody fragment (e.g., anti-MRP3 scFV) targeted against a tumor-associated antigen (e.g., MRP3) is conjugated to avidin and administered to a patient who has a tumor recognized by the antibody. Then the therapeutic agent, e.g., a chelated radionuclide covalently bound to biotin, is administered. The radionuclide, via its attached biotin is taken up by the antibody-avidin conjugate pretargeted at the tumor. Examples of pre-targeting biotin/avidin protocols are described, for example, in Goodwin et al., U.S. Pat. No. 4,863,713; Goodwin et al. (1988) J. Nucl. Med. 29: 226; Hnatowich et al. (1987) J. Nucl. Med. 28: 1294; Oehr et al. (1988) J. Nucl. Med. 29: 728; Klibanov et al. (1988) J. Nucl. Med. 29: 1951; Sinitsyn et al. (1989) J. Nucl. Med. 30: 66; Kalofonos et al. (1990) J. Nucl. Med. 31: 1791; Schechter et al. (1991) Int. J. Cancer 48:167; Paganelli et al. (1991) Cancer Res. 51: 5960; Paganelli et al. (1991) Nucl. Med. Commun. 12: 211; Stickney et al. (1991) Cancer Res. 51: 6650; and Yuan et al. (1991) Cancer Res. 51:3119.

Three-step pretargeting protocols in which a clearing agent is administered after the first targeting composition has localized at the target site also have been described. The clearing agent binds and removes circulating primary conjugate which is not bound at the target site, and prevents circulating primary targeting species (antibody-avidin or conjugate, for example) from interfering with the targeting of active agent species (biotin-active agent conjugate) at the target site by competing for the binding sites on the active agent-conjugate. When antibody-avidin is used as the primary targeting moiety, excess circulating conjugate can be cleared by injecting a biotinylated polymer such as biotinylated human serum albumin. This type of agent forms a high molecular weight species with the circulating avidin-antibody conjugate which is quickly recognized by the hepatobiliary system and deposited primarily in the liver.

Examples of these protocols are disclosed, e.g., in PCT Application No. WO 93/25240; Paganelli et al. (1991) Nucl. Med. Comm., 12: 211 234; Oehr et al. (1988) J. Nucl. Med., 29: 728 729; Kalofonos et al. (1990) J. Nucl. Med., 31: 1791 1796; Goodwin et al. (1988) J. Nucl. Med., 29: 226 234. Improved pretargeting protocols using the biotin-avidin system are disclosed, e.g., in U.S. Pat. Nos. 5,525,338, 5,482, 698, and the like.

3) Attachment of the Targeting Molecule to the Effector Molecule

One of skill will appreciate that the MRP3 antibodies of this invention and the effector molecules may be joined together in any order. Thus, where the targeting molecule is a polypeptide, the effector molecule may be joined to either the amino or carboxy termini of the targeting molecule. The targeting molecule may also be joined to an internal region of the effector molecule, or conversely, the effector molecule may be joined to an internal location of the targeting molecule, as long as the attachment does not interfere with the respective activities of the molecules.

The targeting molecule and the effector molecule may be attached by any of a number of means well known to those of skill in the art. Typically the effector molecule is conjugated, either directly or through a linker (spacer), to the targeting molecule. However, where both the effector molecule and the targeting molecule are polypeptides it is preferable to recombinantly express the hybrid molecule as a single-chain fusion protein.

i) Conjugation of the Effector Molecule to the Targeting Molecule

In one embodiment, the targeting molecule (e.g., anti-MRP3 scFV) is chemically conjugated to the effector molecule (e.g., a cytotoxin, a label, a ligand, or a drug or liposome). Means of chemically conjugating molecules are well known to those of skill.

The procedure for attaching an agent to an antibody or other polypeptide targeting molecule will vary according to the chemical structure of the agent. Polypeptides typically contain variety of functional groups; e.g., carboxylic acid (COOH) or free amine (—NH$_2$) groups, which are available for reaction with a suitable functional group on an effector molecule to bind the effector thereto.

Alternatively, the targeting molecule and/or effector molecule may be derivatized to expose or attach additional reactive functional groups. The derivatization may involve attachment of any of a number of linker molecules such as those available from Pierce Chemical Company, Rockford Ill.

A "linker", as used herein, is a molecule that is used to join the targeting molecule to the effector molecule. The linker is capable of forming covalent bonds to both the targeting molecule and to the effector molecule. Suitable linkers are well known to those of skill in the art and include, but are not limited to, straight or branched-chain carbon linkers, heterocyclic carbon linkers, or peptide linkers. Where the targeting molecule and the effector molecule are polypeptides, the linkers may be joined to the constituent amino acids through their side groups (e.g., through a disulfide linkage to cysteine). However, in a preferred embodiment, the linkers will be joined to the alpha carbon amino and carboxyl groups of the terminal amino acids.

A bifunctional linker having one functional group reactive with a group on a particular agent, and another group reactive with an antibody, may be used to form the desired immunoconjugate. Alternatively, derivatization may involve chemical treatment of the targeting molecule, e.g., glycol cleavage of the sugar moiety of a the glycoprotein antibody with periodate to generate free aldehyde groups. The free aldehyde groups on the antibody may be reacted with free amine or hydrazine groups on an agent to bind the agent thereto. (See U.S. Pat. No. 4,671,958). Procedures for generation of free sulfhydryl groups on polypeptide, such as antibodies or antibody fragments, are also known (See U.S. Pat. No. 4,659, 839).

Many procedure and linker molecules for attachment of various compounds including radionuclide metal chelates, toxins and drugs to proteins such as antibodies are known (see, e.g., European Patent Application No. 188,256; U.S. Pat. Nos. 4,671,958, 4,659,839, 4,414,148, 4,699,784; 4,680, 338; 4,569,789; and 4,589,071; and Borlinghaus et al. (1987) Cancer Res. 47: 4071 4075). In particular, production of various immunotoxins is well-known within the art and can be found, for example in "Monoclonal Antibody-Toxin Conjugates: Aiming the Magic Bullet," Thorpe et al., Monoclonal Antibodies in Clinical Medicine, Academic Press, pp. 168 190 (1982), Waldmann (1991) Science, 252: 1657, U.S. Pat. Nos. 4,545,985 and 4,894,443.

In some circumstances, it is desirable to free the effector molecule from the targeting molecule when the hybrid molecule has reached its target site. Therefore, chimeric conjugates comprising linkages which are cleavable in the vicinity of the target site may be used when the effector is to be released at the target site. Cleaving of the linkage to release the agent from the antibody may be prompted by enzymatic activity or conditions to which the immunoconjugate is subjected either inside the target cell or in the vicinity of the target site. When the target site is a tumor, a linker which is cleavable under conditions present at the tumor site (e.g., when exposed to tumor-associated enzymes or acidic pH) may be used.

A number of different cleavable linkers are known to those of skill in the art. See U.S. Pat. Nos. 4,618,492; 4,542,225, and 4,625,014. The mechanisms for release of an agent from these linker groups include, for example, irradiation of a photolabile bond and acid-catalyzed hydrolysis. U.S. Pat. No. 4,671,958, for example, includes a description of immunoconjugates comprising linkers which are cleaved at the target site in vivo by the proteolytic enzymes of the patient's complement system. In view of the large number of methods that have been reported for attaching a variety of radiodiagnostic compounds, radiotherapeutic compounds, drugs, toxins, and other agents to antibodies one skilled in the art will be able to determine a suitable method for attaching a given agent to an antibody or other polypeptide.

ii) Conjugation of Chelates

In some embodiments, the effector comprises a chelate that is attached to an antibody or to an epitope tag. The MRP3 antibody bears a corresponding epitope tag or antibody so that simple contacting of the MRP3 antibody to the chelate results in attachment of the antibody with the effector. The combining step can be performed before the moiety is used (targeting strategy) or the target tissue can be bound to the anti-MRP3 antibody before the chelate is delivered. Methods of producing chelates suitable for coupling to various targeting moieties are well known to those of skill in the art (see, e.g., U.S. Pat. Nos. 6,190,923, 6,187,285, 6,183,721, 6,177,562, 6,159,445, 6,153,775, 6,149,890, 6,143,276, 6,143,274, 6,139,819, 6,132,764, 6,123,923, 6,123,921, 6,120,768, 6,120,751, 6,117,412, 6,106,866, 6,096,290, 6,093,382, 6,090,800, 6,090,408, 6,088,613, 6,077,499, 6,075,010, 6,071,494, 6,071,490, 6,060,040, 6,056,939, 6,051,207, 6,048,979, 6,045,821, 6,045,775, 6,030,840, 6,028,066, 6,022,966, 6,022,523, 6,022,522, 6,017,522, 6,015,897, 6,010,682, 6,010,681, 6,004,533, and 6,001,329).

iii) Production of Fusion Proteins

Where the MRP3 targeting molecule and/or the effector molecule is relatively short (i.e., less than about 50 amino acids) they may be synthesized using standard chemical peptide synthesis techniques. Where both molecules are relatively short the hybrid molecule may be synthesized as a single contiguous polypeptide. Alternatively the targeting molecule and the effector molecule may be synthesized separately and then fused by condensation of the amino terminus of one molecule with the carboxyl terminus of the other molecule thereby forming a peptide bond. Alternatively, the targeting and effector molecules may each be condensed with one end of a peptide spacer molecule thereby forming a contiguous fusion protein.

Solid phase synthesis in which the C-terminal amino acid of the sequence is attached to an insoluble support followed by sequential addition of the remaining amino acids in the sequence is the preferred method for the chemical synthesis of the polypeptides of this invention. Techniques for solid phase synthesis are described by Barany and Merrifield, Solid-Phase Peptide Synthesis; pp. 3 284 in The Peptides: Analysis, Synthesis, Biology. Vol. 2: Special Methods in Peptide Synthesis, Part A., Merrifield, et al. J. Am. Chem. Soc., 85: 2149 2156 (1963), and Stewart et al., Solid Phase Peptide Synthesis, 2nd ed. Pierce Chem. Co., Rockford, Ill. (1984).

In a preferred embodiment, the chimeric fusion proteins of the present invention are synthesized using recombinant DNA methodology. Generally this involves creating a DNA sequence that encodes the fusion protein, placing the DNA in an expression cassette under the control of a particular promoter, expressing the protein in a host, isolating the expressed protein and, if required, renaturing the protein.

DNA encoding the fusion proteins of this invention may be prepared by any suitable method, including, for example, cloning and restriction of appropriate sequences or direct chemical synthesis by methods such as the phosphotriester method of Narang et al. (1979) Meth. Enzymol. 68: 90 99; the phosphodiester method of Brown et al. (1979) Meth. Enzymol. 68: 109 151; the diethylphosphoramidite method of Beaucage et al. (1981) Tetra. Lett., 22: 1859 1862; and the solid support method of U.S. Pat. No. 4,458,066.

Chemical synthesis produces a single stranded oligonucleotide. This may be converted into double stranded DNA by hybridization with a complementary sequence, or by polymerization with a DNA polymerase using the single strand as a template. One of skill would recognize that while chemical synthesis of DNA is limited to sequences of about 100 bases, longer sequences can be obtained by the ligation of shorter sequences.

Alternatively, subsequences can be cloned and the appropriate subsequences cleaved using appropriate restriction enzymes. The fragments can then be ligated to produce the desired DNA sequence.

In one embodiment, DNA encoding fusion proteins of the present invention may be cloned using DNA amplification methods such as polymerase chain reaction (PCR). Thus, for example, the nucleic acid encoding an anti-MRP3 antibody is PCR amplified, using a sense primer containing the restriction site for NdeI and an antisense primer containing the restriction site for Hind III. This produces a nucleic acid encoding the anti-MRP3 sequence and having terminal restriction sites. A PE38QQR fragment may be cut out of the plasmid pWDMH4 38QQR or plasmid pSGC242FdN1 described by Debinski et al. (1994) Int. J. Cancer, 58: 744 748. Ligation of the anti-MRP3 and PE38QQR sequences and insertion into a vector produces a vector encoding anti-MRP3 joined to the amino terminus of PE38QQR (position 253 of PE). The two molecules are joined by a three amino acid junction consisting of glutamic acid, alanine, and phenylalanine introduced by the restriction site.

While the two molecules are preferably essentially directly joined together, one of skill will appreciate that the molecules may be separated by a peptide spacer consisting of one or more amino acids. Generally the spacer will have no specific biological activity other than to join the proteins or to preserve some minimum distance or other spatial relationship between them. However, the constituent amino acids of the spacer may be selected to influence some property of the molecule such as the folding, net charge, or hydrophobicity.

The nucleic acid sequences encoding the fusion proteins may be expressed in a variety of host cells, including *E. coli*, other bacterial hosts, yeast, and various higher eukaryotic cells such as the COS, CHO and HeLa cells lines and myeloma cell lines. The recombinant protein gene will be operably linked to appropriate expression control sequences for each host. For *E. coli* this includes a promoter such as the T7, trp, or lambda promoters, a ribosome binding site and preferably a transcription termination signal. For eukaryotic cells, the control sequences will include a promoter and preferably an enhancer derived from immunoglobulin genes, SV40, cytomegalovirus, etc., and a polyadenylation sequence, and may include splice donor and acceptor sequences.

The plasmids of the invention can be transferred into the chosen host cell by well-known methods such as calcium chloride transformation for *E. coli* and calcium phosphate treatment or electroporation for mammalian cells. Cells transformed by the plasmids can be selected by resistance to antibiotics conferred by genes contained on the plasmids, such as the amp, gpt, neo and hyg genes.

Once expressed, the recombinant fusion proteins can be purified according to standard procedures of the art, including ammonium sulfate precipitation, affinity columns, column chromatography, gel electrophoresis and the like (see, generally, R. Scopes (1982) Protein Purification, Springer-Verlag, N.Y.; Deutscher (1990) Methods in Enzymology Vol. 182: Guide to Protein Purification., Academic Press, Inc. N.Y.). Substantially pure compositions of at least about 90 to 95% homogeneity are preferred, and 98 to 99% or more homogeneity are most preferred for pharmaceutical uses. Once purified, partially or to homogeneity as desired, the polypeptides may then be used therapeutically.

One of skill in the art would recognize that after chemical synthesis, biological expression, or purification, the MRP3 targeted fusion protein may possess a conformation substantially different than the native conformations of the constituent polypeptides. In this case, it may be necessary to denature and reduce the polypeptide and then to cause the polypeptide to re-fold into the preferred conformation. Methods of reducing and denaturing proteins and inducing re-folding are well known to those of skill in the art (See, Debinski et al. (1993) J. Biol. Chem., 268: 14065 14070; Kreitman and Pastan (1993) Bioconjug. Chem., 4: 581 585; and Buchner, et al. (1992) Anal. Biochem., 205: 263 270).

One of skill would recognize that modifications can be made to the MRP3 targeted fusion proteins without diminishing their biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids placed on either terminus to create conveniently located restriction sites or termination codons.

V) Pharmaceutical Compositions

The anti-MRP3 antibodies, and/or chelates, and/or hybrid molecules (i.e., active ingredients) of this invention are useful for parenteral, topical, oral, or local administration (e.g., injected into a tumor site), aerosol administration, or transdermal administration, for prophylactic, but principally for therapeutic treatment. The pharmaceutical compositions can be administered in a variety of unit dosage forms depending upon the method of administration. For example, unit dosage forms suitable for oral administration include powder, tablets, pills, capsules and lozenges. It is recognized that the fusion proteins and pharmaceutical compositions of this invention, when administered orally, must be protected from digestion. This is typically accomplished either by complexing the protein with a composition to render it resistant to acidic and enzymatic hydrolysis or by packaging the protein in an appropriately resistant carrier such as a liposome. Means of protecting proteins from digestion are well known in the art.

The pharmaceutical compositions of this invention are particularly useful for parenteral administration, such as intravenous administration or administration into a body cavity or lumen of an organ. The compositions for administration will commonly comprise a solution of the anti-MRP3 antibodies, and/or chelates, and/or hybrid molecules dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of the anti-MRP3 antibodies, and/or chelates, and/or hybrid molecules in these formulations can vary widely, and will be selected primarily based on fluid volumes, viscosities, body weight and the like in accordance with the particular mode of administration selected and the patient's needs.

For example, for parenteral administration the subject antibodies or antibody combinations may be formulated in a unit dosage injectable form (solution, suspension, emulsion) in association with a pharmaceutically acceptable parenteral vehicle. Examples of such vehicles are water, saline, Ringer's solution, dextrose solution, and 5% human serum albumin. Nonaqueous vehicles such as mixed oils and ethyl oleate may also be used. Liposomes may also be used as carriers. The vehicles may contain minor amounts of additives that enhance isotonicity and chemical stability, e.g., buffers and preservatives.

The anti-MRP3 antibodies, and/or chelates, and/or hybrid molecules of the present invention can be formulated for parenteral administration, e.g., formulated for injection via the intravenous, intramuscular, sub-cutaneous, transdermal, or other such routes, including peristaltic administration and direct instillation into a tumor or disease site (intracavity administration). The preparation of an aqueous composition that contains the anti-MRP3 antibodies, and/or chelates, and/or hybrid molecules as an active ingredient will be known to those of skill in the art. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form should be sterile and fluid to the extent that syringability exists. It should be stable under the conditions of manufacture and storage and should be preserved against the contaminating action of microorganisms, such as bacteria and fungi.

The compositions can be formulated into a sterile aqueous composition in a neutral or salt form. Solutions of the anti-MRP3 antibodies, and/or chelates, and/or hybrid molecules as free base or pharmacologically acceptable salts can be prepared in water suitably mixed with a surfactant, such as hydroxypropylcellulose. Pharmaceutically acceptable salts, include the acid addition salts (formed with the free amino groups of the protein), and those that are formed with inorganic acids such as, for example, hydrochloric or phosphoric acids, or such organic acids as acetic, trifluoroacetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Suitable carriers include solvents and dispersion media containing, for example, water, ethanol, polyol (for example, glycerol, propylene glycol, and liquid polyethylene glycol, and the like), suitable mixtures thereof, and vegetable oils. In many cases, it will be preferable to include isotonic agents, for example, sugars or sodium chloride. The proper fluidity can be maintained, for example, by the use of a coating, such as lecithin, by the maintenance of the required particle size in the case of dispersion and/or by the use of surfactants.

Under ordinary conditions of storage and use, all such preparations can contain a preservative to prevent the growth of microorganisms. The prevention of the action of microorganisms can be brought about by various antibacterial and antifungal agents, for example, parabens, chlorobutanol, phenol, sorbic acid, thimerosal, and the like. Prolonged absorption of the injectable compositions can be brought about by the use in the compositions of agents delaying absorption, for example, aluminum monostearate and gelatin.

Prior to or upon formulation, the anti-MRP3 antibodies, and/or chelates, and/or hybrid molecules can be extensively dialyzed to remove undesired small molecular weight molecules, and/or lyophilized for more ready formulation into a desired vehicle, where appropriate. Sterile injectable solutions are prepared by incorporating the active ingredients in the required amount in the appropriate solvent with various of the other ingredients enumerated above, as desired, followed by filtered sterilization. Generally, dispersions are prepared by incorporating the various sterilized active ingredients into a sterile vehicle that contains the basic dispersion medium and the required other ingredients from those enumerated above.

In the case of sterile powders for the preparation of sterile injectable solutions, the preferred methods of preparation are vacuum-drying and freeze-drying techniques that yield a powder of the active ingredients, plus any additional desired ingredient from a previously sterile-filtered solution thereof.

Suitable pharmaceutical compositions in accordance with the invention will generally include an amount of the anti-MRP3 antibodies, and/or chelates, and/or hybrid molecules admixed with an acceptable pharmaceutical diluent or excipient, such as a sterile aqueous solution, to give a range of final concentrations, depending on the intended use. The techniques of preparation are generally well known in the art as exemplified by Remington's Pharmaceutical Sciences, 16th Ed. Mack Publishing Company, 1980, incorporated herein by reference. It should be appreciated that endotoxin contamination should be kept minimally at a safe level, for example, less that 0.5 ng/mg protein.

Upon formulation, anti-MRP3 antibodies, and/or chelates, and/or hybrid molecules solutions will be administered in a manner compatible with the dosage formulation and in such amount as is therapeutically effective. Formulations are easily administered in a variety of dosage forms, such as the type of injectable solutions described above, but other pharmaceutically acceptable forms are also contemplated, e.g., tablets, pills, capsules or other solids for oral administration, suppositories, pessaries, nasal solutions or sprays, aerosols, inhalants, liposomal forms and the like. Pharmaceutical "slow release" capsules or compositions may also be used. Slow release formulations are generally designed to give a constant drug level over an extended period and may be used to deliver anti-MRP3 antibodies, and/or chelates, and/or hybrid molecules in accordance with the present invention.

In some embodiments, liposomes and/or nanoparticles may also be employed with the active ingredients. The formation and use of liposomes is generally known to those of skill in the art. Liposomes can be formed from phospholipids that are dispersed in an aqueous medium and spontaneously form multilamellar concentric bilayer vesicles (also termed multilamellar vesicles (MLVs). MLVs can generally have diameters of from 25 nm to 4 µm. Sonication of MLVs results in the formation of small unilamellar vesicles (SUVs) with diameters in the range of 200 to 500 angstrom, containing an aqueous solution in the core. Phospholipids can form a variety of structures other than liposomes when dispersed in water, depending on the molar ratio of lipid to water. At low ratios the liposome is the preferred structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

Without being held to a particular theory, it is believed that liposomes can interact with cells at least via four different mechanisms: Endocytosis by phagocytic cells of the reticuloendothelial system such as macrophages and neutrophils; adsorption to the cell surface, either by nonspecific weak hydrophobic or electrostatic forces, or by specific interactions with cell-surface components; fusion with the plasma cell membrane by insertion of the lipid bilayer of the liposome into the plasma membrane, with simultaneous release of liposomal contents into the cytoplasm; and by transfer of liposomal lipids to cellular or subcellular membranes, or vice versa, without any association of the liposome contents. Varying the liposome formulation can alter which mechanism is operative, although more than one may operate at the same time.

Nanocapsules can generally entrap compounds in a stable and reproducible way. To avoid side effects due to intracellular polymeric overloading, such ultrafine particles (sized around 0.1 µm) should be designed using polymers able to be degraded in vivo. Biodegradable polyalkyl-cyanoacrylate nanoparticles that meet these requirements are contemplated for use in the present invention, and such particles may be are easily made.

VI. Kits

The present invention also provides therapeutic kits comprising anti-MRP3 antibodies, and/or chelates, and/or hybrid molecules for use in the present treatment methods. Such kits will generally contain, in suitable container means, a pharmaceutically acceptable formulation of at least one anti-MRP3 antibody. The kits may also contain other pharmaceutically acceptable formulations, either for diagnosis/imaging or combined therapy. For example, such kits may contain any one or more of a range of chemotherapeutic or radiotherapeutic drugs; anti-angiogenic agents; anti-tumor cell antibodies; and/or anti-tumor vasculature or anti-tumor stroma immunotoxins or coaguligands.

The kits may have a single container (container means) that contains the anti-MRP3 antibody, with or without any additional components, or they may have distinct containers for each desired agent. Where combined therapeutics are provided, a single solution may be pre-mixed, either in a molar equivalent combination, or with one component in excess of the other. Alternatively, each of the anti-MRP3 antibodies, and/or chelates, and/or hybrid molecules and other anti-cancer agent components of the kit may be maintained separately within distinct containers prior to administration to a patient.

When the components of the kit are provided in one or more liquid solutions, the liquid solution is preferably an aqueous solution, with a sterile aqueous solution being particularly preferred. However, the components of the kit may be provided as dried powder(s). When reagents or components are provided as a dry powder, the powder can be reconstituted by the addition of a suitable solvent. It is envisioned that the solvent may also be provided in another container.

The containers of the kit will generally include at least one vial, test tube, flask, bottle, syringe or other container means, into which the anti-MRP3 antibodies, and/or chelates, and/or hybrid molecules, and any other desired agent, may be placed and, preferably, suitably aliquoted. Where separate components are included, the kit will also generally contain a second vial or other container into which these are placed, enabling the administration of separated designed doses. The kits may also comprise a second/third container means for containing a sterile, pharmaceutically acceptable buffer or other diluent.

The kits may also contain a means by which to administer the anti-MRP3 antibodies, and/or chelates, and/or hybrid molecules to an animal or patient, e.g., one or more needles or syringes, or even an eye dropper, pipette, or other such like apparatus, from which the formulation may be injected into the animal or applied to a diseased area of the body. The kits of the present invention will also typically include a means for containing the vials, or such like, and other component, in close confinement for commercial sale, such as, e.g., injection or blow-molded plastic containers into which the desired vials and other apparatus are placed and retained.

Where a radioactive, or other, effector is used as a diagnostic and/or therapeutic agent, it is a frequently impossible to put the ready-for-use composition at the disposal of the user, because of the often poor shelf life of the radiolabelled compound and/or the short half-life of the radionuclide used. In such cases the user can carry out the labeling reaction with the radionuclide in the clinical hospital, physician's office, or laboratory. For this purpose, or other purposes, the various reaction ingredients can then be offered to the user in the form of a kit. The kit is preferably designed so that the manipulations necessary to perform the desired reaction should be as simple as possible to enable the user to prepare from the kit the desired composition by using the facilities that are at his disposal. Therefore the invention also relates to a kit for preparing a composition according to this invention.

Such a kit according to the present invention preferably comprises an anti-MRP3 antibodies, and/or chelates, and/or hybrid molecules of this invention. The anti-MRP3 antibodies, and/or chelates, and/or hybrid molecules can be provided, if desired, with inert pharmaceutically acceptable carrier and/or formulating agents and/or adjuvants is/are added. In addition, the kit optionally includes a solution of a salt or chelate of a suitable radionuclide (or other active agent), and (iii) instructions for use with a prescription for administering and/or reacting the ingredients present in the kit.

The kit to be supplied to the user may also comprise the ingredient(s) defined above, together with instructions for use, whereas the solution of a salt or chelate of the radionuclide, defined sub (ii) above, which solution has a limited shelf life, may be put to the disposal of the user separately.

The kit can optionally, additionally comprise a reducing agent and/or, if desired, a chelator, and/or instructions for use of the composition and/or a prescription for reacting the ingredients of the kit to form the desired product(s). If desired, the ingredients of the kit may be combined, provided they are compatible.

In certain embodiments, the complex-forming reaction with the anti-MRP3 antibody can simply be produced by combining the components in a neutral medium and causing them to react. For that purpose the effector may be presented to the anti-MRP3 antibody in the form of a chelate.

When kit constituent(s) are used as component(s) for pharmaceutical administration (e.g., as an injection liquid) they should be sterile. When the constituent(s) are provided in a dry state, the user should preferably use a sterile physiological saline solution as a solvent. If desired, the constituent(s) may be stabilized in the conventional manner with suitable stabilizers, for example, ascorbic acid, gentisic acid or salts of these acids, or they may comprise other auxiliary agents, for example, fillers, such as glucose, lactose, mannitol, and the like.

While the instructional materials, when present, typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

Example 1

Selection of MRP3-Derived Peptides for Use in Panning Phage Display Library

Hydrophobicity analysis of the MRP3 amino acid sequence indicated an organization of putative transmembrane domains resembling that suggested for MRP1 (FIG. 1). These proteins probably span the membrane 17 times, with the $NH_2$ terminus being extracellular.

Figure 2:
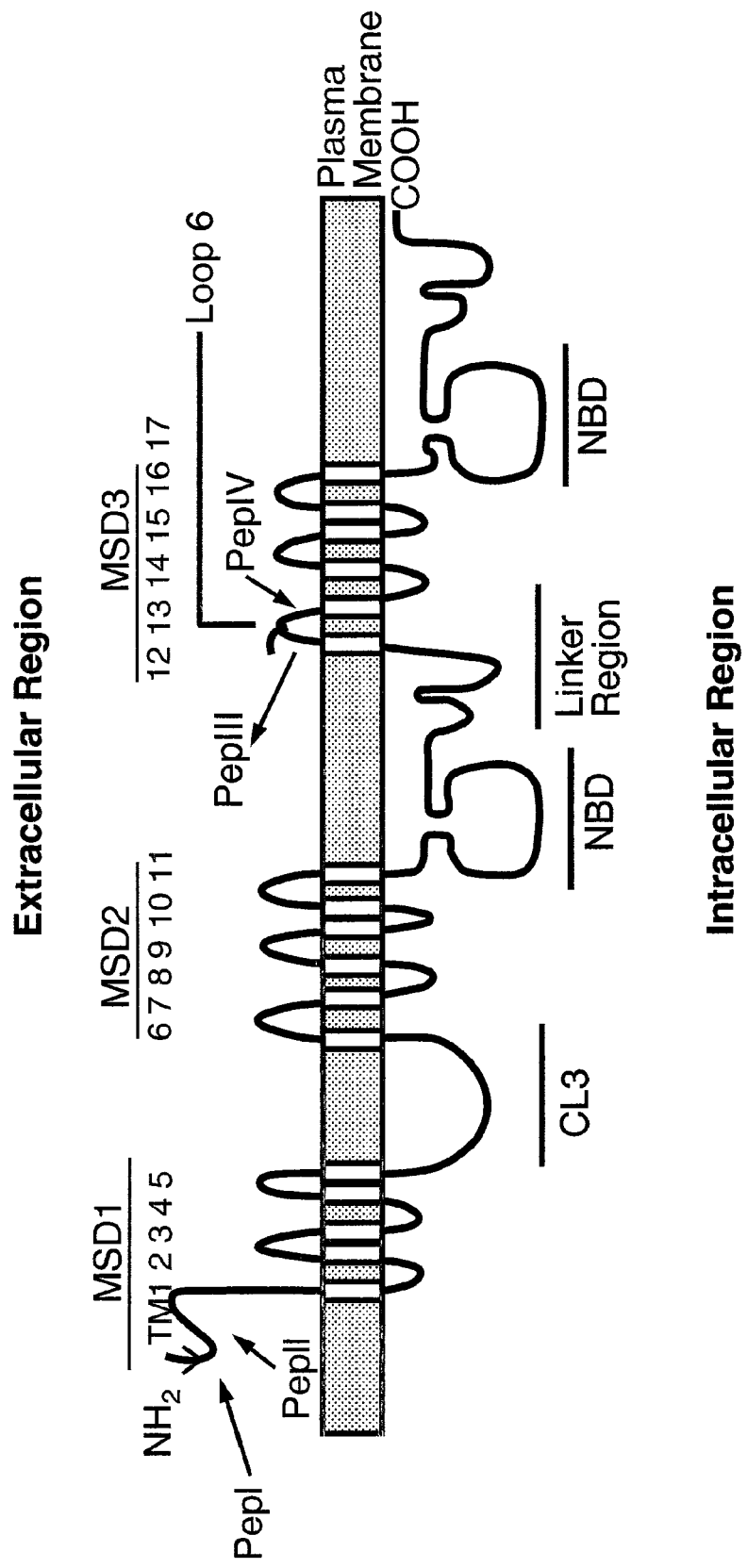
FIG. 2 is a schematic representation of the membrane topology of MRP3. Arrows indicate the location of peptides (i.e., PepI, PepII, PepIII, and PepIV) used for the preparation of scFV antibodies.

Using the antigenicity plot of MRP3 amino acid sequence and topology, we selected four peptides from extracellular domains that can elicit an immune response. As shown in FIG. 2, peptide I (PepI) and peptide II (PepII) encompassed amino acids 1-20 and 21-32 of the $NH_2$ terminus, respectively. Peptide III (PepIII) and peptide IV (PepIV) encompassed amino acids 999-1013 and 1053-1069, respectively, and mapped to an extracellular loop of MSD3 of human MRP3. The amino acid sequences and positions of the four peptides are shown in Table 1 above.

Example 2

Isolation of MRP3-Specific Single-Chain Fv Antibodies

To isolate scFv against the specific extracellular epitopes, a human naïve phage display library was screened.

A large human naïve scFv phage display library (i.e., Mehta II library; Dana Farber Cancer Institute, MA) containing $15 \times 10^9$ diversity was used for the selection of anti-MRP3 scFvs (See, e.g., Bai et al. J. Biol. Chem. 278:1433-42 (2003)). The vector pFarber was used to make the library. The library was subjected to three successive rounds of biopanning with biotinylated peptides (Anaspec, San Jose, Calif.) derived from MRP3 protein (i.e., PepI, PepII, PepIII, and PepIV), alternatively with Streptavidin-coated beads (Dynal) and avidin resin (Promega). To eliminate phages that bind to streptavidin beads, avidin resin was used in the next round of panning followed by streptavidin beads in the third and final round. Successive reductions in the concentration of the biotinylated peptide was used, 500 nM for the first round, 100 nM for the second and 20 nM for the third round. Streptavidin beads were mixed and the mixture was incubated in a pre-coated (5% milk PBS) tube with continuous rotation. A magnetic force was applied to separate the phages bound to the biotinylated complex. Bound phages were eluted by acidic (200 μl of 0.1 M HCl-glycine pH 2.0) and alkaline (200 μl of 100 mM triethylamine) treatment. Neutralization was done by adding 400 μl of 1M Tris HCl. Eluted mixtures were pooled and used to infect the amber-codon-suppressing, E. coli TG1 cells ($A_{600}$, 0.5) for 30 min at 37° C., which were later superinfected with VCSM13 interference-resistant helper phage (Stratagene) as described by Amersdorfer et al., Methods Mol. Biol. 145: 219-40 (2000). More phages were grown and subjected to further rounds of selection for the enrichment of putatively positive clones for the respective peptides used for screening. The ratio of phage input to phage output gives the enrichment value.

The phage population produced after each round of selection was screened by ELISA for binding to MRP3 peptides and was used to confirm the round-after-round enrichment of antigen-specific phages. Phages from single, infected bacterial colonies were then screened by ELISA to identify the monoclonal phage. For polyclonal phage ELISA, aliquots of phages after each round of selection were added to 96-well plates coated with 10 μg/ml of MRP3-derived peptides conjugated with BSA in 100 μl of 200 mM $NaHCO_3$, pH 9.6. Plates were incubated overnight for coating with antigen at 4° C. After washing plates with 0.05% Tween/PBS three times, they were blocked with 2% milk/PBS for 2 h at room temperature. After blocking, the wells were then briefly rinsed with PBS, and then plates were further incubated with phage supernatants diluted in 2% milk/PBS for 1 h at room temperature (~$10^{10}$ pfu/well). Plates were incubated with horseradish peroxidase (HRP)-conjugated mouse anti-M13 antibody (1:5000, Amersham, Piscataway, N.J.). Detection was performed by using the Sigmafast OPD o-phenylenediamine dihydrochloride tablet set (Sigma, St. Louis, Mo.). Phages from single, infected bacterial colony from second and third round of populations were then screened by monoclonal phage ELISA. TG1 colonies were picked randomly and expanded, supernatant was added to 96-well plates coated with MRP3-derived peptides, and ELISA was performed as described above.

A progressive and marked enrichment for phage was observed after each round of panning. As shown in Table 7, a total of ~67-fold and 390-fold enrichment was achieved between the first and third rounds of selection in the case of MRP3-derived PepI and PepII, respectively. There was a 72-fold enrichment with PepIV (data not shown) in the third round of panning.

TABLE 7

Anti-MRP3 scFV Enrichment.

| Round | Phage Input (PFU) | Resin | Peptide Conc. (nM) | Binding Time (h) | Phage Output (PFU) | Phage library (PFU) | Enrichment |
|---|---|---|---|---|---|---|---|
| PepI: 1 | $10^{12}$ | Strepavidin (200 µl) | 500 | 3 | $6 \times 10^5$ | $2.6 \times 10^{14}$ | 1 |
| PepI: 2 | $10^{12}$ | Avidin (40 µl) | 100 | 1.5 | $5.9 \times 10^6$ | $2.8 \times 10^{15}$ | ~10 |
| PepI: 3 | $10^{12}$ | Strepavidin (100 µl) | 20 | 1 | $4.08 \times 10^7$ | $4.3 \times 10^{15}$ | ~67 |
| PepII: 1 | $10^{12}$ | Strepavidin (200 µl) | 500 | 3 | $1 \times 10^5$ | $3 \times 10^{15}$ | 1 |
| PepII: 2 | $10^{12}$ | Avidin (40 µl) | 100 | 1.5 | $4.4 \times 10^6$ | $2.7 \times 10^{15}$ | 44 |
| PepII: 3 | $10^{12}$ | Strepavidin (100 µl) | 20 | 1 | $3.9 \times 10^7$ | $5 \times 10^{14}$ | 390 |

A marked enrichment of specific phage clones was observed after the third round of panning, as exhibited after polyclonal phage ELISA. For each peptide screening for monoclonal phage ELISA, 192 clones were picked. DNA sequencing was performed with the phage DNA of specific clones, and the amino acid sequence was deduced. Putative clones were picked for further analysis on the basis of their DNA sequence and their specificity as exhibited by monoclonal phage ELISA.

Of the 192 clones, 54, 28, 7, and 38 phage clones exhibited binding to immobilized MRP3-derived Peptide I, II, III, and IV, respectively, conjugated to BSA.

Example 3

DNA Sequencing of Phage Clones

Phage clones from the second and third rounds of panning were selected and their DNA was isolated and sequenced by using an AB1377 automatic sequencer (Applied Biosystems, Foster City, Calif.). Nucleotide sequences for positive clones were determined by primers "pelB forward" and "cmyc reverse" that hybridize the flanking sequence of the insert. Nucleotide sequences of the primers are as follows: "pelB-Forward" (located right before the heavy chain): 5'CATAAT-GAAATACCTATTGCCTA3'; and "cmycReverse" (located right after the light chain): CTTATTAGCGTTTGCCATT. Several positive clones were picked on the basis of their ELISA titer and nucleotide sequences for each of the MRP3-derived peptides (i.e., PepI, II, III, and IV) used for screening the phage library.

The amino acid sequence for three of the anti-MRP3 antibody scFVs of the present invention are disclosed in SEQ ID NOs: 9, 10 and 11 and FIG. 3 shows their variable light and heavy chains amino acid sequence alignment.

Example 4

Expression and Purification of PepI-58 scFv and PepII-89 scFv Protein

Recombinant anti-MRP3 scFv antibodies were expressed in bacterial cells and purified.

ScFv antibodies genes were cloned into expression vector pET 22$^{(+)}$ (Novagen, Madison, Wis.), to enable the expression of active and soluble scFv antibody. Briefly, scFv encoding fragment was excised from phagemid by digesting it with NcoI and Not I restriction endonuclease and ligated to NcoI and Not I digested pET vector. The vector carries Myc and hexahistidine tags for purification and detection. The scFv antibodies were expressed in *E. coli* BL21 (DE3) gold cells (Stratagene, La Jolla, Calif.) and purified from the soluble cytoplasmic fraction by metal-ion affinity chromatography (Talon, Clontech, Palo Alto, Calif.). Recombinant scFv that bind specifically to PepI, PepII, PepIII, and PepIV were selected for further analysis and are referred to herein as PepI-58 scFv, PepI-25 scFV, PepII-89 scFV, PepIII-23 scFV, and PepIV-17 scFV, respectively.

Figure 4A:
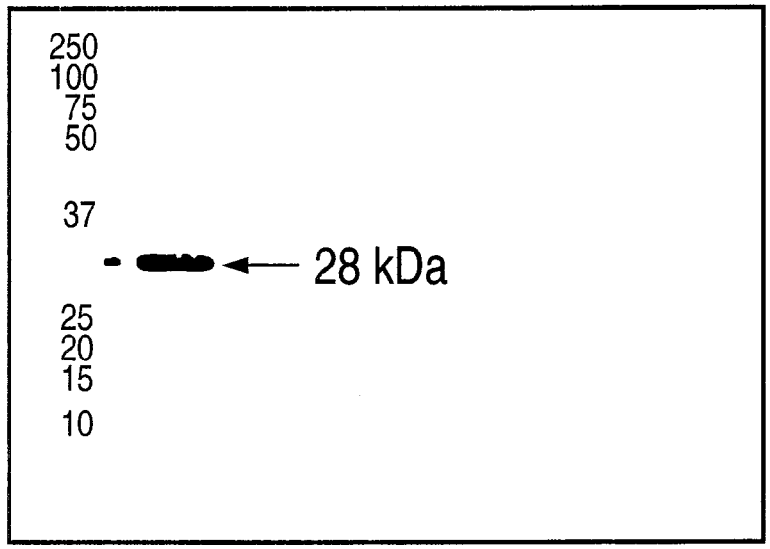
FIG. 4 shows SDS-PAGE analysis of purified anti-MRP3 single-chain Fv antibodies. (A) PepII-89 scFv antibody fragment and (B) PepI-58 scFv antibody fragment. Transformed *E. coli* BL21 (λDE3) cells expressing the PepII-89 scFv or PepI-58 scFv were harvested, and the antibody was purified from the whole-cell extracts by metal-affinity chromatography utilizing a hexahistidine ($His_6$) tag fused to the C terminus of the scFv gene. The PepII-89 scFv reacted with MRP3-derived peptide II (PepII), while the PepI 58 scFv reacted with PepI antigen. The arrow on the right of the gel points to 28 kDa, the calculated size of the scFv antibody fragment.
Figure 4B:
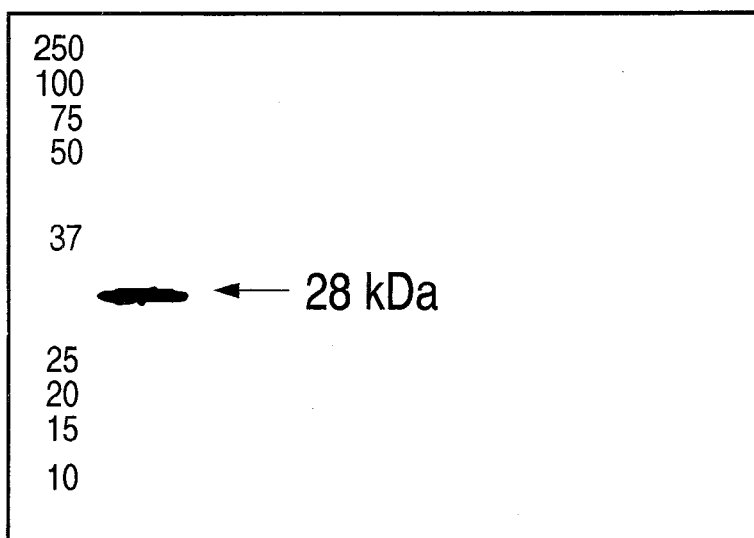

Purified svFV were analyzed on 4%-12% SDS PAGE, which revealed a major single band of ~28 kDa as shown in FIG. 4 for PepI-58 scFV and PepII-89 scFV.

Example 5

Binding Specificity of Anti-MRP3 scFvs

To determine whether recombinant scFv can bind specifically to its corresponding MRP3-derived peptides, the soluble purified scFv antibodies were examined for their binding specificity by ELISA.

A 96-well plate was coated with 10 µg/ml of specific MRP3-derived peptides conjugated with BSA as antigen and BSA and other appropriate control antigens. The rest of the protocol was as described above except that the purified scFv antibodies were added in serial dilution to the wells, and the secondary Ab used was HRP-conjugated anti-His antibody at 1:5000 dilution (Invitrogen, Carlsbad, Calif.). To check for cross-reactivity of the recombinant scFvs, the ELISA plate was coated with different peptide antigens (i.e., PepI, PepII, PepIII, PepIV) derived from MRP3, conjugated to BSA with other controls. ScFv antibodies were then added at a 10 µg/ml concentration to each well.

Figure 5A:
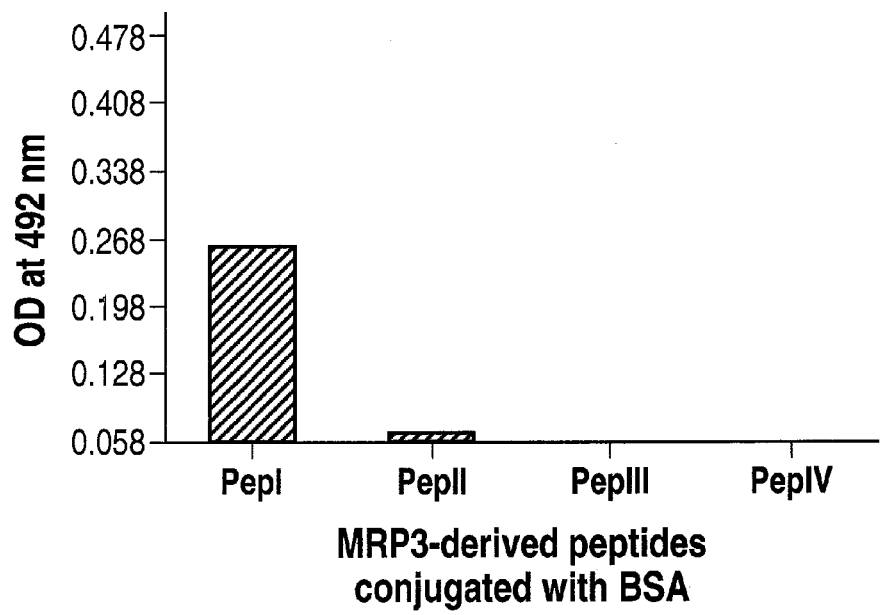
FIG. 5 shows specificity of (A) anti-MRP3 PepI-58scFv and (B) anti-MRP3 PepII-89scFv as determined by enzyme-linked immunosorbent assay (ELISA) with soluble purified recombinant scFv. The PepI-58 scFv reacted only with PepI antigen but not with other MRP3-derived peptides (PepII, PepIII, and PepIV). The PepII-89 scFv reacted only with PepII antigen and not with other MRP3-derived peptides (PepI, PepIII, and PepIV).
Figure 5B:
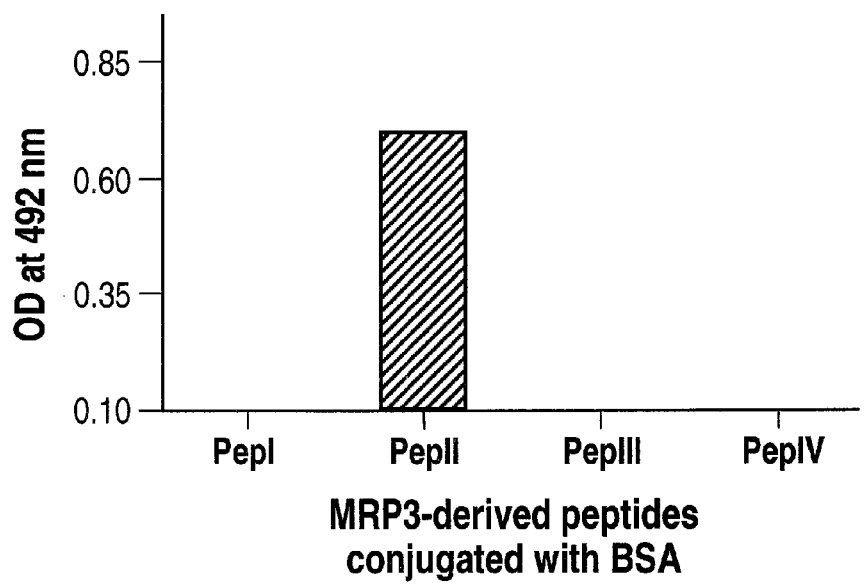

All scFvs reacted in a dose-dependent manner with their corresponding MRP3-derived peptides conjugated to BSA. Also, the scFvs reacted only with the specific MRP3 peptide that was used to screen the library and did not cross-react with other MRP3 peptides. FIG. 3 shows the binding specificity for PepI-58 scFV (FIG. 5A) and PepII-89 scFV (FIG. 5B).

Example 6

Binding Kinetics and Affinity Measurements of Anti-MRP3 scFvs

Surface plasmon resonance technology was used to characterize the binding kinetics and affinity of purified scFv antibody with immobilized biotinylated specific peptide.

Kinetic measurements of purified recombinant scFv were made by surface plasmon resonance using a BIAcore 3000 Biosensor (BIAcore, Piscataway, N.J.). Chips were functionalized with biotinylated peptides derived from MRP3 protein by using HEPES balanced salt solution (HBSS buffer), 10 mM HEPES pH 7.4, 150 mM NaCl, 3.4 mM EDTA, and 0.05% BIAcore surfactant P20. The scFv antibodies were diluted in HBSS buffer and passed over the SA chip at concentrations of 25, 200, and 1000 nM. The flow rate was kept at 30 µl/min, and the injection time was 3 min. Binding constants were calculated from the nonlinear fitting curve by using the BIAevaluation software (BIAcore).

The characterization of scFvs (e.g., PepI-58 scFv, PepI-25 scFv, PepII-89 scFv, PepIII-23 scFv, and PepIV-17 scFv) by BIAcore revealed that these recombinant scFvs bind to the corresponding MRP3 antigen on the microsensor chip.

Figure 6A:
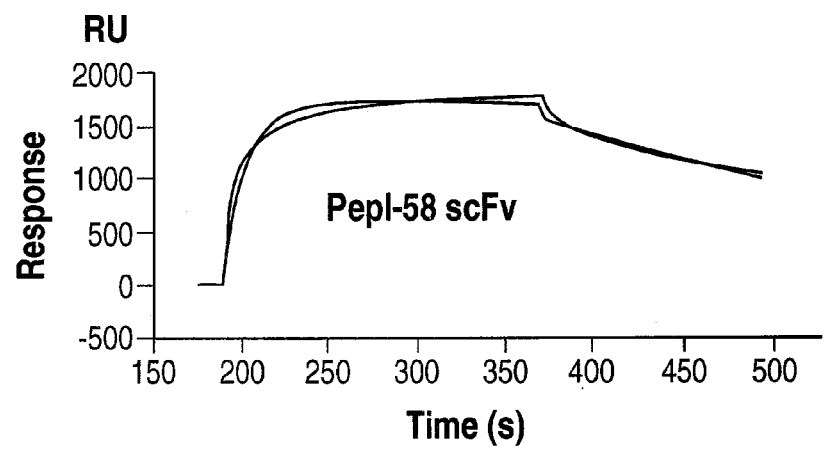
FIG. 6 shows BIAcore analysis for PepI-58 scFv, PepI-25 scFv, and PepII-89 scFv.
Figure 6B:
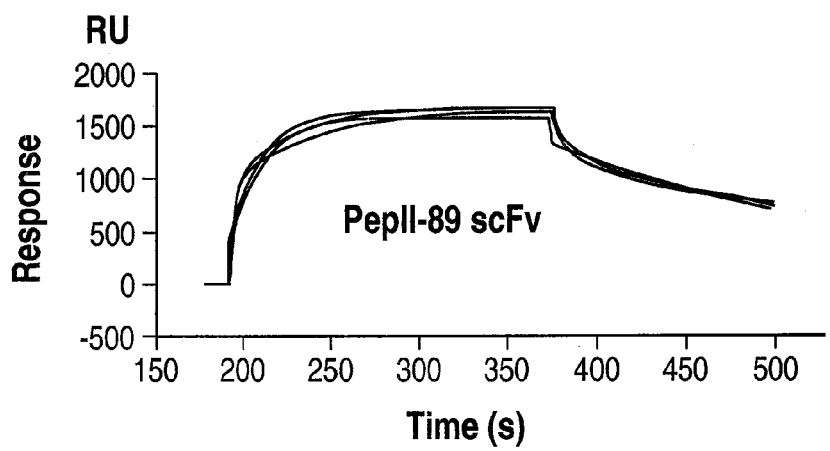

The association and dissociation rates from the sensogram were $k_{assoc}=7.1\times10^4$ (mol/L-s)$^{-1}$ and $k_{diss}=3.4\times10^{-3}$ s$^{-1}$ for PepI-58 scFv; and $k_{assoc}=5.1\times10^4$ (mol/L-s)$^{-1}$ and $k_{diss}=5\times10^{-3}$ s$^{-1}$ for PepII-89. As shown in FIGS. 6A and B, respectively, the $K_A$ at binding equilibrium, calculated as $K_A=k_{assoc}/k_{diss}$, was $2.1\times10^7$ (mol/L)$^{-1}$ for PepI-58 scFv and $1\times10^7$ (mol/L)$^{-1}$ for PepII-89 scFv.

Figure 6C:
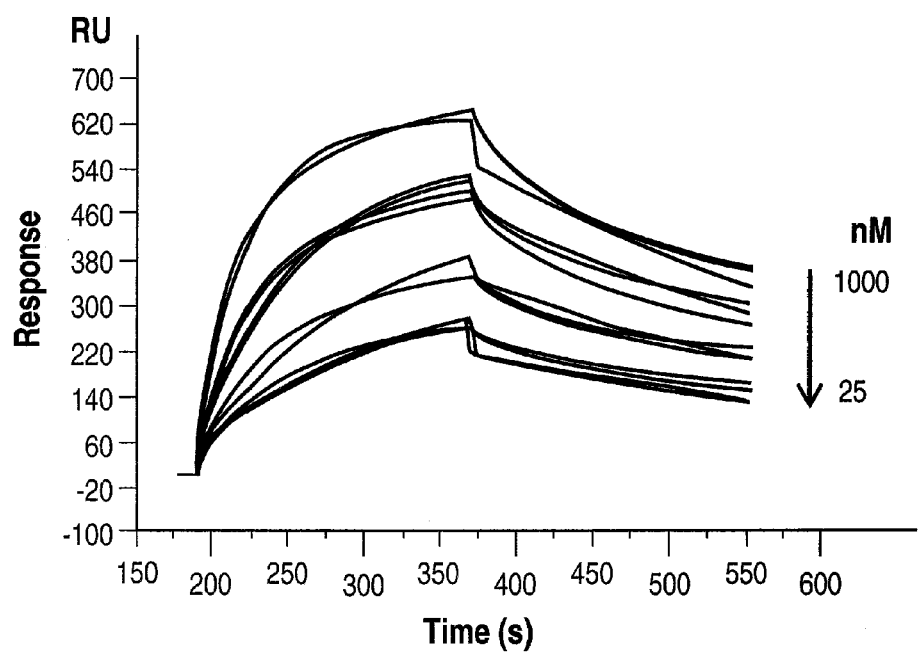

The association and dissociation rates from the sensograms were in the same range for PepI-58 scFv, PepI-25 scFv, and PepII-89 scFv. FIG. 6C shows an example of the binding kinetics between PepI-25 scFv and the immobilized biotinylated specific peptide pep-I. The various lines shown in FIG. 6C are the association and dissociation curves ranging from 25 nM to 1000 nM of purified PepI-25 scFv antibody. The final binding affinity was determined by the software developed by BIAcore based on the kinetics calculated among various concentrations of antibody. PepI-25 scFv had $k_{assoc}=1.3\times10^5$ (mol/L-s)$^{-1}$, $k_{diss}=2.8\times10^{-3}$ s$^{-1}$, and $K_A=k_{assoc}/k_{diss}$, was $4.6\times10^7$ (mol/L)$^{-1}$.

Example 7

Binding of Anti-MRP3 scFvs to MRP3-Expressing Tumor Cells

To determine that the purified anti-MRP3 scFvs bind native MRP3 expressed on the surface of tumor cells, indirect fluorescence-activated cell sorting (FACS) was performed using MRP3-expressing D54MG and D247MG cells under both permeabilized and nonpermeabilized conditions. Indirect FACS analysis of MRP3 expression on the surface of viable malignant pediatric GBM cell line D2159 growing as neuroshperes was also performed.

For cytometric analysis of PepI-58, PepI-25, PepII-89, PepIII-23, and PepIV-17 scFv antibodies, D54MG and D247MG cells ($1\times10^6$/test) were harvested with 0.02% EDTA/PBS and fixed by resuspending them in 2-4 ml of 10% formaldehyde. After washing, the cells were blocked with 10% normal goat serum (NGS) with and without saponin for 20 min. Saponin was added to facilitate the permeabilization for examining all surface receptors. Cells were washed twice and incubated with anti-his (C-terminus)-FITC conjugated antibody (1:5000, Invitrogen, Carlsbad, Calif.) for an hour at room temperature. Finally, cells were suspended in 0.5% PFA/BSA and freshly analyzed by using a Becton Dickinson FACSort with CellQuest software (Becton Dickinson, San Jose, Calif.).

Figure 7A:
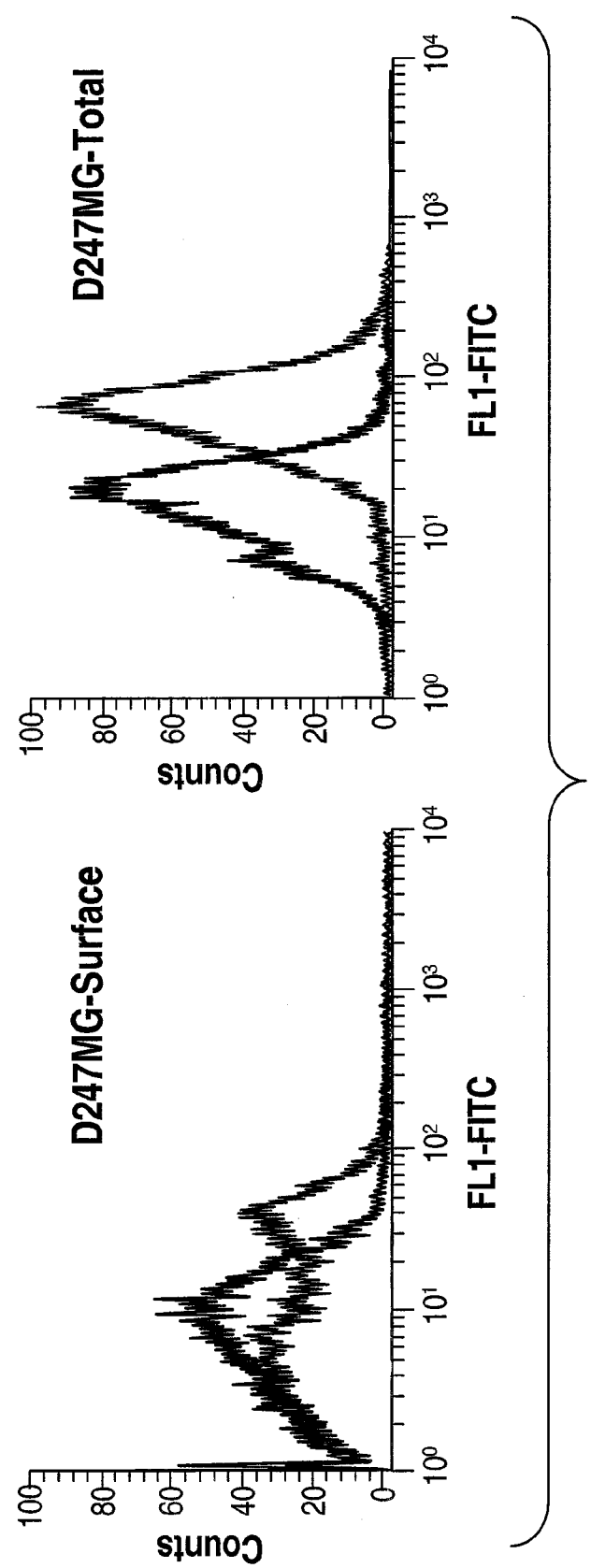
FIG. 7 shows detection of MRP3 on malignant cells by the PepI 58, PepI-25, and PepII-89 scFvs as determined by indirect flow cytometric analysis (FACS) of MRP3 expression.
Figure 7B:
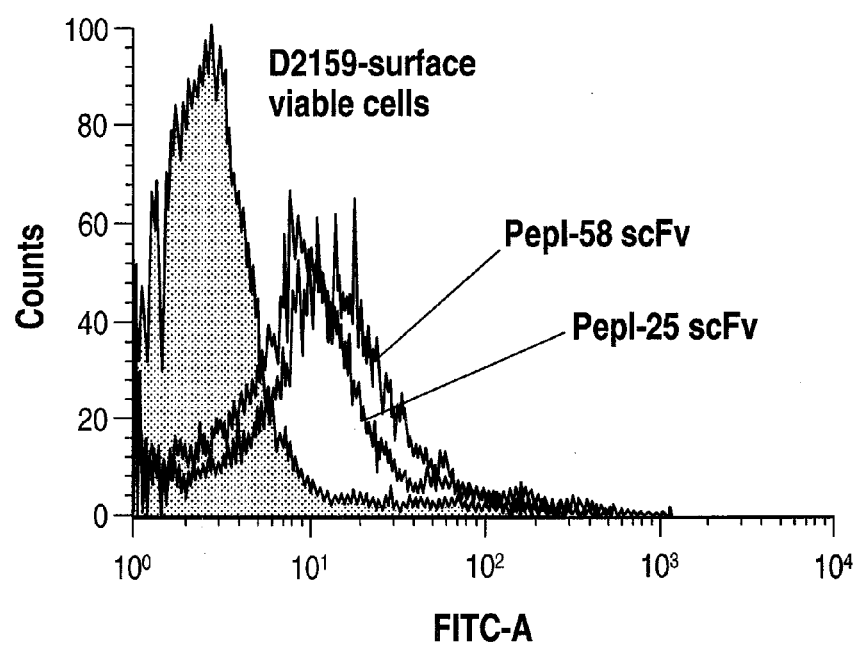

Flow cytometric analysis for these scFvs showed cell surface reactivity with D54MG and D247MG cells under nonpermeabilized conditions. Further, as shown in FIG. 7A for PepI-58 and PepII-89 scFv antibodies, D247MG and D54MG showed a shift in the peak, both in permeabilized and in nonpermeabilized cells, indicating the binding of PepI-58 and PepII-89 scFv antibodies to surface MRP3 molecules. Irrelevant control scFv was unreactive with both cell lines. And, as shown in FIG. 7B, there is excellent binding of PepI-58 scFv and PepI-25 scFv to the cell surface of D2159 cells.

Although PepI-58 scFv, PepI-25 scFv, PepII-89 scFv, and PepIV-17 scFv showed good binding with cell-surface-expressed MRP3, PepIII-23 scFv did not recognize the epitope on cell-surface-expressed MRP3. Without being held to a particular theory, one possible explanation may be that the epitope for PepIII-23 scFv is masked or it is partially inside the membrane.

Example 8

Radioiodination and Immunoreactivity of Purified Anti-MRP3 scFvs

Purified recombinant scFv (PepI-58 and PepII-89) were labeled with Iodine125 ($^{125}$I) by using the Iodogen method, as described by Reist et al (Reist, Archer et al. 1995; Reist, Archer et al. 1997), to a specificity of 1 to 3 µCi/µg and purified by using gel filtration by a 10-cm PD-10 Sephadex G-25 (Pharmacia) (Reist, Garg et al. 1996).

Immunoreactive fractions of the radioiodinated PepI-58 and PepII-89 scFvs were determined according to the method described by Lindmo et al (Lindmo, Boven et al. 1984). Fractions of immunoreactive scFvs were calculated by linear exploitation of infinite antigen excess. One milliliter of Streptavidin-coated beads, MPG Streptavidin (Pure Biotech, LLC, Middlesex, N.J.), were coated with 200 µg of biotinylated PepI and PepII separately or with bovine serum albumin (BSA), to measure nonspecific binding. Beads were then rinsed to remove unbound peptides and resuspended in the original volume of Lindmo buffer (115 mM PO$_4$ buffer of pH 7.5, 0.05% BSA, and 0.05% Brij detergent (Sigma, St Louis, Mo.). Triplicate aliquots of beads in increasing volumes (25, 50, 100 µl) were incubated with 50 µl of Lindmo buffer containing 5 ng of each of the labeled scFv antibodies for 45 min at room temperature. The final volume was adjusted with Lindmo buffer. Beads were washed and separated by using a magnetic separator, and both pellets and supernatants were counted in a gamma counter. Specific binding was calculated by subtracting nonspecific binding to BSA-coated beads from the binding of PepI-58 and PepII-89 scFvs separately. Plotting the total activity divided by the specifically bound activity versus the reciprocal of the antigen concentration yielded a linear plot, the intercept of which represents the inverse of the immunoreactive fraction.

The radiolabeling yields were 56%-76% for PepI and PepII scFv MAbs, and the kinetics and affinities were equivalent to unlabeled protein. The immunoreactive fraction of the labeled PepI-58 scFv MAb was 51.8%, and for PepII-89 it was 68.8%.

Example 9

Internalization and Processing of Anti-MRP3 scFV

The internalization assays were performed with D54MG and D247MG cell lines, plated at a density of $5 \times 10^5$ cells per well in zinc option medium and incubated at 4° C. for 30 min. The medium was removed and replaced with fresh cold medium containing 1 of radiolabeled scFv antibody in each well. After 1 h of incubation at 4° C., the medium was removed, and wells were washed twice with 1 ml of cold media to remove unbound activity. Fresh zinc option media was added to the wells, and plates were placed in an incubator at 37° C. for different time points (0, 1, 2, 4, 8, 20, and 24 h). After each time point, supernatant was removed, and cells were washed twice with zinc option medium (pH 2.0) for 10 min, to remove surface-bound activity. Finally, the cells were solubilized in 0.5 ml of 0.5 N NaOH (internalized fraction). Each supernatant sample was precipitated by 12% TCA to calculate acid precipitable counts. All the fractions of the supernatant, acid washes, and the cell pellets were counted in a gamma counter and were expressed as the percentage of activity initially bound to the cells after 1 h of incubation at 4° C.

Figure 8A:
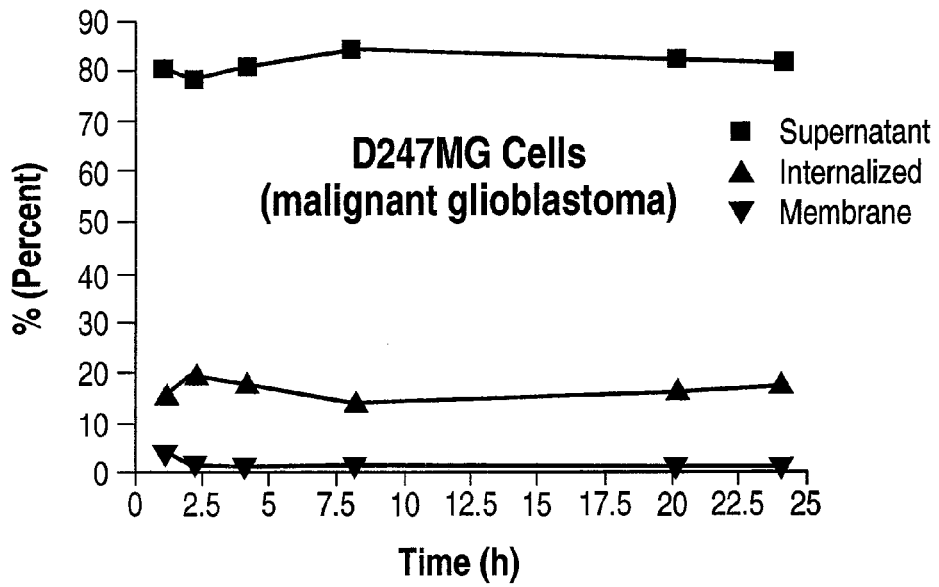
FIG. 8 shows in vitro internalization assay of $I^{125}$-labeled (via Iodogen method) anti-MRP3 PepII-89 scFv on (A) D247MG and (B) D54MG malignant glioma cells. The percentage of radioactivity initially bound to cells (membrane [▼] or internalized [▲]) and cell culture supernatant (■) is shown. A marked increase in radioactive counts was observed in the cell culture supernatant, with a decrease in counts associated with cell surface. The profile showed that the internalization of PepII-89 scFv into D247MG cells gradually increased to a maximum percentage (20%) of intracellular counts at the 2-h time point compared with 33% for D54MG cells at the 1-h time point; 20% of pepII-89scFv counts were detected intracellularly throughout the time course up to the 20-h time point for both D54MG and D247MG.
Figure 8B:
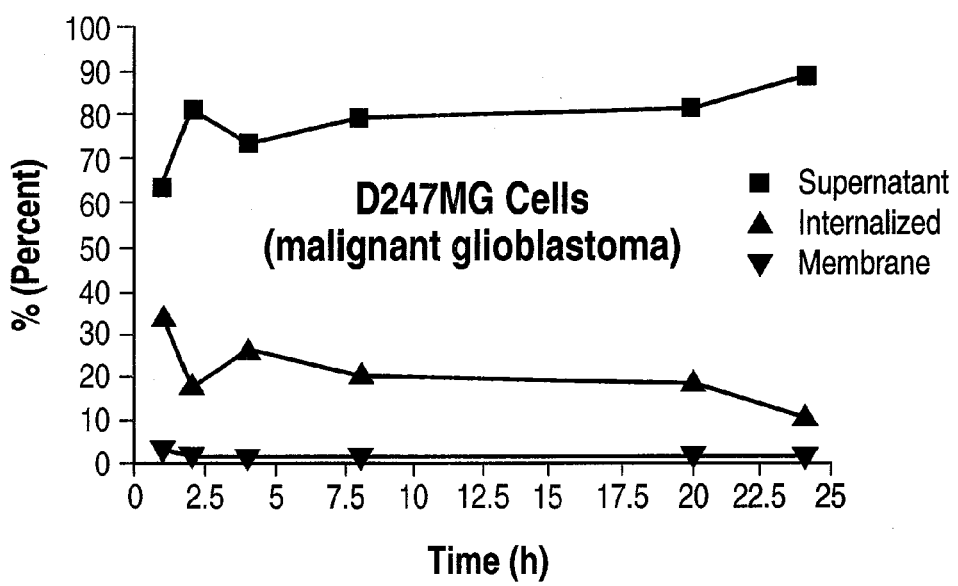

As shown in FIG. 8, percentage of radioactive counts for cell culture supernatant, cell surface, and intracellular compartments for different time points were plotted for both cell lines. Cell-surface-associated counts for PepII-89 scFvs showed a rapid drop, accompanied by an increase in counts in the cell culture supernatant (FIG. 8A). During early time points, from 1 to 4 h, approximately 70%-80% of associated counts were released to the cell culture supernatant. The radioactivity of scFv associated with the cell culture supernatant increased and accounted for 80% of the radioactive counts for D247MG cells and 90% for D54MG cells of the total cpm recovered after 24 h at 37° C. (FIG. 8A). The profile showed that the internalization of PepII-89 scFv into D247MG cells gradually increased to a maximum percentage (20%) of intracellular counts at the 2-h time point as compared with 33% for D54MG cells at the 1-h time point. For both D54MG and D247MG, 20% of the PepII-89 scFv counts were detected intracellularly throughout the time course up to the 20-h time point (FIG. 8).

What is claimed is:

1. An isolated antibody that selectively binds an epitope located in an extracellular portion of multidrug resistance protein 3 (MRP3), wherein the antibody comprises a domain having an amino acid sequence selected from the group consisting of a PepI-58 variable heavy domain (SEQ ID NO:5), a PepI-58 variable light domain (SEQ ID NO:6), a PepI-25 variable heavy domain (SEQ ID NO:7), a PepI-25 variable light domain (SEQ ID NO:8), a PepII-89 variable heavy domain (SEQ ID NO:9), a PepII-89 variable light domain (SEQ ID NO:10), a PepIII-23 variable heavy domain (SEQ ID NO:11), a PepIII-23 variable light domain (SEQ ID NO:12), a PepIV-17 variable heavy domain (SEQ ID NO:13), and a PepIV-17 variable light domain (SEQ ID NO:14).

2. The antibody of claim 1, wherein the antibody is a single chain Fv.

3. An isolated antibody that selectively binds an epitope located in an extracellular portion of multidrug resistance protein 3 (MRP3), wherein the antibody comprises an antigen binding region of, or binds a MRP3 epitope bound by, an anti-MRP3 antibody comprising:
   a) a variable heavy chain comprising the amino acid sequence set forth as SEQ ID NO:5 and a variable light chain comprising the amino acid sequence set forth as SEQ ID NO:6;
   b) a variable heavy chain comprising the amino acid sequence set forth as SEQ ID NO:7 and a variable light chain comprising the amino acid sequence set forth as SEQ ID NO:8;
   c) a variable heavy chain comprising the amino acid sequence set forth as SEQ ID NO:9 and a variable light chain comprising the amino acid sequence set forth as SEQ ID NO:10;
   d) a variable heavy chain comprising the amino acid sequence set forth as SEQ ID NO:11 and a variable light chain comprising the amino acid sequence set forth as SEQ ID NO:12; or
   e) a variable heavy chain comprising the amino acid sequence set forth as SEQ ID NO:13 and a variable light chain comprising the amino acid sequence set forth as SEQ ID NO:14.

4. The antibody of claim 3, wherein the antibody is a humanized antibody.

5. A pharmaceutical composition comprising the antibody of claim 3; and a pharmaceutically acceptable carrier.

6. The antibody of claim 3, wherein the antibody is attached to at least one effector.

7. The antibody of claim 6, wherein at least one effector is selected from the group consisting of an epitope tag, a second antibody, a label, a cytotoxin, a liposome, a radionuclide, a drug, a prodrug, and a chelate.

8. A kit comprising the antibody of claim 3, and reagents for detecting the antibody.

9. A method for treating cancer comprising MRP3-expressing cells, the method comprising: administering to the mammal a therapeutically effective amount of a pharmaceutical composition comprising the antibody of claim 3.

10. A method of treating cancer comprising MRP3-expressing cells in an individual, the method comprising providing to the individual a therapeutically effective amount of the antibody of claim 6, wherein the at least one effector is selected from the group consisting of a cytotoxin, a radionuclide, a liposome comprising an anti-cancer agent, a drug, a prodrug, and an anti-cancer agent.

11. A method for targeted delivery of at least one effector to a cell expressing MRP3, the method comprising contacting the cell with the antibody of claim 6.

12. A method for killing a MRP3-expressing cell, the method comprising contacting the cell with the antibody of claim 6, wherein the at least one effector is selected from the group consisting of a cytotoxin, a radionuclide, a liposome comprising an anti-cancer agent, a drug, a prodrug, and an anti-cancer agent.

13. A method for imaging cancer comprising MRP3-expressing cells in a mammal, the method comprising administering to the mammal a diagnostically effective amount of an antibody that is detectably-labeled, wherein the antibody is according to claim 3.

14. A method of identifying a cell expressing MRP3, the method comprising contacting the cell with the antibody of claim 3; and detecting the antibody.

* * * * *

SEQUENCE LISTING

```
<160> NUMBER OF SEQ ID NOS: 55

<210> SEQ ID NO 1
<211> LENGTH: 20
<212> TYPE: PRT
<213> ORGANISM: Homo sapiens

<400> SEQUENCE: 1

Met Asp Ala Leu Cys Gly Ser Gly Glu Leu Gly Ser Lys Phe Trp Asp
1               5                   10                  15

Ser Asn Leu Ser
            20

<210> SEQ ID NO 2
<211> LENGTH: 12
<212> TYPE: PRT
<213> ORGANISM: Homo sapiens

<400> SEQUENCE: 2

Val His Thr Glu Asn Pro Asp Leu Thr Pro Cys Phe
1               5                   10

<210> SEQ ID NO 3
<211> LENGTH: 15
<212> TYPE: PRT
<213> ORGANISM: Homo sapiens

<400> SEQUENCE: 3

Asp Ala Met Ala Asp Ser Arg Gln Asn Asn Thr Ser Leu Arg Leu
1               5                   10                  15

<210> SEQ ID NO 4
<211> LENGTH: 17
<212> TYPE: PRT
<213> ORGANISM: Homo sapiens
```

<400> SEQUENCE: 4

```
Lys Ile Arg Ser Pro Gln Ser Phe Phe Asp Thr Thr Pro Ser Gly Arg
1               5                   10                  15

Ile
```

<210> SEQ ID NO 5
<211> LENGTH: 117
<212> TYPE: PRT
<213> ORGANISM: Homo sapiens

<400> SEQUENCE: 5

```
Glu Val Gln Leu Val Gln Ser Gly Gly Gly Leu Val Gln Pro Gly Gly
1               5                   10                  15

Ser Leu Arg Leu Ser Cys Ser Ala Ser Gly Phe Thr Phe Ser Asn Tyr
            20                  25                  30

Ala Met His Trp Val Arg Arg Ala Pro Gly Lys Gly Leu Glu Tyr Val
        35                  40                  45

Ser Ala Ile Ser Ser Asn Gly Gly Ser Thr Tyr Tyr Ala Asp Ser Val
    50                  55                  60

Lys Gly Arg Phe Thr Ile Ser Arg Asp Asn Pro Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Gly Arg Pro Tyr Pro Leu Asp Val Trp Gly Lys Gly Thr Leu
            100                 105                 110

Val Thr Val Ser Ser
        115
```

<210> SEQ ID NO 6
<211> LENGTH: 118
<212> TYPE: PRT
<213> ORGANISM: Homo sapiens

<400> SEQUENCE: 6

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Glu Ser His
            20                  25                  30

Ala Val Asn Trp Tyr Gln His Leu Pro Gly Ser Ala Pro Lys Leu Leu
        35                  40                  45

Ile Tyr Phe Asn Asn His Arg Pro Ser Gly Val Pro Glu Arg Phe Ser
    50                  55                  60

Ala Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Pro Val Phe Gly Gly Gly Thr Lys Leu Thr Val Leu Gly Gln
            100                 105                 110

Pro Lys Ala Ala Pro Ser
        115
```

<210> SEQ ID NO 7
<211> LENGTH: 114
<212> TYPE: PRT
<213> ORGANISM: Homo sapiens

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Thr Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
50                      55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Gly Asp Leu Asp Tyr Trp Gly Gln Gly Thr Thr Val Thr Val
            100                 105                 110

Ser Ser

<210> SEQ ID NO 8
<211> LENGTH: 120
<212> TYPE: PRT
<213> ORGANISM: Homo sapiens

<400> SEQUENCE: 8

Gln Thr Val Val Thr Gln Glu Pro Ser Leu Thr Val Ser Pro Gly Gly
1               5                   10                  15

Thr Val Thr Leu Thr Cys Ala Ser Ser Thr Gly Ala Val Thr Ser Gly
            20                  25                  30

Tyr Tyr Pro Asn Trp Phe Gln Gln Lys Pro Gly Gln Ala Pro Arg Ala
            35                  40                  45

Leu Ile Tyr Ser Thr Ser Asn Lys His Ser Trp Thr Pro Ala Arg Phe
50                      55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Leu Leu Tyr Tyr Gly Gly
                85                  90                  95

Ala Gln Pro Tyr Val Val Phe Gly Gly Gly Thr Lys Val Thr Val Leu
            100                 105                 110

Gly Gln Pro Lys Ala Ala Pro Ser
            115                 120

<210> SEQ ID NO 9
<211> LENGTH: 114
<212> TYPE: PRT
<213> ORGANISM: Homo sapiens

<400> SEQUENCE: 9

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Asp Pro Gly Lys Gly Leu Met Trp Val
            35                  40                  45

Ser Ser Ile Ser Thr Asp Gly Ser Ala Thr Lys Tyr Ala Asp Ser Val
50                      55                  60

Lys Gly Arg Phe Thr Ile Ser Arg Asp Asn Ala Lys Asn Thr Val Ser
65                  70                  75                  80

Leu Gln Met Asn Ser Leu Arg Ala Glu Asp Thr Ala Val Tyr Tyr Cys

```
                    85                  90                  95

Val Gly Gly Phe Leu Gly Trp Trp Gly Gln Gly Thr Leu Val Thr Val
                100                 105                 110

Ser Ser

<210> SEQ ID NO 10
<211> LENGTH: 118
<212> TYPE: PRT
<213> ORGANISM: Homo sapiens

<400> SEQUENCE: 10

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Gly Gly Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Arg Arg Ala Thr Gly Ile Pro Ala Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Ser Tyr Phe Cys Gln Gln Thr Asn Thr Phe Pro
                85                  90                  95

Leu Thr Phe Gly Gly Gly Thr Lys Val Glu Ile Lys Arg Thr Val Ala
                100                 105                 110

Ala Pro Thr Ala Ala Ala
        115

<210> SEQ ID NO 11
<211> LENGTH: 121
<212> TYPE: PRT
<213> ORGANISM: Homo sapiens

<400> SEQUENCE: 11

Glu Val Gln Leu Val Gln Ser Gly Gly Gly Leu Val Lys Pro Gly Gly
1               5                   10                  15

Ser Leu Arg Leu Ser Cys Ala Ala Ser Gly Phe Ser Phe Asn Asn Tyr
            20                  25                  30

Ala Gly Ser Trp Val Arg Gln Ala Pro Gly Lys Gly Leu Glu Trp Ile
        35                  40                  45

Ser Ala Leu Ser Ser Gly Gly Asp Thr Thr Tyr Tyr Ala Asp Ser Val
    50                  55                  60

Ala Gly Arg Phe Ala Ile Ser Arg Asp Asn Ser Lys Asn Thr Leu Tyr
65                  70                  75                  80

Leu Gln Met His Ser Leu Arg Ala Glu Asp Thr Ala Ile Tyr Tyr Cys
                85                  90                  95

Ala Gln Asp Pro Val Val Gly Ala Pro Gly Tyr Phe Gly Leu Trp Gly
                100                 105                 110

Arg Gly Thr Leu Val Thr Val Ser Ser
        115                 120

<210> SEQ ID NO 12
<211> LENGTH: 119
<212> TYPE: PRT
<213> ORGANISM: Homo sapiens

<400> SEQUENCE: 12
```

Gln Ser Val Leu Thr Gln Pro Pro Ser Ala Gly Ser Ser Gly Gln
1               5                   10                  15

Ser Val Thr Ile Ser Cys Thr Gly Thr Ser Ser Asp Ile Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Lys Arg Pro Ser Gly Val Ser Asp Arg Phe
    50                  55                  60

Ser Gly Ser Lys Ser Gly Ser Thr Ala Ser Leu His Ile Ser Gly Leu
65                  70                  75                  80

Gln Ala Glu Asp Glu Ala Asp Tyr Tyr Cys Ser Ser Tyr Ser Ser Asn
                85                  90                  95

Asn Ala Pro Tyr Val Phe Gly Ser Gly Thr Lys Val Ala Val Leu Gly
            100                 105                 110

Gln Pro Lys Ala Ala Pro Ser
        115

<210> SEQ ID NO 13
<211> LENGTH: 120
<212> TYPE: PRT
<213> ORGANISM: Homo sapiens

<400> SEQUENCE: 13

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Thr Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Ser Pro Asp Thr Ser Lys Asn
65                  70                  75                  80

His Phe Ser Leu Gln Leu Asn Ser Val Thr Pro Glu Asp Thr Ala Val
                85                  90                  95

Tyr Tyr Cys Ala Arg Glu Gly Asn Asp Ala Phe Asp Ile Trp Gly Gln
            100                 105                 110

Gly Thr Met Val Thr Val Ser Ser
        115                 120

<210> SEQ ID NO 14
<211> LENGTH: 118
<212> TYPE: PRT
<213> ORGANISM: Homo sapiens

<400> SEQUENCE: 14

Gln Ser Ala Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Glu Ala Trp Asp Asp Ser Leu
            85                  90                  95

Asn Gly Pro Val Phe Gly Gly Gly Thr Lys Leu Thr Val Leu Gly Gln
            100                 105                 110

Pro Lys Ala Thr Pro Ser
        115

<210> SEQ ID NO 15
<211> LENGTH: 15
<212> TYPE: PRT
<213> ORGANISM: Artificial
<220> FEATURE:
<223> OTHER INFORMATION: Synthetic linker

<400> SEQUENCE: 15

Gly Gly Gly Gly Ser Gly Gly Gly Gly Ser Gly Gly Gly Gly Ser
1               5                   10                  15

<210> SEQ ID NO 16
<211> LENGTH: 750
<212> TYPE: DNA
<213> ORGANISM: Homo sapiens

<400> SEQUENCE: 16
gaggtgcagc tggtgcagtc tggggggaggc ttggtccagc ctgggggggtc cctgagactc      60 tcctgttcag cctctggatt caccttcagt aactatgcta tgcactgggt ccgccgggct     120
ccagggaagg gactggaata tgtttcagct attagtagta tgggggtag cacatactac     180 gcagactccg tgaagggcag attcaccatc tccagagaca tcccaagaa cacgctgtat     240 ctgcaaatga acagtctgag agccgaggac acggctgtgt attactgtgt aagagggcgt     300
ccctaccccg ctggacgtctg gggcaaaggc accctggtca ccgtctcctc aggtggcggc     360
ggttccggag gtggtggttc tggcggtggt ggcagccagt ctgtgctgac tcagccaccc     420
tcagcgtctg gaccccccgg gcagaggggtc accatctctt gttctggcag cagctccaac     480
atcgaaagtc atgctgttaa ttggtatcag cacctcccag atcggccccc caaactcctc     540
atctatttca ataatcaccg gccctcgggg gtccctgagc gattctctgc ctccaagtct     600
ggcacctcag cctccctggc catcagtggg ctccagtctg aggatgaggc tgattattac     660
tgtgcagcat gggatgacag cctgaatggt ccggtattcg gcggaggggac caagctgacc     720 gtcctaggtc agcccaaggc tgccccctcg                                     750

<210> SEQ ID NO 17
<211> LENGTH: 747
<212> TYPE: DNA
<213> ORGANISM: Homo sapiens

<400> SEQUENCE: 17
gaggtgcagc tggtggagtc tggggggaggc ttggtacagc ctgggggggtc cctgagactc      60 tcctgtgcag cctctggatt caccttttagt aactatgcca tgacctgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcaaatga acagcctgag agccgaggac acggccgtat attactgtgc gacgggcgac     300
cttgactact ggggccaggg gaccacggtca ccgtctcct caggtggcgg cggttccgga     360
ggtggtggtt ctggcggtgg tggcagccag actgtggtga ctcaggagcc ctcactgact     420
gtgtccccag agggacagt cactctcacc tgtgcttcca gcactggagc agtcaccagt     480

```
ggttactatc caaactggtt ccagcagaaa cctggacaag cacccagggc actgatttat      540
agtacaagca acaaacactc ctggaccect gcccggttct caggctccct ccttgggggc      600
aaagctgccc tgacactgtc aggtgtgcag cctgaggacg aggctgagta ttactgcctg      660
ctctactatg tggtgctca gccttatgtg gtattcggcg agggaccaa ggtgaccgtc       720 ctcggtcagc ccaaggctgc cccctcg                                          747
```

```
<210> SEQ ID NO 18
<211> LENGTH: 741
<212> TYPE: DNA
<213> ORGANISM: Homo sapiens

<400> SEQUENCE: 18
caggtgcagc tggtgcagtc tgggggaggc gtggtccagc ctgggaggtc cctgagactc       60
tcctgtgcag cgtctggatt caccttcagt agctatggca tgcactgggt ccgccaggat      120
ccagggaagg gctgatgtg gtctcatct attagtactg atgggagtgc acaaaatac        180 gcggactccg tgaagggccg attcaccatc tccagagaca cgccaagaa cacggtgtct      240 ctacaaatga acagtctgag agccgaagac acggctgtct attattgtgt aggaggattt      300
ttaggctggt ggggccaggg caccctggtc accgtctctt caggtggcgg cggttccgga     360
ggtggtggtt ctggcggtgg tggcagcgaa attgtgttga cgcagtctcc agccaccctg     420
tctttgtctc caggggaaag agccaccctc tcctgcaggg ccagccagag tgttggcggc    480
agctacttag cctggtacca acagaaacct ggccaggctc ccaggctcct catctatggt     540
gcatccagga gggccactgg catcccagcc aggttcagtg gcagtgggtc tgggacagat     600
ttcacgctca ccatcagcag tctgcaacct gaagattttg caagttactt ttgtcaacag    660
actaacactt ttcctctcac cttcggcggg gggaccaagg tggagatcaa acgaactgtg    720
gctgcaccaa cggcggccgc a                                                741
```

```
<210> SEQ ID NO 19
<211> LENGTH: 765
<212> TYPE: DNA
<213> ORGANISM: Homo sapiens

<400> SEQUENCE: 19
gaggtgcagc tggtgcagtc tgggggaggc ttggtcaagc ctggagggtc cctgagactc       60
tcctgtgcag cctctggatt cagcttcaac aactatgccg ggagctgggt ccgccaggct     120
ccagggaagg gctggaatg gatctcagca ttgagtagtg gtggtgatac acatactac      180 gcagactccg tggcgggccg cttcgccatc tccagagaca attccaagaa tactctgtat     240
ctccaaatgc acagtctgag agccgaggac acggccatat attattgtgc gcaggatccc     300
gtcgtgggag cacctgggta cttcggtctc tggggccgtg aaccctggt caccgtctcc     360 tcaggtggcg gcggttccgg aggtggtggt tctggcggtg gtggcagcca gtctgtgctg    420
actcagccac cctccgcgtc cgggtcttct ggacagtcag tcaccatctc ctgcactgga    480
accagcagtg acattggtgg ttataactat gtctcctggt accaacagca cccaggcaaa     540
gcccccaaac tcatgattta tgaggtcagt aagcggccct caggggtttc tgatcgcttc     600
tctggctcca agtctggcag cacggcctcc ctgcacatct ctggcctcca ggctgaggac    660
gaggcagatt attactgcag ctcatactca agcaacaacg ctcctatgt cttcggaagt    720 gggaccaagg tcgccgtcct aggtcagccc aaggccgccc cctcg                     765
```

<210> SEQ ID NO 20
<211> LENGTH: 759
<212> TYPE: DNA
<213> ORGANISM: Homo sapiens

<400> SEQUENCE: 20

```
caggtacagc tgcagcagtc aggtccagga ctggtgaagc cctcgcagac cctctcactc      60
acctgtgcca tctccgggga cagtgtctct accaacagtg ctgcttggaa ctggatcagg     120
cagtccccat cgagaggcct tgagtggctg gaaggacat actacaggtc caagtggtat      180
aatgattatg cagtatctgt gaaaagtcga ataaccatca gcccagacac atccaagaat     240
cacttctccc tgcagctgaa ctctgtgact cccgaggaca cggctgtgta ttactgtgca     300
agagagggaa atgatgcttt tgatatctgg ggccaaggga caatggtcac cgtctcctca     360
ggtggcggcg gttccggagg tggtggttct ggcggtggtg gcagccagtc tgccctgact     420
cagccaccct cagcgtctgg gaccccggg cagagggtca ccatctcttg ttctggaagc     480
agctccaaca tcggaagtaa tactgtaaac tggtaccagc agctcccagg aacggccccc     540
aaactcctca tctatagtaa taatcagcgg ccctcagggg tccctgaccg attctctggc     600
tccaagtctg gcacctcagc ctccctggcc atcagtgggc tccagtctga ggatgaagct     660
gattattact gtgaagcatg ggatgacagc ctgaatggtc cggtgttcgg cggagggacc     720
aagctgaccg tcctaggtca gcccaaggct acccccctcg                           759
```

<210> SEQ ID NO 21
<211> LENGTH: 250
<212> TYPE: PRT
<213> ORGANISM: Homo sapiens

<400> SEQUENCE: 21

```
Glu Val Gln Leu Val Gln Ser Gly Gly Gly Leu Val Gln Pro Gly Gly
1               5                   10                  15

Ser Leu Arg Leu Ser Cys Ser Ala Ser Gly Phe Thr Phe Ser Asn Tyr
            20                  25                  30

Ala Met His Trp Val Arg Arg Ala Pro Gly Lys Gly Leu Glu Tyr Val
        35                  40                  45

Ser Ala Ile Ser Ser Asn Gly Gly Ser Thr Tyr Tyr Ala Asp Ser Val
    50                  55                  60

Lys Gly Arg Phe Thr Ile Ser Arg Asp Asn Pro Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Gly Arg Pro Tyr Pro Leu Asp Val Trp Gly Lys Gly Thr Leu
            100                 105                 110

Val Thr Val Ser Ser Gly Gly Gly Gly Ser Gly Gly Gly Gly Ser Gly
        115                 120                 125

Gly Gly Gly Ser Gln Ser Val Leu Thr Gln Pro Ser Ala Ser Gly
    130                 135                 140

Thr Pro Gly Gln Arg Val Thr Ile Ser Cys Ser Gly Ser Ser Ser Asn
145                 150                 155                 160

Ile Glu Ser His Ala Val Asn Trp Tyr Gln His Leu Pro Gly Ser Ala
                165                 170                 175

Pro Lys Leu Leu Ile Tyr Phe Asn Asn His Arg Pro Ser Gly Val Pro
            180                 185                 190

Glu Arg Phe Ser Ala Ser Lys Ser Gly Thr Ser Ala Ser Leu Ala Ile
```

```
                195                 200                 205
Ser Gly Leu Gln Ser Glu Asp Glu Ala Asp Tyr Tyr Cys Ala Ala Trp
    210                 215                 220

Asp Asp Ser Leu Asn Gly Pro Val Phe Gly Gly Thr Lys Leu Thr
225                 230                 235                 240

Val Leu Gly Gln Pro Lys Ala Ala Pro Ser
                245                 250

<210> SEQ ID NO 22
<211> LENGTH: 249
<212> TYPE: PRT
<213> ORGANISM: Homo sapiens

<400> SEQUENCE: 22

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Thr Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Gly Asp Leu Asp Tyr Trp Gly Gln Gly Thr Thr Val Thr Val
            100                 105                 110

Ser Ser Gly Gly Gly Gly Ser Gly Gly Gly Gly Ser Gly Gly Gly Gly
        115                 120                 125

Ser Gln Thr Val Val Thr Gln Glu Pro Ser Leu Thr Val Ser Pro Gly
    130                 135                 140

Gly Thr Val Thr Leu Thr Cys Ala Ser Ser Thr Gly Ala Val Thr Ser
145                 150                 155                 160

Gly Tyr Tyr Pro Asn Trp Phe Gln Gln Lys Pro Gly Gln Ala Pro Arg
                165                 170                 175

Ala Leu Ile Tyr Ser Thr Ser Asn Lys His Ser Trp Thr Pro Ala Arg
            180                 185                 190

Phe Ser Gly Ser Leu Leu Gly Gly Lys Ala Ala Leu Thr Leu Ser Gly
        195                 200                 205

Val Gln Pro Glu Asp Glu Ala Glu Tyr Tyr Cys Leu Leu Tyr Tyr Gly
    210                 215                 220

Gly Ala Gln Pro Tyr Val Val Phe Gly Gly Gly Thr Lys Val Thr Val
225                 230                 235                 240

Leu Gly Gln Pro Lys Ala Ala Pro Ser
                245

<210> SEQ ID NO 23
<211> LENGTH: 247
<212> TYPE: PRT
<213> ORGANISM: Homo sapiens

<400> SEQUENCE: 23

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
```

```
                   20                  25                  30
Gly Met His Trp Val Arg Gln Asp Pro Gly Lys Gly Leu Met Trp Val
            35                  40                  45
Ser Ser Ile Ser Thr Asp Gly Ser Ala Thr Lys Tyr Ala Asp Ser Val
        50                  55                  60
Lys Gly Arg Phe Thr Ile Ser Arg Asp Asn Ala Lys Asn Thr Val Ser
65                  70                  75                  80
Leu Gln Met Asn Ser Leu Arg Ala Glu Asp Thr Ala Val Tyr Tyr Cys
                85                  90                  95
Val Gly Gly Phe Leu Gly Trp Trp Gly Gln Gly Thr Leu Val Thr Val
            100                 105                 110
Ser Ser Gly Gly Gly Ser Gly Gly Gly Ser Gly Gly Gly Gly
            115                 120                 125
Ser Glu Ile Val Leu Thr Gln Ser Pro Ala Thr Leu Ser Leu Ser Pro
            130                 135                 140
Gly Glu Arg Ala Thr Leu Ser Cys Arg Ala Ser Gln Ser Val Gly Gly
145                 150                 155                 160
Ser Tyr Leu Ala Trp Tyr Gln Gln Lys Pro Gly Gln Ala Pro Arg Leu
                165                 170                 175
Leu Ile Tyr Gly Ala Ser Arg Arg Ala Thr Gly Ile Pro Ala Arg Phe
            180                 185                 190
Ser Gly Ser Gly Ser Gly Thr Asp Phe Thr Leu Thr Ile Ser Ser Leu
            195                 200                 205
Gln Pro Glu Asp Phe Ala Ser Tyr Phe Cys Gln Gln Thr Asn Thr Phe
            210                 215                 220
Pro Leu Thr Phe Gly Gly Gly Thr Lys Val Glu Ile Lys Arg Thr Val
225                 230                 235                 240
Ala Ala Pro Thr Ala Ala Ala
                245

<210> SEQ ID NO 24
<211> LENGTH: 255
<212> TYPE: PRT
<213> ORGANISM: Homo sapiens

<400> SEQUENCE: 24

Glu Val Gln Leu Val Gln Ser Gly Gly Gly Leu Val Lys Pro Gly Gly
1               5                   10                  15
Ser Leu Arg Leu Ser Cys Ala Ala Ser Gly Phe Ser Phe Asn Asn Tyr
            20                  25                  30
Ala Gly Ser Trp Val Arg Gln Ala Pro Gly Lys Gly Leu Glu Trp Ile
        35                  40                  45
Ser Ala Leu Ser Ser Gly Gly Asp Thr Thr Tyr Ala Asp Ser Val
    50                  55                  60
Ala Gly Arg Phe Ala Ile Ser Arg Asp Asn Ser Lys Asn Thr Leu Tyr
65                  70                  75                  80
Leu Gln Met His Ser Leu Arg Ala Glu Asp Thr Ala Ile Tyr Tyr Cys
                85                  90                  95
Ala Gln Asp Pro Val Val Gly Ala Pro Gly Tyr Phe Gly Leu Trp Gly
            100                 105                 110
Arg Gly Thr Leu Val Thr Val Ser Gly Gly Gly Ser Gly Gly
        115                 120                 125
Gly Gly Ser Gly Gly Gly Ser Gln Ser Val Leu Thr Gln Pro Pro
            130                 135                 140
```

Ser Ala Ser Gly Ser Gly Gln Ser Val Thr Ile Ser Cys Thr Gly
145                 150                 155                 160

Thr Ser Ser Asp Ile Gly Gly Tyr Asn Tyr Val Ser Trp Tyr Gln Gln
                165                 170                 175

His Pro Gly Lys Ala Pro Lys Leu Met Ile Tyr Glu Val Ser Lys Arg
            180                 185                 190

Pro Ser Gly Val Ser Asp Arg Phe Ser Gly Ser Lys Ser Gly Ser Thr
        195                 200                 205

Ala Ser Leu His Ile Ser Gly Leu Gln Ala Glu Asp Glu Ala Asp Tyr
    210                 215                 220

Tyr Cys Ser Ser Tyr Ser Ser Asn Asn Ala Pro Tyr Val Phe Gly Ser
225                 230                 235                 240

Gly Thr Lys Val Ala Val Leu Gly Gln Pro Lys Ala Ala Pro Ser
                245                 250                 255

<210> SEQ ID NO 25
<211> LENGTH: 253
<212> TYPE: PRT
<213> ORGANISM: Homo sapiens

<400> SEQUENCE: 25

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Thr Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Ser Pro Asp Thr Ser Lys Asn
65                  70                  75                  80

His Phe Ser Leu Gln Leu Asn Ser Val Thr Pro Glu Asp Thr Ala Val
                85                  90                  95

Tyr Tyr Cys Ala Arg Glu Gly Asn Asp Ala Phe Asp Ile Trp Gly Gln
            100                 105                 110

Gly Thr Met Val Thr Val Ser Ser Gly Gly Gly Ser Gly Gly Gly
        115                 120                 125

Gly Ser Gly Gly Gly Gly Ser Gln Ser Ala Leu Thr Gln Pro Pro Ser
    130                 135                 140

Ala Ser Gly Thr Pro Gly Gln Arg Val Thr Ile Ser Cys Ser Gly Ser
145                 150                 155                 160

Ser Ser Asn Ile Gly Ser Asn Thr Val Asn Trp Tyr Gln Gln Leu Pro
                165                 170                 175

Gly Thr Ala Pro Lys Leu Leu Ile Tyr Ser Asn Asn Gln Arg Pro Ser
            180                 185                 190

Gly Val Pro Asp Arg Phe Ser Gly Ser Lys Ser Gly Thr Ser Ala Ser
        195                 200                 205

Leu Ala Ile Ser Gly Leu Gln Ser Glu Asp Glu Ala Asp Tyr Tyr Cys
    210                 215                 220

Glu Ala Trp Asp Asp Ser Leu Asn Gly Pro Val Phe Gly Gly Gly Thr
225                 230                 235                 240

Lys Leu Thr Val Leu Gly Gln Pro Lys Ala Thr Pro Ser
                245                 250

<210> SEQ ID NO 26
<211> LENGTH: 6

```
<212> TYPE: PRT
<213> ORGANISM: Homo sapiens

<400> SEQUENCE: 26

Ser Asn Tyr Ala Met His
1               5

<210> SEQ ID NO 27
<211> LENGTH: 17
<212> TYPE: PRT
<213> ORGANISM: Homo sapiens

<400> SEQUENCE: 27

Ala Ile Ser Ser Asn Gly Gly Ser Thr Tyr Tyr Ala Asp Ser Val Lys
1               5                   10                  15

Gly

<210> SEQ ID NO 28
<211> LENGTH: 8
<212> TYPE: PRT
<213> ORGANISM: Homo sapiens

<400> SEQUENCE: 28

Gly Arg Pro Tyr Pro Leu Asp Val
1               5

<210> SEQ ID NO 29
<211> LENGTH: 12
<212> TYPE: PRT
<213> ORGANISM: Homo sapiens

<400> SEQUENCE: 29

Gly Ser Ser Ser Asn Ile Glu Ser His Ala Val Asn
1               5                   10

<210> SEQ ID NO 30
<211> LENGTH: 7
<212> TYPE: PRT
<213> ORGANISM: Homo sapiens

<400> SEQUENCE: 30

Phe Asn Asn His Arg Pro Ser
1               5

<210> SEQ ID NO 31
<211> LENGTH: 7
<212> TYPE: PRT
<213> ORGANISM: Homo sapiens

<400> SEQUENCE: 31

Ala Ala Trp Asp Asp Ser Leu
1               5

<210> SEQ ID NO 32
<211> LENGTH: 5
<212> TYPE: PRT
<213> ORGANISM: Homo sapiens

<400> SEQUENCE: 32

Asn Tyr Ala Met Thr
1               5

<210> SEQ ID NO 33
<211> LENGTH: 17
```

-continued

```
<212> TYPE: PRT
<213> ORGANISM: Homo sapiens

<400> SEQUENCE: 33

Ala Ile Ser Gly Ser Gly Gly Ser Thr Tyr Tyr Ala Asp Ser Val Lys
1               5                   10                  15
Gly

<210> SEQ ID NO 34
<211> LENGTH: 5
<212> TYPE: PRT
<213> ORGANISM: Homo sapiens

<400> SEQUENCE: 34

Gly Asp Leu Asp Tyr
1               5

<210> SEQ ID NO 35
<211> LENGTH: 13
<212> TYPE: PRT
<213> ORGANISM: Homo sapiens

<400> SEQUENCE: 35

Ser Ser Thr Gly Ala Val Thr Ser Gly Tyr Tyr Pro Asn
1               5                   10

<210> SEQ ID NO 36
<211> LENGTH: 7
<212> TYPE: PRT
<213> ORGANISM: Homo sapiens

<400> SEQUENCE: 36

Ser Thr Ser Asn Lys His Ser
1               5

<210> SEQ ID NO 37
<211> LENGTH: 12
<212> TYPE: PRT
<213> ORGANISM: Homo sapiens

<400> SEQUENCE: 37

Leu Leu Tyr Tyr Gly Gly Ala Gln Pro Tyr Val Val
1               5                   10

<210> SEQ ID NO 38
<211> LENGTH: 5
<212> TYPE: PRT
<213> ORGANISM: Homo sapiens

<400> SEQUENCE: 38

Ser Tyr Gly Met His
1               5

<210> SEQ ID NO 39
<211> LENGTH: 17
<212> TYPE: PRT
<213> ORGANISM: Homo sapiens

<400> SEQUENCE: 39

Ser Ile Ser Thr Asp Gly Gly Ser Thr Tyr Tyr Ala Asp Ser Val Lys
1               5                   10                  15
Gly
```

```
<210> SEQ ID NO 40
<211> LENGTH: 5
<212> TYPE: PRT
<213> ORGANISM: Homo sapiens

<400> SEQUENCE: 40

Gly Phe Leu Gly Trp
1               5

<210> SEQ ID NO 41
<211> LENGTH: 12
<212> TYPE: PRT
<213> ORGANISM: Homo sapiens

<400> SEQUENCE: 41

Arg Ala Ser Gln Ser Val Gly Gly Ser Tyr Leu Ala
1               5                   10

<210> SEQ ID NO 42
<211> LENGTH: 7
<212> TYPE: PRT
<213> ORGANISM: Homo sapiens

<400> SEQUENCE: 42

Gly Ala Ser Arg Arg Ala Thr
1               5

<210> SEQ ID NO 43
<211> LENGTH: 9
<212> TYPE: PRT
<213> ORGANISM: Homo sapiens

<400> SEQUENCE: 43

Gln Gln Thr Asn Thr Phe Pro Leu Thr
1               5

<210> SEQ ID NO 44
<211> LENGTH: 4
<212> TYPE: PRT
<213> ORGANISM: Homo sapiens

<400> SEQUENCE: 44

Asn Tyr Ala Gly
1

<210> SEQ ID NO 45
<211> LENGTH: 17
<212> TYPE: PRT
<213> ORGANISM: Homo sapiens

<400> SEQUENCE: 45

Ala Leu Ser Ser Gly Gly Asp Thr Thr Tyr Tyr Ala Asp Ser Val Ala
1               5                   10                  15

Gly

<210> SEQ ID NO 46
<211> LENGTH: 12
<212> TYPE: PRT
<213> ORGANISM: Homo sapiens

<400> SEQUENCE: 46

Asp Pro Val Val Gly Ala Pro Gly Tyr Phe Gly Leu
1               5                   10
```

<210> SEQ ID NO 47
<211> LENGTH: 13
<212> TYPE: PRT
<213> ORGANISM: Homo sapiens

<400> SEQUENCE: 47

Gly Thr Ser Ser Asp Ile Gly Gly Tyr Asn Tyr Val Ser
1               5                   10

<210> SEQ ID NO 48
<211> LENGTH: 7
<212> TYPE: PRT
<213> ORGANISM: Homo sapiens

<400> SEQUENCE: 48

Glu Val Ser Lys Arg Pro Ser
1               5

<210> SEQ ID NO 49
<211> LENGTH: 11
<212> TYPE: PRT
<213> ORGANISM: Homo sapiens

<400> SEQUENCE: 49

Ser Ser Tyr Ser Ser Asn Asn Ala Pro Tyr Val
1               5                   10

<210> SEQ ID NO 50
<211> LENGTH: 6
<212> TYPE: PRT
<213> ORGANISM: Homo sapiens

<400> SEQUENCE: 50

Asn Ser Ala Ala Trp Asn
1               5

<210> SEQ ID NO 51
<211> LENGTH: 18
<212> TYPE: PRT
<213> ORGANISM: Homo sapiens

<400> SEQUENCE: 51

Arg Thr Tyr Tyr Arg Ser Lys Trp Tyr Asn Asp Tyr Ala Val Ser Val
1               5                   10                  15

Lys Ser

<210> SEQ ID NO 52
<211> LENGTH: 8
<212> TYPE: PRT
<213> ORGANISM: Homo sapiens

<400> SEQUENCE: 52

Glu Gly Asn Asp Ala Phe Asp Ile
1               5

<210> SEQ ID NO 53
<211> LENGTH: 12
<212> TYPE: PRT
<213> ORGANISM: Homo sapiens

<400> SEQUENCE: 53

Gly Ser Ser Ser Asn Ile Gly Ser Asn Thr Val Asn
1               5                   10

```
<210> SEQ ID NO 54
<211> LENGTH: 7
<212> TYPE: PRT
<213> ORGANISM: Homo sapiens

<400> SEQUENCE: 54

Ser Asn Asn Gln Arg Pro Ser
1               5

<210> SEQ ID NO 55
<211> LENGTH: 11
<212> TYPE: PRT
<213> ORGANISM: Homo sapiens

<400> SEQUENCE: 55

Glu Ala Trp Asp Asp Ser Leu Asn Gly Pro Val
1               5                   10
```